US006787570B2

(12) United States Patent
Sikorski et al.

(10) Patent No.: US 6,787,570 B2
(45) Date of Patent: Sep. 7, 2004

(54) SUBSTITUTED N-CYCLOALKYL-N-BENZYL AMINOALCOHOL COMPOUNDS USEFUL FOR INHIBITING CHOLESTERYL ESTER TRANSFER PROTEIN ACTIVITY

(75) Inventors: James A. Sikorski, Des Peres, MO (US); Richard C. Durley, Chesterfield, MO (US); Margaret L. Grapperhaus, Troy, IL (US); Deborah A. Mischke, Defiance, MO (US); Emily J. Reinhard, Chesterfield, MO (US); Barry L. Parnas, University City, MO (US); Melvin L. Rueppel, St. Louis, MO (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/320,858

(22) Filed: Dec. 16, 2002

(65) Prior Publication Data

US 2003/0191306 A1 Oct. 9, 2003

Related U.S. Application Data

(63) Continuation of application No. 09/760,627, filed on Jan. 16, 2001, now abandoned, which is a continuation of application No. 09/401,916, filed on Sep. 23, 1999, now abandoned.

(51) Int. Cl.[7] ...................... A61K 31/137; C07C 215/03

(52) U.S. Cl. ....................... 514/645; 514/654; 514/655; 564/300; 564/374; 564/378; 564/384; 564/387; 564/389

(58) Field of Search ................................ 514/645, 654, 514/655; 564/300, 374, 378, 384, 387, 389

(56) References Cited

U.S. PATENT DOCUMENTS

| | | | | |
|---|---|---|---|---|
| 2,700,686 | A | 1/1955 | Dickey | 260/633 |
| 3,386,987 | A | 6/1968 | Weaver | 260/152 |
| 3,682,975 | A | 8/1972 | Tesoro | 260/348 |
| 3,699,123 | A | 10/1972 | Seeman | 260/326 |
| 3,705,907 | A | 12/1972 | Troxler | 260/326 |
| 3,996,382 | A | 12/1976 | Berntsson | 424/330 |
| 4,333,952 | A | 6/1982 | McDonald | 424/330 |
| 4,363,759 | A | 12/1982 | Boguslaski | 260/112.7 |
| 4,391,821 | A | 7/1983 | Korbonits | 424/283 |
| 4,764,178 | A | 8/1988 | Gregory | 8/471 |
| 4,960,883 | A | 10/1990 | Tanabe | 540/575 |
| 5,064,264 | A | 11/1991 | Ducharme | 385/130 |
| 5,198,448 | A | 3/1993 | Fujioka | 514/312 |
| 5,348,961 | A | 9/1994 | Iwata | 514/312 |
| 6,008,332 | A | 12/1999 | Herzig | 534/789 |

FOREIGN PATENT DOCUMENTS

| | | |
|---|---|---|
| CS | 272662 | 2/1991 |
| DE | 2011051 | 9/1970 |
| DE | 2154477 | 5/1972 |
| DE | 2346337 | 4/1974 |
| DE | 2458624 | 7/1975 |
| DE | 19627430 | 1/1998 |
| EP | 0022321 | 1/1981 |
| EP | 0004024 | 2/1982 |
| EP | 0024122 | 2/1983 |
| EP | 796846 | 9/1997 |
| EP | 801060 | 10/1997 |
| EP | 818197 | 1/1998 |
| EP | 818448 | 1/1998 |
| EP | 0918055 | 5/1999 |
| FR | 2232311 | 1/1975 |
| FR | 2258172 | 8/1975 |
| GB | 1297057 | 11/1972 |
| GB | 1361409 | 7/1974 |
| GB | 1405444 | 9/1975 |
| GB | 1445438 | 8/1976 |
| GB | 2305665 | 4/1997 |
| JP | 09078277 | 3/1997 |
| JP | 10287662 | 10/1998 |
| WO | 95/23142 | 8/1995 |
| WO | 9604249 | 2/1996 |
| WO | 98/39299 | 9/1998 |
| WO | 98/50029 | 11/1998 |
| WO | 99/14204 | 3/1999 |

OTHER PUBLICATIONS

P. Dunn et al., "The Synthesis of Fluorine–containing Pterins", Tetrahedron, vol. 52, No. 40, pp. 13017–13206, 1996.

T. Morie et al., "Synthesis and Biological Activities of the Optical Isomers of (±)–4–Amino–5–chloro–2–ethoxy–N–[[4–(4–fluorobenzyl)–2–morpholinyl]methyl]benzamide (Mosapride)", Chem. Pharm. Bull., vol. 42(4), 877–882, 1994.

(List continued on next page.)

*Primary Examiner*—Richard L. Raymond
(74) *Attorney, Agent, or Firm*—Peter C. Richardson; Gregg C. Benson; Lisa A. Samuels

(57) ABSTRACT

The invention relates to substituted N-Alkyl/Alkenyl/Cycloalkyl/Heterocycyl N-Aryl/Heteroaryl tertiary-Heteroalkylamine compounds useful as inhibitors of cholesteryl ester transfer protein (CETP; plasma lipid transfer protein-I) and compounds, compositions and methods for treating atherosclerosis and other coronary artery disease. Preferred tertiary-heteroalkylamine compounds are substituted N-cycloalkyl N-benzyl aminoalcohols. A specific N-cycloalkyl N-benzyl aminoalcohol is the compound:

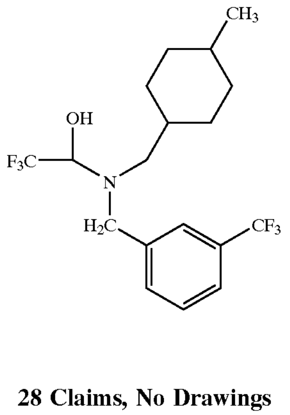

28 Claims, No Drawings

OTHER PUBLICATIONS

C. Weatherbee et al., "New approach to tert–β–chloroalkylamines. Synthesis of β–chloroalkylaminoethylhydroquinones", J. Org. Chem., 21, 1138–1141, 1956.

P. Bravo et al., "New Fluorinated Chiral Synthons", Tetrahedron: Assymmetry, vol. 5, No. 6, pp. 987–1004, 1994.

S. Kutkevicius and S. Rutkauskas "γ–Chloro–β–Hydroxypropyl Derivatives and their Reaction Products. VI. N–Mono– and N,N–Bis–β,γ–Epoxypropylamines", Lietuvos TSR Aukst. Mokyklu Mokslo Darbai, Chemija ir Chemine Technologija, vol. 8, pp. 99–104 (1967).

S. Kutkevicius and E. A. Samarskis, "γ–Chloro–β–Hydroxypropyl Derivatives of Aromatic Amines and their Reaction Products. XVII. Methyldiphenylamine", Lietuvos TSR Aukst. Mokyklu Mokslo Dårbai, Chemija ir Chemine Technologija, vol. 17, pp. 151–154 (1975).

M.S. Kuo et al., "Discovery, Isolation, Structure Elucidation, and Biosynthesis of U–106305, a Cholesteryl Ester Transfer Protein Inhibitor from UC 11136", J. Am. Chem. Soc., vol. 117, 10629–10634, 1995.

A.G.M. Barrett et al., "Total Synthesis and Stereochemical Assignment of the Quinquecyclopropane–Containing Cholesteryl Ester Transfer Protein Inhibitor U–106305", J. Am. Chem. Soc., vol. 118, 7863–7864, 1997.

S.J. Coval et al., "Wiedendiol–A and –B Cholesteryl Ester Transfer Protein Inhibitors from the Marine Sponge *Xestospongla Wiedenmayerl*", Biorg. Med. Chem. Lett., vol. 5, 605–610, 1995.

T. Pietzonka et al., "Phosphonate–containing Analogs of Cholesteryl Ester as Novel Inhibitors of Cholesteryl Ester Transfer Protein", Biorg. Med. Chem. Lett., vol. 6, 1951–1954, 1996.

S.J. Busch and J.A.K. Harmony, "Cholesteryl Ester Analogs Inhibit Cholesteryl Ester but not Triglyceride Transfer Catalyzed by the Plasma Cholesteryl Ester–Triglyceride Transfer Protein", Lipids, vol. 25, 216–220, 1990.

J.C. Lee et al., "A Cholesteryl Ester Transfer Protein Inhibitor from an Insect–associated Fungus", J. Antibiot., vol. 49, 693–696, 1996.

R. E. Morton and D. B. Zilversmit, "Purification and Characterization of Lipid Transfer Protein(s) from Human Lipoprotein–deficient Plasma", J. Lipid Res., vol. 23, 1058–1067, 1982.

D.T. Connolly et al., "Inactivation of Cholesteryl Ester Transfer Protein by Cysteine Modification", Biochem. Biophys. Res Commun., vol. 223, 42–47, 1996.

C.L. Bisgaier et al., "Cholesteryl Ester Transfer Protein Inhibition by PD 140195", Lipids, vol. 29, 811–818, 1994.

Y. Xia et al., "Substituted 1,3,5–Triazines as Cholesteryl Ester Transfer Protein Inhibitors", Biorg. Med. Chem. Lett., vol. 6, 919–922, 1996.

A. Silhankova et al., "Preparation of Some Derivatives of Benzo[ij]quinolizine)", Collect. Czech. Chem. Commun., 50(5), 1048–56, 1985.

P. Johncock et al., "The Relative Reactivity of Primary and Secondary Amine Hydrogen Atoms of Aromatic Amines with Epichlorohydrin and N– and O–Glycidyl", J. Polym. Sci., Polym. Chem. Ed., 23(2), 291–301, 1985.

S. Kutkevichius and V. Daraskaite, "γ–Chloro–β–hydroxypropyl derivatives of aromatic amines and products of their conversion. XI. γ–Chloro–β–hydroxypropyl derivatives of 3–fluoro– and 4–fluoroaniline, 1,5–napthylenediamine, and bispyrido[5,6–af]naphthalene", Liet. TSR Aukst: Mokyklu Mokslo Darb., Chem. Chem. Technol., No. 13, 111–117, 1971.

R. Zentel et al., "Synthesis and nonlinear optical characteristics of crosslinked and linear epoxy polymers with pendant tolane chromophores", Makromol. Chem., 194(3), 859–868, 1993.

S. N. Suleimanov et al., "Fireproofing modifiers for epoxy resin compositions", Plasticheskie Massy, (4), 21–22, 1995.

L. Lebreton et al., "Structure–immunosuppressive activity relationships of new analogues of 15–deoxyspergualin. 2. Structural Modifications of the Spermidine Moiety", J. Med. Chem., 42, 4749–4763, 1999.

R. J. Bergeron et al., "Development of a hypusine reagent for Peptide Synthesis", J. Org. Chem., 62, 3285–3290, 1997.

SUBSTITUTED N-CYCLOALKYL-N-BENZYL AMINOALCOHOL COMPOUNDS USEFUL FOR INHIBITING CHOLESTERYL ESTER TRANSFER PROTEIN ACTIVITY

This is a continuation under 37 C.F.R 1.53(b) of pending prior application Ser. No. 09/760,627 filed on Jan. 16, 2001, now abandoned which is a continuation of application Ser. No. 09/401,916, filed on Sep. 23, 1999 now abandoned.

FIELD OF THE INVENTION

This invention is in the field of treating cardiovascular disease, and specifically relates to compounds, compositions and methods for treating atherosclerosis and other coronary artery disease. More particularly, the invention relates to substituted N-Aliphatic-N-Aromatictertiary-Heteroalkylamine compounds that inhibit cholesteryl ester transfer protein (CETP), also known as plasma lipid transfer protein-I.

BACKGROUND OF THE INVENTION

Numerous studies have demonstrated that a low plasma concentration of high density lipoprotein (HDL) cholesterol is a powerful risk factor for the development of atherosclerosis (Barter and Rye, *Atherosclerosis,* 121, 1–12 (1996)). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL) and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above 180 mg/dl) and low HDL cholesterol (below 35 mg/dl) have been shown to be important contributors to the development of atherosclerosis. Other diseases, such as peripheral vascular disease, stroke, and hypercholesterolaemia are negatively affected by adverse HDL/LDL ratios. Inhibition of CETP by the subject compounds is shown to effectively modify plasma HDL/LDL ratios, and to check the progress and/or formation of these diseases.

CETP is a plasma protein that facilitates the movement of cholesteryl esters and triglycerides between the various lipoproteins in the blood (Tall, *J. Lipid Res.,* 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile (McCarthy, *Medicinal Res. Revs.,* 13, 139–59 (1993); Sitori, *Pharmac. Ther.,* 67,443–47 (1995)). This exact phenomenon was first demonstrated by Swenson et al., (*J. Biol. Chem.,* 264, 14318 (1989)) with the use of a monoclonal antibody that specifically inhibited CETP. In rabbits, the antibody caused an elevation of the plasma HDL cholesterol and a decrease in LDL cholesterol. Son et al. (*Biochim. Biophys. Acta* 795, 743–480 (1984)), Morton et al. (*J. Lipid Res.* 35, 836–847 (1994)) and Tollefson et al. (*Am. J. Physiol.,* 255, (Endocrinol. Metab. 18, E894–E902 (1988))) describe proteins from human plasma that inhibit CETP. U.S. Pat. No. 5,519,001, issued to Kushwaha et al., describes a 36 amino acid peptide derived from baboon apo C-1 that inhibits CETP activity. Cho et al. (*Biochim. Biophys. Acta* 1391, 133–144 (1998)) describe a peptide from hog plasma that inhibits human CETP. Bonin et al. (*J. Peptide Res.,* 51, 216–225 (1998)) disclose a decapeptide inhibitor of CETP. A depsipeptide fungal metabolite is disclosed as a CETP inhibitor by Hedge et al. in *Bioorg. Med. Chem. Lett.,* 8, 1277–80 (1998).

There have been several reports of non-peptidic compounds that act as CETP inhibitors. Barrett et al. (*J. Am. Chem. Soc.,* 188, 7863–63 (1996)) and Kuo et al. (*J. Am. Chem. Soc.,* 117, 10629–34 (1995)) describe cyclopropane-containing CETP inhibitors. Pietzonka et al. (*Bioorg. Med. Chem. Lett,* 6, 1951–54 (1996)) describe phosphonate-containing analogs of cholesteryl ester as CETP inhibitors. Coval et al. (*Bioorg. Med. Chem. Lett.,* 5, 605–610 (1995)) describe Wiedendiol-A and -B, and related sesquiterpene compounds as CETP inhibitors. Japanese Patent Application No. 10287662-A describes polycyclic, non-amine containing, polyhydroxylic natural compounds possessing CETP inhibition properties. Lee et al. (*J. Antibiotics,* 49, 693–96 (1996)) describe CETP inhibitors derived from an insect fungus. Busch et al. (*Lipids,* 25, 216–220, (1990)) describe cholesteryl acetyl bromide as a CETP inhibitor. Morton and Zilversmit (*J. Lipid Res.,* 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42–47 (1996)) describe other cysteine modification reagents as CETP inhibitors. Xia et al. describe 1,3,5-triazines as CETP inhibitors (*Bioorg. Med. Chem. Lett.,* 6,919–22 (1996)). Bisgaier et al. (*Lipids,* 29, 811–8 (1994)) describe 4-phenyl-5-tridecyl-4H-1,2,4-triazole-thiol as a CETP inhibitor. Oomura et al. disclose non-peptidic tetracyclic and hexacyclic phenols as CETP inhibitors in Japanese Patent Application No. 10287662. In WO Patent Application No. 09914204, Sikorski describes 1,2,4-triazolylthiols useful as chlolesteryl ester transfer protein inhibitors.

Some substituted heteroalkylamine compounds are known. In European Patent Application No. 796846, Schmidt et al. describe 2-aryl-substituted pyridines as cholesteryl ester transfer protein inhibitors useful as cardiovascular agents. One substitutent at C3 of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and artherosclerotic diseases. In European Patent Application No. 818448, Schmidt et al. describe tetrahydroquinoline derivatives as cholesteryl ester transfer protein inhibitors. European Patent Application No. 818197, Schmek et al. describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In WO Patent Application No. 09839299, Muller-Gliemann et al. describe quinoline derivatives as cholesteryl ester transfer protein inhibitors. U.S. Pat. No.

2,700,686, issued to Dickey and Towne, describes N-(2-haloalkyl-2-hydroxyethyl)amines in which the amine is further substituted with either 1 to 2 aliphatic groups or one aromatic group and one aliphatic group. U.S. Pat. No. 2,700,686 further describes a process to prepare the N-(2-haloalkyl-2-hydroxyethyl)amines by reacting halogenated-1,2-epoxyalkanes with the corresponding aliphatic amines and N-alkylanilines and their use as dye intermediates.

SUMMARY OF THE INVENTION

The present invention provides a class of compounds that can be used to inhibit cholesteryl ester transfer protein (CETP) activity and that have the general structure:

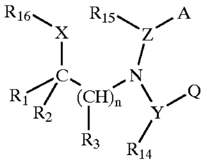

In another aspect, the present invention includes pharmaceutical compositions comprising a pharmaceutically effective amount of the compounds of this invention and a pharmaceutically acceptable carrier.

In another aspect, this invention relates to methods of using these inhibitors as therapeutic agents in humans to inhibit cholesteryl ester transfer protein (CETP) activity, thereby decreasing the concentrations of low density lipoprotein (LDL) and raising the level of high density lipoprotein (HDL), resulting in a therapeutically beneficial plasma lipid profile. The compounds and methods of this invention can also be used to treat dyslipidemia (hypoalphalipoproteinemia), hyperlipoproteinaemia (chylomicronemia and hyperapobetalipoproteinemia), peripheral vascular disease, hypercholesterolaemia, atherosclerosis, coronary artery disease and other CETP-mediated disorders. The compounds can also be used in prophylactic treatment of subjects who are at risk of developing such disorders. The compounds can be used to lower the risk of atherosclerosis. The compounds of this invention would be also useful in prevention of cerebral vascular accident (CVA) or stroke. Besides being useful for human treatment, these compounds are also useful for veterinary treatment of companion animals, exotic animals and farm animals such as primates, rabbits, pigs, horses, and the like.

DESCRIPTION OF THE INVENTION

The present invention relates to a class of compounds comprising substituted N-Aliphatic-N-Aromatictertiary-Heteroalkylamines which are beneficial in the therapeutic and prophylactic treatment of coronary artery disease as given in Formula I-WA (also referred to herein as "alicyclic/cyclic aryl/heteroaryl heteroalkylamines"):

(I-WA)

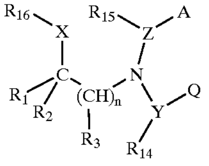

or a pharmaceutically-acceptable salt thereof, wherein;

n is an integer selected from 1 through 4;

A and Q are independently selected from the group consisting of $—CH_2(CR_{37}R_{38})_v—(CR_{33}R_{34})_u—T—(CR_{35}R_{36})_w—H$,

AQ-1

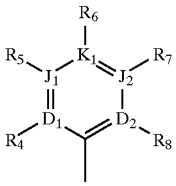

and

AQ-2

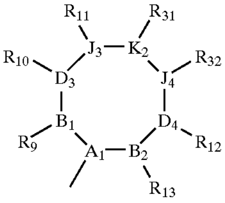

with the provisos that one of A and Q must be AQ-1 and that one of A and Q must be selected from the group consisting of AQ-2 and $—CH_2(CR_{37}R_{38})_v—(CR_{33}R_{34})_u—T—(CR_{35}R_{36})_w—H$;

T is selected from the group consisting of a single covalent bond, O, S S(O), $S(O)_2$, $C(R_{33})═C(R_{35})$, and C≡C;

v is an integer selected from 0 through 1 with the proviso that v is 1 when any one of $R_{33}$, $R_{34}$, $R_{35}$, and $R_{36}$ is aryl or heteroaryl;

u and w are integers independently selected from 0 through 6;

$A_1$ is $C(R_{30})$;

$D_1$, $D_2$, $J_1$, $J_2$ and $K_1$ are independently selected from the group consisting of C, N, O, S and a covalent bond with the provisos that no more than one of $D_1$, $D_2$, $J_1$, $J_2$ and $K_1$ is a covalent bond, no more than one of $D_1$, $D_2$, $J_1$, $J_2$ and $K_1$ is O, no more than one of $D_1$, $D_2$, $J_1$, $J_2$ and $K_1$ is S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ are N;

$B_1$, $B_2$, $D_3$, $D_4$, $J_3$, $J_4$ and $K_2$ are independently selected from the group consisting of C, $C(R_{30})$, N, O, S and a covalent bond with the provisos that no more than 5 of $B_1$, $B_2$, $D_3$, $D_4$, $J_3$, $J_4$ and $K_2$ are a covalent bond, no more than two of $B_1$, $B_2$, $D_3$, $D_4$, $J_3$, $J_4$ and $K_2$ are O, no more than two of $B_1$, $B_2$, $D_3$, $D_4$, $J_3$, $J_4$ and $K_2$ are S, no more than two of $B_1$, $B_2$, $D_3$, $D_4$, $J_3$, $J_4$ and $K_2$ are simultaneously O and S, and no more than two of $B_1$, $B_2$, $D_3$, $D_4$, $J_3$, $J_4$ and $K_2$ are N;

$B_1$ and $D_3$, $D_3$ and $J_3$, $J_3$ and $K_2$, $K_2$ and $J_4$, $J_4$ and $D_4$, and $D_4$ and $B_2$ are independently selected to form an in-ring spacer pair wherein said spacer pair is selected from the group consisting of $C(R_{33})═C(R_{35})$ and N═N with the provisos that AQ-2 must be a ring of at least five contiguous members, that no more than two of the group of said spacer pairs are simultaneously $C(R_{33})═C(R_{35})$, and that no more than one of the group of said spacer pairs can N═N unless the other spacer pairs is other than $C(R_{33})═C(R_{35})$, O, N, and S;

$R_{16}$ is selected from the group consisting of hydrido, alkyl, acyl, aroyl, heteroaroyl, and trialkylsilyl;

X is selected from the group consisting of O, H, F, S, S(O), NH, N(OH), N(alkyl), and N(alkoxy) with the proviso that there is no $R_{16}$ wherein X is H or F;

$R_1$ is selected from the group consisting of haloalkyl, haloalkenyl, haloalkoxyalkyl, and haloalkenyloxyalkyl;

$R_2$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl;

$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Y is selected from a group consisting of a covalent single bond, $(C(R_{14})_2)_q$ wherein q is an integer selected from 1 through 4 and $(CH(R_{14}))_g$—O—$(CH(R_{14}))_p$ wherein g and p are integers independently selected from 0 through 2;

$R_{14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, carboxamidoalkyl;

Z is selected from the group consisting of covalent single bond, $(C(R_{15})_2)_q$ wherein q is an integer selected from 1 through 2, and $(CH(R_{15}))_j$—O—$(CH(R_{15}))_k$ wherein j and k are integers independently selected from 0 through 2;

$R_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that $R_{30}$ is selected to maintain the tetravalent nature of carbon, trivalent nature of nitrogen, the divalent nature of sulfur, and the divalent nature of oxygen;

$R_{30}$, when bonded to $A_1$, is taken together to form an intra-ring linear spacer connecting the $A_1$-carbon at the point of attachment of $R_{30}$ to the point of bonding of a group selected from the group consisting of $R_{10}$, $R_{11}$, $R_{12}$, $R_{31}$, and $R_{32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

$R_{30}$, when bonded to $A_1$, is taken together to form an intra-ring branched spacer connecting the $A_1$-carbon at the point of attachment of $R_{30}$ to the points of bonding of each member of any one of substituent pairs selected from the group consisting of substituent pairs $R_{10}$ and $R_{11}$, $R_{10}$ and $R_{31}$, $R_{10}$ and $R_{32}$, $R_{10}$ and $R_{12}$, $R_{11}$ and $R_{31}$, $R_{11}$ and $R_{32}$, $R_{11}$ and $R_{12}$, $R_{31}$ and $R_{32}$, $R_{31}$ and $R_{12}$, and $R_{32}$ and $R_{12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_4$, $R_5$, $R_6$, $R_7$, $R_8$, $R_9$, $R_{10}$, $R_{11}$, $R_{12}$, $R_{13}$, $R_{31}$, $R_{32}$, $R_{33}$, $R_{34}$, $R_{35}$, and $R_{36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylaridocarbonylamido, arylanidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_4$, $R_5$, $R_6$, $R_7$, $R_8$, $R_9$, $R_{10}$, $R_{11}$, $R_{12}$, $R_{13}$, $R_{31}$, $R_{32}$, $R_{33}$, $R_{34}$, $R_{35}$, and $R_{36}$ are each independently selected to maintain the tetravalent nature of carbon, trivalent nature of nitrogen, the divalent nature of sulfur, and the divalent nature of oxygen, that no more than three of the $R_{33}$ and $R_{34}$ substituents are simultaneously selected from other than the group consisting of of hydrido and halo, and that no more than three of the $R_{35}$ and $R_{36}$ substituents are simultaneously selected from other than the group consisting of of hydrido and halo;

$R_9$, $R_{10}$, $R_{11}$, $R_{12}$, $R_{13}$, $R_{31}$, and $R_{32}$ are independently selected to be oxo with the provisos that $B_1$, $B_2$, $D_3$, $D_4$, $J_3$, $J_4$ and $K_2$ are independently selected from the group consisting of C and S, no more than two of $R_9$, $R_{10}$, $R_{11}$, $R_{12}$, $R_{13}$, $R_{31}$, and $R_{32}$ are simultaneously oxo, and that $R_9$, $R_{10}$, $R_{11}$, $R_{12}$, $R_{13}$, $R_{31}$, and $R_{32}$ are each independently selected to maintain the tetravalent nature of carbon, trivalent nature of nitrogen, the divalent nature of sulfur, and the divalent nature of oxygen;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{31}$, $R_{31}$ and $R_{32}$, $R_{32}$ and $R_{12}$, and $R_{12}$ and $R_{13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, are used at the same time and that no more than one of the group consisting of spacer pairs $R_9$ and $R_{10}$, $R_{10}$ and $R_{11}$, $R_{11}$ and $R_{31}$, $R_{31}$ and $R_{32}$, $R_{32}$ and $R_{12}$, and $R_{12}$ and $R_{13}$ are used at the same time;

$R_9$ and $R_{11}$, $R_9$ and $R_{12}$, $R_9$ and $R_{13}$, $R_9$ and $R_{31}$, $R_9$ and $R_{32}$, $R_{10}$ and $R_{12}$, $R_{10}$ and $R_{13}$, $R_{10}$ and $R_{31}$, $R_{10}$ and $R_{32}$, $R_{11}$ and $R_{12}$, $R_{11}$ and $R_{13}$, $R_{11}$ and $R_{32}$, $R_{12}$ and $R_{31}$, $R_{13}$ and $R_{31}$, and $R_{13}$ and $R_{32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{37}$ and $R_{38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

In another embodiment of compounds of Formula I-WA, compounds are alcohols and have the Formula I-WO (also referred to herein as "alicyclic/cyclic aryl/heteroaryl aminoalkanols"):

(I-WO)

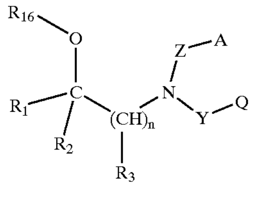

or a pharmaceutically acceptable salt thereof, wherein;

$R_{16}$ is hydrido;

$R_1$, $R_2$, $R_3$, n, A, Y, Q, and Z are defined as given above for Formula I-WA.

In a more specific embodiment of compounds of Formula I-WO, compounds have the Formula I-WOPA:

(I-WOPA)

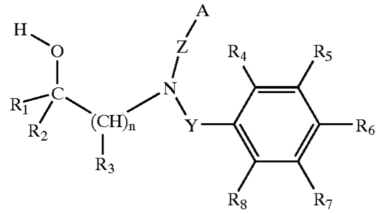

or a pharmaceutically acceptable salt thereof, wherein;

n is an integer selected from 1 through 2;

A is selected from the group consisting of C3–C8 alkyl, C3–C8 alkenyl, C3–C8 alkynyl, C3–C8 haloalkyl, C3–C8 haloalkenyl, C3–C6 alkoxy C1–C2 alkyl, and C3–C8 hydroxyhaloalkyl, wherein each member of group A may be optionally substituted at any carbon up to and including 6 atoms from the point of attachment of A to Z with one or more of the group consisting of $R_{33}$, $R_{34}$, $R_{35}$, and $R_{36}$ with the provisos that $R_{33}$, $R_{34}$, $R_{35}$, and $R_{36}$ must not be attached to the carbon directly linking A to Z and that $R_{33}$, $R_{34}$, $R_{35}$, and $R_{36}$ must be selected from other than aryl and heteroaryl when substituting the carbon 2 atoms from Z wherein Z is a single covalent bond;

$R_1$ is selected from the group consisting of haloalkyl and haloalkoxymethyl;

$R_2$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrido, aryl, alkyl, alkenyl, haloalkyl, and haloalkoxyalkyl;

Y and Z are independently selected from the group consisting of a covalent single bond, oxy and alkylene;

$R_4$ and $R_8$ are independently selected from the group consisting of hydrido and halo;

$R_5$, $R_6$, and $R_7$ are independently selected from the group consisting of hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl;

$R_4$ and $R_5$, $R_5$ and $R_6$, $R_6$ and $R_7$, and $R_7$ and $R_8$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R_4$ and $R_5$, $R_5$ and $R_6$, $R_6$ and $R_7$, and $R_7$ and $R_8$, is used at the same time;

$R_{33}$, $R_{34}$, $R_{35}$, and $R_{36}$ are independently selected from the group group consisting of alkyl, halo, hydroxy, cyano, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl.

In another more specific embodiment of compounds of Formula I-WO, compounds have the Formula I-WOPC:

(I-WOPC)

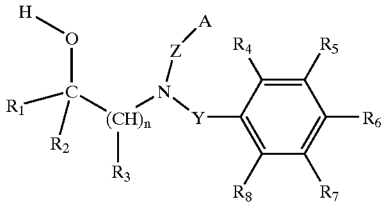

or a pharmaceutically acceptable salt thereof, wherein;

n is an integer selected from 1 through 2;

A is selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{30}$, a ring carbon other than the ring carbon at the point of attachment of A to Z may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{32}$, and a ring carbon or nitrogen atom four atoms from the point of attachment and adjacent to the $R_{11}$ and $R_{32}$ positions may be substituted with $R_{31}$;

$R_1$ is selected from the group consisting of haloalkyl and haloalkoxymethyl;

$R_2$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrido, aryl, alkyl, alkenyl, haloalkyl, and haloalkoxyalkyl;

Y and Z are independently selected from the group consisting of a covalent single bond, oxy and alkylene;

$R_4$ and $R_8$ are independently selected from the group consisting of hydrido and halo;

$R_9$ and $R_{13}$ is halo;

$R_5$, $R_6$, and $R_7$ are independently selected from the group consisting of hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl;

$R_4$ and $R_5$, $R_5$ and $R_6$, $R_6$ and $R_7$, and $R_7$ and $R_8$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R_4$ and $R_5$, $R_5$ and $R_6$, $R_6$ and $R_7$, and $R_7$ and $R_8$, is used at the same time;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl;

$R_{30}$ is selected from the group consisting of alkoxy, alkoxyalkyl, halo, haloalkyl, alkylamino, alkylthio, alkylthioalkyl, alkyl, alkenyl, haloalkoxy, and haloalkoxyalkyl.

In another more specific embodiment of compounds of Formula I-WO, compounds have the Formula I-WOHA:

(I-WOHA)

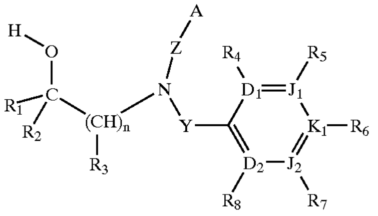

or a pharmaceutically acceptable salt thereof, wherein;

n is an integer selected from 1 through 2;

A is selected from the group consisting of C3–C8 alkyl, C3–C8 alkenyl, C3–C8 alkynyl, C3–C8 haloalkyl, C3–C8 haloalkenyl, C3–C6 alkoxy C1–C2 alkyl, and C3–C8 hydroxyhaloalkyl, wherein each member of group A may be optionally substituted at any carbon up to and including 6 atoms from the point of attachment of A to Z with one or more of the group consisting of $R_{33}$, $R_{34}$, $R_{35}$, and $R_{36}$ with the provisos that $R_{33}$, $R_{34}$, $R_{35}$, and $R_{36}$ must not be attached to the carbon directly linking A to Z and that $R_{33}$, $R_{34}$, $R_{35}$, and $R_{36}$ must be selected from other than aryl and heteroaryl when substituting the carbon 2 atoms from Z wherein Z is a single covalent bond;

$D_1$, $D_2$, $J_1$, $J_2$ and $K_1$ are independently selected from the group consisting of C, N, O, S and a covalent bond with the provisos that no more than one of $D_1$, $D_2$, $J_1$, $J_2$ and $K_1$ is a covalent bond, no more than one of $D_1$, $D_2$, $J_1$, $J_2$ and $K_1$ is O, no more than one of $D_1$, $D_2$, $J_1$, $J_2$ and $K_1$ is S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ are N;

$R_1$ is selected from the group consisting of haloalkyl and haloalkoxymethyl;

$R_2$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrido, aryl, alkyl, alkenyl, haloalkyl, and haloalkoxyalkyl;

Y and Z are independently selected from the group consisting of a covalent single bond, oxy and alkylene;

$R_4$ and $R_8$ are independently selected from the group consisting of hydrido and halo;

$R_5$, $R_6$, and $R_7$ are independently selected from the group consisting of hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl;

$R_4$ and $R_5$, $R_5$ and $R_6$, $R_6$ and $R_7$, and $R_7$ and $R_8$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R_4$ and $R_5$, $R_5$ and $R_6$, $R_6$ and $R_7$, and $R_7$ and $R_8$, is used at the same time;

$R_{33}$, $R_{34}$, $R_{35}$, and $R_{36}$ are independently selected from the group group consisting of alkyl, halo, hydroxy, cyano, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl.

In still another more specific embodiment of compounds of Formula I-WO, compounds have the Formula I-WOHC:

(I-WOHC)

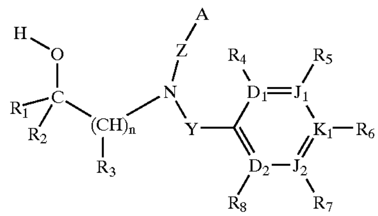

or a pharmaceutically acceptable salt thereof, wherein;

n is an integer selected from 1 through 2;

A is selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{30}$, a ring carbon other than the ring carbon at the point of attachment of A to Z may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{32}$, and a ring carbon or nitrogen atom four atoms from the point of attachment and adjacent to the $R_{11}$ and $R_{32}$ positions may be substituted with $R_{31}$;

$D_1$, $D_2$, $J_1$, $J_2$ and $K_1$ are independently selected from the group consisting of C, N, O, S and a covalent bond with the provisos that no more than one of $D_1$, $D_2$, $J_1$, $J_2$ and $K_1$ is a covalent bond, no more than one of $D_1$, $D_2$, $J_1$, $J_2$ and $K_1$ is O, no more than one of $D_1$, $D_2$, $J_1$, $J_2$ and $K_1$ is S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ are N;

$R_1$ is selected from the group consisting of haloalkyl and haloalkoxymethyl;

$R_2$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrido, aryl, alkyl, alkenyl, haloalkyl, and haloalkoxyalkyl;

Y and Z are independently selected from the group consisting of a covalent single bond, oxy and alkylene;

$R_4$ and $R_8$ are independently selected from the group consisting of hydrido and halo;

$R_9$ and $R_{13}$ is halo;

$R_5$, $R_6$, and $R_7$ are independently selected from the group consisting of hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl;

$R_4$ and $R_5$, $R_5$ and $R_6$, $R_6$ and $R_7$, and $R_7$ and $R_8$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R_4$ and $R_5$, $R_5$ and $R_6$, $R_6$ and $R_7$, and $R_7$ and $R_8$, is used at the same time;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl;

$R_{30}$ is selected from the group consisting of alkoxy, alkoxyalkyl, halo, haloalkyl, alkylamino, alkylthio, alkylthioalkyl, alkyl, alkenyl, haloalkoxy, and haloalkoxyalkyl.

In a preferred specific embodiment of compounds of Formulas I-WOPA, I-WOHA, I-WOPC, and I-WOHC, n is the integer 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrido, methyl, ethyl, propyl, butyl, vinyl, phenyl, 4-trifluoromethylphenyl, 1,1,2,2-tetrafluoroethoxymethyl, trifluoromethoxymethyl, difluoromethyl, pentafluoroethyl, trifluoromethyl, and 2,2,3,3,3-pentafluoropropyl;

$R_3$ is selected from the group consisting of hydrido, phenyl, 4-trifluoromethylphenyl, methyl, ethyl, vinyl, trifluoromethyl, trifluoromethoxymethyl, difluoromethyl, chlorodifluoromethyl, and pentafluoroethyl;

Y and Z are independently selected from the group consisting of a covalent single bond, oxy, and methylene with the proviso that only one of Y and Z are simultaneously oxy;

$R_4$ and $R_8$ are independently selected from the group consisting of hydrido and fluoro;

$R_5$ is selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5 isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5 isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ is selected from the group consisting of chloro, fluoro, hydrido, pentafluoroethyl, 1,1,2,2-tetrafluoroethoxy, trifluoromethyl, and trifluoromethoxy;

$R_7$ is selected from the group consisting of hydrido, fluoro, and trifluoromethyl.

In a more preferred specific embodiment of compounds of Formulas I-WOPA, I-WOHA, I-WOPC, and I-WOHC, n is the integer 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrido, methyl, ethyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrido, phenyl, 4-trifluoromethylphenyl, methyl, trifluoromethyl, difluoromethyl, and chlorodifluoromethyl;

Y and Z are independently selected from a covalent single bond and methylene;

$R_4$ and $R_8$ are independently selected from the group consisting of hydrido and fluoro;

$R_5$ is selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ is selected from the group consisting of chloro, fluoro, hydrido, pentafluoroethyl, 1,1,2,2-tetrafluoroethoxy, and trifluoromethyl;

$R_7$ is selected from the group consisting of hydrido, fluoro, and trifluoromethyl.

In an even more preferred specific embodiment of compounds of Formulas I-WOPA, I-WOHA, I-WOPC, and I-WOHC, n is the integer 1;

$R_1$ is selected from the group consisting of trifluoromethyl, chlorodifluoromethyl, and pentafluoroethyl;

$R_2$ is hydrido, pentafluoroethyl, and trifluoromethyl;

$R_3$ is selected from the group consisting of hydrido, methyl, trifluoromethyl, and difluoromethyl Y and Z are independently selected from the group consisting of a covalent single bond and methylene;

$R_4$ and $R_8$ are independently selected from the group consisting of hydrido and fluoro;

$R_5$ is selected from the group consisting of 5-bromo-2-fluorophenoxy, 4-chloro-3-ethylphenoxy, cyclopentyl, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 2-furyl, isobutyl, isopropoxy, 3-isopropylphenoxy, 3-methylphenoxy, pentafluoroethyl, 3-pentafluoroethylphenoxy, 3-tert-butylphenoxy, 1,1,2,2-tetrafluoroethoxy, 3-(1,1,2,2-tetrafluoroethoxy)phenoxy, 2-(5,6,7,8-tetrahydronaphthyloxy), trifluoromethoxy, 3-trifluoromethoxybenzyloxy, 3-trifluoromethoxyphenoxy, trifluoromethyl, 3-trifluoromethylbenzyloxy, 1,1-bis-trifluoromethyl-1-hydroxymethyl, trifluoromethylthio, and 3-trifluoromethylthiophenoxy;

$R_6$ is selected from the group consisting of fluoro and hydrido;

$R_7$ is selected from the group consisting of hydrido and fluoro.

In a preferred specific embodiment of compounds of Formulas I-WOPA and I-WOHA,

A is selected from the group consisting of ethyl, 1-propenyl, propyl, isopropyl, butyl, 2-butenyl, 3-butenyl, 2-butynyl, sec-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl, 6-octynyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-2-heptynyl, 1-methyl-3-heptynyl, 1-methyl-4-heptenyl, 1-methyl-5-heptenyl, 1-methyl-6-heptenyl, 1-methyl-2-heptenyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-propyl-2-pentynyl, 1-propyl-3-pentynyl, 1-butyl-2-butynyl, 1-butyl-3-butenyl, 2,2-difluoropropyl, 4-trifluoromethyl-5,5,5-trifluoropentyl, 4-trifluoromethylpentyl, 5,5,6,6,6-pentafluorohexyl, 3,3,3-trifluoropropyl, 2-methoxyethyl, 2-ethoxyethyl, 2-propoxyethyl, 2-isopropoxyethyl, 2-butoxyethyl, 2-isobutoxyethyl, 2-sec-butoxyethyl, 2-pentoxyethyl, 2-hexoxyethyl, 3-methoxypropyl, 2-methoxyisopropyl, 3-ethoxypropyl, 2-ethoxyisopropyl, 3-propoxypropyl, 2-propoxyisopropyl, 3-isopropoxypropyl, 2-isopropoxyisopropyl, 3-butoxypropyl, 2-butoxyisopropyl, 3-isobutoxypropyl, 2-isobutoxyisopropyl, 3-pentoxypropyl, and 2-pentoxyisopropyl, wherein each member of group A may be optionally substituted at any carbon up to and including 6 atoms from the point of attachment of A to Z with one or more of the group consisting of $R_{33}$, $R_{34}$, $R_{35}$, and $R_{36}$ with the provisos that $R_{33}$, $R_{34}$, $R_{35}$, and $R_{36}$ must not be attached to the carbon directly linking A to Z and that $R_{33}$, $R_{34}$, $R_{35}$, and $R_{36}$ must be selected from other than aryl and heteroaryl when substituting the carbon 2 atoms from Z wherein Z is a single covalent bond;

$R_{33}$, $R_{34}$, $R_{35}$, and $R_{36}$ are independently selected from the group consisting of cyano, hydroxy, 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio.

In a preferred specific embodiment of compounds of Formulas I-WOPA and I-WOHA,

A is selected from the group consisting of ethyl, 1-propenyl, propyl, isopropyl, butyl, 2-butenyl, 3-butenyl, sec-butyl, isobutyl, 2-methylpropenyl, 1-pentyl, 2-pentenyl, 3-pentenyl, 4-pentenyl, 2-pentyl, 1-methyl-2-butenyl, 1-methyl-3-butenyl, 3-pentyl, 1-ethyl-2-propenyl, 2-methylbutyl, 2-methyl-2-butenyl, 2-methyl-3-butenyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexyl, 1-methyl-2-pentenyl, 1-methyl-3-pentenyl, 1-methyl-4-pentenyl, 3-hexyl, 1-ethyl-2-butenyl, 1-ethyl-3-butenyl, 1-propyl-2-propenyl, 1-heptyl, 2-heptenyl, 3-heptenyl, 4-heptenyl, 5-heptenyl, 6-heptenyl, 2-heptyl, 1-methyl-2-hexenyl, 1-methyl-3-hexenyl, 1-methyl-4-hexenyl, 1-methyl-5-hexenyl, 3-heptyl, 1-ethyl-2-pentenyl, 1-ethyl-3-pentenyl, 1-ethyl-4-pentenyl, 1-butyl-2-propenyl, 1-octyl, 2-octenyl, 3-octenyl, 4-octenyl, 5-octenyl, 6-octenyl, 7-octenyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-4-heptenyl, 1-methyl-6-heptenyl, 1-methyl-2-heptenyl, 3-octyl, 1-ethyl-2-hexenyl, 1-ethyl-3-hexenyl, 1-ethyl-4-hexenyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-butyl-3-butenyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group A may be optionally substituted at any carbon up to and including 6 atoms from the point of attachment of A to Z with one or more of the group consisting of $R_{33}$, $R_{34}$, $R_{35}$, and $R_{36}$ with the provisos that $R_{33}$, $R_{34}$, $R_{35}$, and $R_{36}$ must not be attached to the carbon directly linking A to Z and that $R_{33}$, $R_{34}$, $R_{35}$, and $R_{36}$ must be selected from other than aryl and heteroaryl when substituting the carbon 2 atoms from Z wherein Z is a single covalent bond;

$R_{33}$, $R_{34}$, $R_{35}$, and $R_{36}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio.

In an even more preferred specific embodiment of compounds of Formulas I-WOPA and I-WOHA, A is selected from the group consisting of 1-propenyl, propyl, isopropyl, butyl, 2-butenyl, 3-butenyl, sec-butyl, isobutyl, 2-methylpropenyl, 1-pentyl, 2-pentenyl, 3-pentenyl, 4-pentenyl, 2-pentyl, 1-methyl-2-butenyl, 1-methyl-3-butenyl, 3-pentyl, 1-ethyl-2-propenyl, 2-methylbutyl, 2-methyl-2-butenyl, 2-methyl-3-butenyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexyl, 1-methyl-2-pentenyl, 1-methyl-3-pentenyl, 1-methyl-4-pentenyl, 3-hexyl, 1-ethyl-2-butenyl, 1-ethyl-3-butenyl, 1-propyl-2-propenyl, 1-ethyl-2-pentenyl, 1-ethyl-3-pentenyl, 1-ethyl-4-pentenyl, 1-butyl-2-propenyl, 1-ethyl-2-hexenyl, 1-ethyl-3-hexenyl, 1-ethyl-4-hexenyl, 1-ethyl-5-hexenyl, 1-pentyl-2-propenyl, 1-propyl-2-pentenyl, 1-propyl-3-pentenyl, 1-propyl-4-pentenyl, 1-butyl-2-butenyl, 1-butyl-3-butenyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group A may be optionally substituted at any carbon up to and including 6 atoms from the point of attachment of A to Z with one or more of the group consisting of $R_{33}$, $R_{34}$, $R_{35}$, and $R_{36}$ with the provisos that $R_{33}$, $R_{34}$, $R_{35}$, and $R_{36}$ must not be attached to the carbon directly linking A to Z and that $R_{33}$, $R_{34}$, $R_{35}$, and $R_{36}$ must be selected from other than aryl and heteroaryl when substituting the carbon 2 atoms from Z wherein Z is a single covalent bond;

$R_{33}$, $R_{34}$, $R_{35}$, and $R_{36}$ are independently selected from the group consisting of 5-bromo-2-fluorophenoxy, 4-chloro-3-ethylphenoxy, cyclopentyl, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 2-furyl, isobutyl, isopropoxy, 3-isopropylphenoxy, 3-methylphenoxy, pentafluoroethyl, 3-pentafluoroethylphenoxy, 3-tert-butylphenoxy, 1,1,2,2-tetrafluoroethoxy, 3-(1,1,2,2-tetrafluoroethoxy)phenoxy, 2-(5,6,7,8-tetrahydronaphthyloxy), trifluoromethoxy, 3-trifluoromethoxybenzyloxy, 3-trifluoromethoxyphenoxy, trifluoromethyl, 3-trifluoromethylbenzyloxy, 1,1-bis-trifluoromethyl-1-hydroxymethyl, trifluoromethylthio, and 3-trifluoromethylthiophenoxy.

In a preferred specific embodiment of compounds of Formulas I-WOHA and 1-WOHC.

$D_1$, $D_2$, $J_1$, $J_2$ and $K_1$ are independently selected from the group consisting of C, N, O, S and a covalent bond to form the group consisting of 2-thienyl, 3-thienyl, 2-furyl, 3-furyl, 2-pyrrolyl, 3-pyrrolyl, 2-imidazolyl 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5 isothiazolyl, 2-oxazolyl, 2-thiazolyl, 3-isoxazolyl, 5 isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5, triazin-2-yl, 1,2,4-triazin-3-yl, 1,2,4-triazin-5-yl, 1,2,4-triazin-6-yl, 1,2,3-triazin-4-yl, 1-indolizinyl, 7-indolizinyl, 1-isoquinolyl, and 2-quinolyl, wherein a ring carbon atom adjacent to the carbon atom at the point of attachment may be optionally substituted with $R_4$ or $R_8$, a ring carbon atom adjacent to the $R_4$ position and two atoms from the point of attachment may be substituted with $R_5$, a ring carbon atom adjacent to the $R_8$ position and two atoms from the point of attachment may be substituted with $R_7$, and a ring carbon atom three atoms from the point of attachment and adjacent to the $R_5$ and $R_7$ positions may be substituted with $R_6$.

In a more preferred specific embodiment of compounds of Formulas I-WOHA and I-WOHC, $D_1$, $D_2$, $J_1$, $J_2$ and $K_1$ are independently selected from the group consisting of C, N, O, S and a covalent bond to form the group consisting of 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1-indolizinyl, 7-indolizinyl, 1-isoquinolyl, and 2-quinolyl, wherein a ring carbon atom adjacent to the carbon atom at the point of attachment may be optionally substituted with $R_4$ or $R_8$, a ring carbon atom adjacent to the $R_4$ position and two atoms from the point of attachment may be substituted with $R_5$, a ring carbon atom adjacent to the $R_8$ position and two atoms from the point of attachment may be substituted with $R_7$. and a ring carbon atom three atoms from the point of attachment and adjacent to the $R_5$ and $R_7$ positions may be substituted with $R_6$.

In an even more preferred specific embodiment of compounds of Formulas I-WOHA and I-WOHC, $D_1$, $D_2$, $J_1$, $J_2$ and $K_1$ are independently selected from the group consisting of C, N, O, S and a covalent bond to form the group consisting of 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a ring carbon atom adjacent to the carbon atom at the point of attachment may be optionally substituted with $R_4$ or $R_8$, a ring carbon atom adjacent to the $R_4$ position and two atoms from the point of attachment may be substituted with $R_5$, a ring carbon atom adjacent to the $R_8$ position and two atoms from the point of attachment may be substituted with $R_7$, and a ring carbon atom three atoms from the point of attachment and adjacent to the $R_5$ and $R_7$ positions may be substituted with $R_6$.

In a preferred specific embodiment of compounds of Formulas I-WOPC and I-WOHC,

A is selected from the group consisting of cyclopropyl, cyclobutyl, cyclopentyl, cyclopent-2-enyl, cyclopent-3-enyl, cyclohexyl, 4-methylcyclohexyl, 4-chloro-3-ethylphenoxycyclohexyl, 3-trifluoromethoxyphenoxycyclohexyl, 3-trifluoromethylcyclohexyl, 4-trifluoromethylcyclohexyl, 3,5-bis-trifluoromethylcyclohexyl, adamantyl, 3-trifluoromethyladamantyl, norbornyl, 3-trifluoromethylnorbornyl, norbornenyl, 7-oxabicyclo[2.2.1]heptan-2-yl, bicyclo[3.1.0]hexan-6-yl, cyclohex-2-enyl, cyclohex-3-enyl, cycloheptyl, cyclohept-2-enyl, cyclohept-3-en-4-yl, cyclooctyl, cyclooct-2-enyl, cyclooct-3-enyl, cyclooctenyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 2H-2-pyranyl, 2H-3-pyranyl, 2H-4-pyranyl, 4H-2-pyranyl, 4H-3-pyranyl, 4H-4-pyranyl, 2H-pyran-2-one-3-yl, 2H-pyran-2-one-4-yl, 2H-pyran-2-one-5-yl, 4H-pyranone-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon may be optionally substituted with $R_{30}$, a ring carbon other than the ring carbon at the point of attachment of A to Z may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{32}$, and a ring carbon or nitrogen atom four atoms from the point of attachment and adjacent to the $R_{11}$ and $R_{32}$ positions may be substituted with $R_{31}$;

$R_9$ and $R_{13}$ are fluoro;

$R_{10}$ and $R_{12}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_{11}$, $R_{31}$, and $R_{32}$ are independently selected from the group consisting of chloro, fluoro, hydrido, pentafluoroethyl, 1,1,2,2-tetrafluoroethoxy, trifluoromethyl, and trifluoromethoxy;

$R_{30}$ is selected from the group consisting of chloro, ethoxy, ethyl, fluoro, heptafluoropropyl, 1,1,1,3,3,3-hexafluoropropyl, isobutyl, isobutoxy, isopropoxy, isopropyl, isopropylthio, methyl, propyl, pentafluoroethyl, 2,2,3,3,3-pentafluoropropyl, 1,1,3,3,3-pentafluoropropyl, 1,1,2,2,3-pentafluoropropyl, propoxy, sec-butyl, tert-butoxy, 1,1,2,2-tetrafluoroethoxy, 2,2,2-trifluoroethoxy, 2,2,2-trifluoroethyl, trifluoromethoxy, and trifluoromethyl.

In a more preferred specific embodiment of compounds of Formulas I-WOPC and I-WOHC, A is selected from the group consisting of cyclopropyl, cyclobutyl, cyclopentyl, cyclohexyl, 4-methylcyclohexyl, 4-chloro-3-ethylphenoxycyclohexyl, 3-trifluoromethoxyphenoxycyclohexyl, 3-trifluoromethylcyclohexyl, 4-trifluoromethylcyclohexyl, 3,5-bis-trifluoromethylcyclohexyl, adamantyl, 3-trifluoromethyladamantyl, norbornyl, 3-trifluoromethylnorbornyl, norbornenyl, 7-oxabicyclo[2.2.1]heptan-2-yl, bicyclo[3.1.0]hexan-6-yl, cycloheptyl, cyclooctyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon may be optionally substituted with $R_{30}$, a ring carbon other than the ring carbon at the point of attachment of A to Z may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{32}$, and a ring carbon or nitrogen atom four atoms from the point of attachment and adjacent to the $R_{11}$ and $R_{32}$ positions may be substituted with $R_{31}$;

$R_9$ and $R_{13}$ are fluoro;

$R_{10}$ and $R_{12}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazolyl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_{11}$, $R_{31}$, and $R_{32}$ are independently selected from the group consisting of chloro, fluoro, hydrido, pentafluoroethyl, 1,1,2,2-tetrafluoroethoxy, and trifluoromethyl;

$R_{30}$ is selected from the group consisting of chloro, ethyl, fluoro, heptafluoropropyl, 1,1,1,3,3,3-hexafluoropropyl, isobutyl, isopropyl, methyl, pentafluoroethyl, 2,2,3,3,3-pentafluoropropyl, 1,1,3,3,3-pentafluoropropyl, 1,1,2,2,3-pentafluoropropyl, propyl, sec-butyl, 1,1,2,2-tetrafluoroethoxy, 2,2,2-trifluoroethoxy, 2,2,2-trifluoroethyl, trifluoromethoxy, and trifluoromethyl.

In an even more preferred specific embodiment of compounds of Formulas I-WOPC and I-WOHC, A is selected from the group consisting of cyclopropyl, cyclobutyl, cyclopentyl, cyclohexyl, 4-methylcyclohexyl, 4-chloro-3-ethylphenoxycyclohexyl, 3-trifluoromethoxyphenoxycyclohexyl, 3-trifluoromethylcyclohexyl, 4-trifluoromethylcyclohexyl, 3,5-bis-trifluoromethylcyclohexyl, adamantyl, 3-trifluoromethyladamantyl, norbornyl, 3-trifluoromethylnorbornyl, norbornenyl, 7-oxabicyclo[2.2.1]heptan-2-yl, bicyclo[3.1.0]hexan-6-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein a ring carbon other than the ring carbon at the point of attachment of A to Z may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{32}$, and a ring carbon or nitrogen atom four atoms from the point of attachment and adjacent to the $R_{11}$ and $R_{32}$ positions may be substituted with $R_{31}$;

$R_9$ and $R_{13}$ are fluoro;

$R_{10}$ and $R_{12}$ are independently selected from the group consisting of 5-bromo-2-fluorophenoxy, 4-chloro-3-ethylphenoxy, cyclopentyl, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 2-furyl, isobutyl, isopropoxy, 3-isopropylphenoxy, 3-methylphenoxy, pentafluoroethyl, 3-pentafluoroethylphenoxy, 3-tert-butylphenoxy, 1,1,2,2-tetrafluoroethoxy, 3-(1,1,2,2-tetrafluoroethoxy)phenoxy, 2-(5,6,7,8-tetrahydronaphthyloxy), trifluoromethoxy, 3-trifluoromethoxybenzyloxy, 3-trifluoromethoxyphenoxy, trifluoromethyl, 3-trifluoromethylbenzyloxy, 1,1-bis-trifluoromethyl-1-hydroxymethyl, trifluoromethylthio, and 3-trifluoromethylthiophenoxy;

$R_{11}$, $R_{31}$ and $R_{32}$ are independently selected from the group consisting of chloro, fluoro, hydrido, pentafluoroethyl, 1,1,2,2-tetrafluoroethoxy, and trifluoromethyl.

Definitions

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrogen atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical (=CH—), or two hydrido radicals may be attached to a carbon atom to form a "methylene" ($—CH_2—$) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 about 10 carbon atoms and having attachment points for two or more covalent bonds. Examples of such radicals are methylene, ethylene, ethylidene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene ($CH_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydoxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "lower alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated and partially saturated heteroatom-containing ring-shaped radicals having from 5 through 15 ring members selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like.

The term "heteroaryl" embraces fully unsaturated heteroatom-containing ring-shaped aromatic radicals having from 5 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.: unsaturated 5 to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents as defined below. Preferred heterocyclic radicals include five to twelve membered fused or unfused radicals. Non-limiting examples of heteroaryl radicals include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, pyrazinyl, piperazinyl, 1,3,5-triazinyl, 1,3,5-trithianyl, benzo(b)thiophenyl, benzimidazoyl, quinolinyl, tetraazolyl, and the like.

The term "sulfonyl", whether used alone or linked to other terms such as alkylsulfonyl, denotes respectively divalent radicals —$SO_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above. The term "aminosulfonyl" denotes an amino radical attached to a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having from 3 through 15 carbon atoms. Cycloalkyl radicals may contain one, two, three, or four rings wherein such rings may be attached in a pendant manner or may be fused. Examples of cycloalkyl radicals having two or more rings include adamantyl, norbornyl, and 7-oxabicyclo[2.2.1]heptanyl. More preferred cycloalkyl radicals are "lower cycloalkyl" radicals having from 3 through 8 carbon atoms. Examples include radicals such as cyclopropyl, cyclobutyl, cyclopentyl, cyclohexyl and cycloheptyl. The term "cycloalkyl" also embraces radicals where cycloalkyl radicals are fused with aryl radicals or heterocyclyl radicals. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having from one through six carbon atoms. Examples of such radicals include cyclohexylhexyl. The term "cycloalkenyl" embraces radicals having three to fifteen carbon atoms and one or more carbon-carbon double bonds. Cycloalkenyl radicals may contain one, two, three, or four rings wherein such rings may be attached in a pendant manner or may be fused. Examples of cycloalkenyl radicals having two or more rings include norbornenyl. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy.

The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals. The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above.

"Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced, are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The terms alkylamino denotes "monoalkylamino" and "dialkylamino" containing one or two alkyl radicals, respectively, attached to an amino radical.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(═O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(═O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloroethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. Examples of such radicals include benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "lower heteroaralkoxy" radicals having heteroaryl radicals attached to lower alkoxy radical as described above.

The term "haloheteroaryloxyalkyl" embraces heteroaryloxyalkyl radicals, as defined above, wherein one to four halo radicals are attached to an heteroaryloxy group.

The term "heteroarylamino" embraces heterocyclyl radicals, as defined above, attached to an amino group. Examples of such radicals include pyridylamino.

The term "heteroarylaminoalkyl" embraces heteroarylamino radicals, as defined above, attached to an alkyl group. Examples of such radicals include pyridylmethylamino.

The term "heteroaryloxy" embraces heterocyclyl radicals, as defined above, attached to an oxy group. Examples of such radicals include 2-thiophenyloxy, 2-pyrimidyloxy, 2-pyridyloxy, 3-pyridyloxy, and 4-pyridyloxy.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl.

The term "arylthio" embraces aryl radicals, as defined above, attached to an sulfur atom. Examples of such radicals include phenylthio.

The term “arylthioalkyl” embraces arylthio radicals, as defined above, attached to an alkyl group. Examples of such radicals include phenylthiomethyl.

The term “alkylthioalkyl” embraces alkylthio radicals, as defined above, attached to an alkyl group. Examples of such radicals include methylthiomethyl. The term “alkoxyalkyl” embraces alkoxy radicals, as defined above, attached to an alkyl group. Examples of such radicals include methoxymethyl.

The term “carbonyl” denotes a carbon radical having two of the four covalent bonds shared with an oxygen atom. The term “carboxy” embraces a hydroxyl radical, as defined above, attached to one of two unshared bonds in a carbonyl group. The term “carboxamide” embraces amino, monoalkylamino, dialkylamino, monocycloalkylamino, alkylcycloalkylamino, and dicycloalkylamino radicals, attached to one of two unshared bonds in a carbonyl group. The term “carboxamidoalkyl” embraces carboxamide radicals, as defined above, attached to an alkyl group. The term “carboxyalkyl” embraces a carboxy radical, as defined above, attached to an alkyl group. The term “carboalkoxy” embraces alkoxy radicals, as defined above, attached to one of two unshared bonds in a carbonyl group. The term “carboaralkoxy” embraces aralkoxy radicals, as defined above, attached to one of two unshared bonds in a carbonyl group. The term “monocarboalkoxyalkyl” embraces one carboalkoxy radical, as defined above, attached to an alkyl group. The term “dicarboalkoxyalkyl” embraces two carboalkoxy radicals, as defined above, attached to an alkylene group. The term “monocyanoalkyl” embraces one cyano radical, as defined above, attached to an alkyl group. The term “dicyanoalkylene” embraces two cyano radicals, as defined above, attached to an alkyl group. The term “carboalkoxycyanoalkyl” embraces one cyano radical, as defined above, attached to an carboalkoxyalkyl group.

The term “acyl”, alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of “acyl” are formyl, acetyl, benzoyl, trifluoroacetyl, phthaloyl, malonyl, nicotinyl, and the like. The term “haloalkanoyl” embraces one or more halo radicals, as defined herein, attached to an alkanoyl radical as defined above. Examples of such radicals include, for example, chloroacetyl, trifluoroacetyl, bromopropanoyl, and heptafluorobutanoyl. The term “diacyl”, alone or in combination, means having two or more carbonyl or thionocarbonyl groups bonded to a radical selected from, for example, alkylene, alkenylene, alkynylene, haloalkylene, alkoxyalkylene, aryl, heterocyclyl, heteroaryl, aralkyl, cycloalkyl, cycloalkylalkyl, and cycloalkenyl. Examples of “diacyl” are phthaloyl, malonyl, succinyl, adipoyl, and the like.

The term “benzylidenyl” radical denotes substituted and unsubstituted benzyl groups having attachment points for two covalent bonds. One attachment point is through the methylene of the benzyl group with the other attachment point through an ortho carbon of the phenyl ring. The methylene group is designated for attached to the lowest numbered position. Examples include the base compound benzylidene of structure:

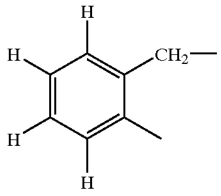

The term “phenoxylidenyl” radical denotes substituted and unsubstituted phenoxy groups having attachment points for two covalent bonds. One attachment point is through the oxy of the phenoxy group with the other attachment point through an ortho carbon of the phenyl ring. The oxy group is designated for attached to the lowest numbered position. Examples include the base compound phenoxylidene of structure:

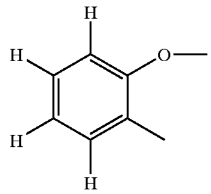

The term “phosphono” embraces a pentavalent phosphorus attached with two covalent bonds to an oxygen radical. The term “dialkoxyphosphono” denotes two alkoxy radicals, as defined above, attached to a phosphono radical with two covalent bonds. The term “diaralkoxyphosphono” denotes two aralkoxy radicals, as defined above, attached to a phosphono radical with two covalent bonds. The term “dialkoxyphosphonoalkyl” denotes dialkoxyphosphono radicals, as defined above, attached to an alkyl radical. The term “diaralkoxyphosphonoalkyl” denotes diaralkoxyphosphono radicals, as defined above, attached to an alkyl radical.

Said “alkyl”, “alkenyl”, “alkynyl”, “alkanoyl”, “alkylene”, “alkenylene”, “benzylidenyl”, “phenoxylidenyl”, “hydroxyalkyl”, “haloalkyl”, “haloalkylene”, “haloalkenyl”, “alkoxy”, “alkenyloxy”, “alkenyloxyalkyl”, “alkoxyalkyl”, “aryl”, “perhaloaryl”, “haloalkoxy”, “haloalkoxyalkyl”, “haloalkenyloxy”, “haloalkenyloxyalkyl”, “alkylenedioxy”, “haloalkylenedioxy”, “heterocyclyl”, “heteroaryl”, “hydroxyhaloalkyl”, “alkylsulfonyl”, “haloalkylsulfonyl”, “alkylsulfonylalkyl”, “haloalkylsulfonylalkyl”, “alkylsulfinyl”, “alkylsulfinylalkyl”, “haloalkylsulfinylalkyl”, “aralkyl”, “heteroaralkyl”, “perhaloaralkyl”, “aralkylsulfonyl”, “aralkylsulfonylalkyl”, “aralkylsulfinyl”, “aralkylsulfinylalkyl”, “cycloalkyl”, “cycloalkylalkanoyl”, “cycloalkylalkyl”, “cycloalkenyl”, “halocycloalkyl”, “halocycloalkenyl”, “cycloalkylsulfinyl”, “cycloalkylsulfinylalkyl”, “cycloalkylsulfonyl”, “cycloalkylsulfonylalkyl”, “cycloalkoxy”, “cycloalkoxyalkyl”, “cycloalkylalkoxy”, “cycloalkenyloxy”, “cycloalkenyloxyalkyl”, “cycloalkylenedioxy”, “halocycloalkoxy”, “halocycloalkoxyalkyl”, “halocycloalkenyloxy”, “halocycloalkenyloxyalkyl”, “alkylthio”, “haloalkylthio”, “alkylsulfinyl”, “amino”, “oxy”, “thio”, “alkylamino”, “arylamino”, “aralkylamino”, “arylsulfinyl”, “arylsulfinylalkyl”, “arylsulfonyl”, “arylsulfonylalkyl”, “heteroarylsulfinyl”, “heteroarylsulfinylalkyl”, “heteroarylsulfonyl”, “heteroarylsulfonylalkyl”, "heteroarylamino", "heteroarylaminoalkyl", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl" and "diacyl" groups defined above may optionally have 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocyeloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" may include a covalent bond, a linear moiety having a backbone of 1 to 7 continous atoms, and a branched moiety having three branches connecting to a common atom with a total of from 1 through 8 atoms. The spacer may have 1 to 7 atoms of a univalent or multi-valent chain. Univalent chains may be constituted by a radical selected from $=C(H)-$, $=C(R_{17})-$, $-O-$, $-S-$, $-S(O)-$, $-S(O)_2-$, $-NH-$, $-N(R_{17})-$, $-N=$, $-CH(OH)-$, $=C(OH)-$, $-CH(OR_{17})-$, $=C(OR_{17})-$, and $-C(O)-$ wherein $R_{17}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms, a straight chain of 1 or 2 or 3 or 4 or 5 or 6 atoms with a side chain, or a branched chain made up of 1 or 2 or 3 or 4 atoms in each of the three branches. The chain may be constituted of one or more radicals selected from: lower alkylene, lower alkenyl, $-O-$, $-O-CH_2-$, $-S-CH_2-$, $-CH_2CH_2-$, ethenyl, $-CH=CH(OH)-$, $-OCH_2O-$, $-O(CH_2)_2O-$, $-NHCH_2-$, $-OCH(R_{17})O-$, $-O(CH_2CHR_{17})O-$, $-OCF_2O-$, $-O(CF_2)_2O-$, $-S-$, $-S(O)-$, $-S(O)_2-$, $-N(H)-$, $-N(H)O-$, $-N(R_{17})O-$, $-N(R_{17})-$, $-C(O)-$, $-C(O)NH-$, $-C(O)NR_{17}-$, $-N=$, $-OCH_2-$, $-SCH_2-$, $S(O)CH_2-$, $-CH_2C(O)-$, $-CH(OH)-$, $=C(OH)-$, $-CH(OR_{17})-$, $=C(OR_{17})-$, $S(O)_2CH_2-$, and $-NR_{17}CH_2-$ and many other radicals defined above or generally known or ascertained by one of skill-in-the art. Side chains may include substituents such as 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C═O) and thiono (C═S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The following general synthetic sequences are useful in making the present invention. Abbreviations used in the schemes are as follows: "AA" represents amino acids, "BINAP" represents 2,2'-bis(diphenylphosphino)-1,1'-binaphthyl, "Boc" represents tert-butyloxycarbonyl, "BOP" represents benzotriazol-1-yl-oxy-tris-(dimethylamino), "bu" represents butyl, "dba" represents dibenzylideneacetone, "DCC" represents 1,3-dicyclohexylcarbodiimide, "DIBAH" represents diisobutylaluminum hydride, "DIPEA" represents diisopropylethylamine, "DMF" represents dimethylformamide, "DMSO" represents dimethylsulfoxide, "Fmoc" represents 9-fluorenylmethoxycarbonyl, "LDA" represents lithium diisopropylamide, "PHTH" represents a phthaloyl group, "pnZ" represents 4-nitrobenzyloxycarbonyl, "PFC" represents a phase transfer catalyst, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, and "Z" represents benzyloxycarbonyl.

Pharmaceutical Utility and Composition

The present invention comprises a pharmaceutical composition comprising a therapeutically-effective amount of a compound of Formulas VII-H, VII, VII-2, VII-3, VII-4, and Cyclo-VII, in association with at least one pharmaceutically-acceptable carrier, adjuvant or diluent.

The present invention also comprises a treatment and prophylaxis of coronary artery disease and other CETP-mediated disorders in a subject, comprising administering to the subject having such disorder a therapeutically-effective amount of a compound of Formula I-WA:

(I-WA)

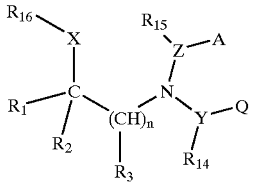

wherein $R_1$, $R_2$, $R_3$, n, $R_{14}$, $R_{15}$, $R_{16}$, A, Q, X, Y, and Z are as defined above for the compounds of Formula I-WA;

or a pharmaceutically-acceptable salt thereof.

As a further embodiment, compounds of the present invention of Formulas I-WA, I-WO, I-WOHA, I-WOPC, I-WOHA, and I-WOHC, or a pharmaceutically-acceptable salt thereof as defined above and further comprise a treatment and prophylaxis of coronary artery disease and other CETP-mediated disorders in a subject, comprising administering to the subject having such disorder a therapeutically-effective amount of compounds of Formulas I-WA, I-WO, I-WOHA, I-WOPC, I-WOHA, and I-WOHC, of the present invention or a pharmaceutically-acceptable salt thereof.

Compounds of Formulas I-WA, I-WO, I-WOHA, I-WOPC, I-WOHA, and I-WOHC are capable of inhibiting activity of cholesteryl ester transfer protein (CETP), and thus could be used in the manufacture of a medicament, a method for the prophylactic or therapeutic treatment of diseases mediated by CETP, such as peripheral vascular disease, hyperlipidaemia, hypercholesterolemia, and other diseases attributable to either high LDL and low HDL or a combination of both, or a procedure to study the mechanism of action of the cholesteryl ester transfer protein (CETP) to enable the design of better inhibitors. The compounds of Formulas I-WA, I-WO, I-WOHA, I-WOPC, I-WOHA, and I-WOHC would be also useful in prevention of cerebral vascular accident (CVA) or stroke.

Also included in the family of compounds of Formulas I-WA, I-WO, I-WOHA, I-WOPC, I-WOHA, and I-WOHC are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I-WA may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula I-WA include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compounds of Formulas I-WA, I-WO, I-WOHA, I-WOPC, I-WOHA, and I-WOHC by reacting, for example, the appropriate acid or base with the compounds of Formulas I-WA, I-WO, I-WOHA, I-WOPC, I-WOHA, and I-WOHC.

Also embraced within this invention is a class of pharmaceutical compositions comprising the active compounds of Formula I-WA in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

General Synthetic Procedures

The compounds of the present invention can be synthesized, for example, according to the following procedures of Schemes 1 through 14 below, wherein the substituents are as defined for Formulas I-WA, I-WO, I-WOHA, I-WOPC, I-WOHA, and I-WOHC above except where further noted.

Synthetic Scheme 1 shows the preparation of compounds of formula XIIIA-H ("Secondary Heteroaryl Amines") which are intermediates in the preparation of the compounds of the present invention corresponding to Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") wherein one substituent (A or Q) on the nitrogen is AQ-1 which can be independently selected from the group consisting of aryl and heteroaryl, which are preferably substituted with one or more groups, and another substituent (A or Q) on the nitrogen is AQ-2 which can be independently selected from the group consisting of AQ-2 and $—CH_2(CR_{37}R_{38})_v—(CR_{33}R_{34})_u—T—(CR_{35}R_{36})_w—H$. AQ-2 and $—CH_2(CR_{37}R_{38})_v—(CR_{33}R_{34})_u—T—(CR_{35}R_{36})_w—H$ can be independently selected from the group consisting of C3–C8 alkyl, C3–C8 alkenyl, C3–C8 alkynyl, C3–C8 haloalkyl, C3–C8 haloalkenyl, C3–C6 alkoxy C1–C2 alkyl, C3–C8 hydroxyhaloalkyl, C3–C10 cycloalkyl, C5–C10 cycloalkenyl, C4–C9 saturated heterocyclyl, and C4–C9 partially saturated heterocyclyl, wherein said group may be optionally substituted.

Schemes 1 through 14, taken together, prepare tertiary heteroalkylamine compounds of the present invention by addition of a halogenated, heteroatom (for example, oxygen, sulfur, or nitrogen) containing precursor to a resulting secondary amine to introduce a heteroatom containing alkyl group wherein one of the two groups making up the secondary amine is aromatic groups and the other is aliphatic (for example, C3–C8 alkyl, C3–C8 alkenyl, C3–C8 alkynyl, C3–C8 haloalkyl, C3–C8 haloalkenyl, C3–C6 alkoxy C1–C2 alkyl, C3–C8 hydroxyhaloalkyl, C3–C10 cycloalkyl, C5–C10 cycloalkenyl), C4–C9 saturated heterocyclyl, and C4–C9 partially saturated heterocyclyl.

The "Heteroaryl Imines" corresponding to Formulas XII-AH, CXII-AH, CKXII-AH can be prepared through dehydration techniques generally known in or adaptable from the art by reacting "Heteroaryl Amine" of Formula X-AH or a "Heteroaryl Carbonyl" of Formula XI-AH with a suitable an aliphatic, saturated heterocyclic, or partially saturated heterocyclic amine or carbonyl compound as shown in Schemes 1, 3, 4, 5, 6, 12, and subsequent specific examples. For example in Scheme 3, the two reactants (AQ-2A and XI-AH) react by refluxing them in an aprotic solvent, such as hexane, toluene, cyclohexane, benzene, and the like, using a Dean-Stark type trap to remove water. After about 2–8 hours or until the removal of water is complete, the aprotic solvent is removed in vacuo to yield the "Heteroaryl Imine" of Formula XII-AH.

The "Secondary Cyclic Heteroaryl Amines" of Formula XIIIA-H can be prepared from the corresponding "Generic Imine" of Formula XII, "Cyclic Heteroaryl Imine" of Formulas XII-AH, CXII-AH, and CKXII-AH can be prepared in several ways. For example, in one synthetic scheme (Reduction Method-1), the "Generic Imine" of Formula XII-AH is partially or completely dissolved in presence of a lower alcohol containing sufficient organic or mineral acid, as described in WO Patent Application No. 9738973, Swiss Patent CH 441366 and U.S. Pat. Nos. 3,359,316 and 3,334,017, which are incorporated herein by reference, and then hydrogenated at 0–100° C., more preferably 20–50° C., and most preferably between 20–30° C. and pressures of 10–200 psi hydrogen or more preferably between 50–70 psi hydrogen in the presence of a noble metal catalyst such as PtO2.

In another synthetic scheme (Reduction Method-2), the "Cyclic Heteroaryl Imine" of Formulas XII-AH, CXII-AH, and CKXII-AH is slurried in a lower alcohol such as ethanol, methanol or like solvent at 0–10° C. and solid sodium borohydride is added in batches over 5–10 minutes at 0–10° C. with stirring. The reaction mixture is stirred below 10° C. for 30–90 minutes and then is warmed gradually to 15–30° C. After about 1–10 hours, the mixture is cooled and acid is added until the aqueous layer was just acidic (pH 5–7).

In yet another synthetic scheme (Reduction Method-3), which is preferred when Z is an oxygen, the "Cyclic Heteroaryl Imine" of Formulas XII-AH, CXII-AH, and CKXII-AH is slurried in a lower alcohol solvent at 0–10° C. and acidified to a pH less than 4 and sodium cyanoborohydride is added in batches over 30–90 minutes at 0–20° C. with stirring and addition of a suitable organic or mineral acid to keep the pH at or below 4. The reaction mixture is stirred and warmed gradually to about 20–25° C. After about 1–10 hours, the mixture is cooled and base added until the mixture was just slightly alkaline.

The "Secondary Cyclic Heteroaryl Amines" of Formulas XIII-AH, CXIIIA-H, and CKXIII-AH can also be prepared, according to Schemes 1 and 3, by an alkylation procedure based on the nucleophilic substitution of bromides by amines. In one synthetic alkylation scheme (Alkylation Method-1), a "Cyclic Amine" of Formula AQ-2A or a "Generic Amine-I" of Formula X is reacted with a "Heteroaryl Bromide" of Formula XXI-AH or "Generic Bromide" of Formula XXI as described in Vogel's Textbook of Practical Organic Chemistry, Fifth Edition, 1989, pages 902 to 905 and references cited therein all of which are incorporated herein by reference. In an alternate synthetic alkylation scheme exemplified in Scheme 1, an "Amine" of Formula XXII is reacted with a "Heteroaryl Bromide" in a method employing palladium catalyzed carbon-nitrogen bond formation. Suitable procedures for this conversion are described in Wagaw and Buchwald, J. Org. Chem.(1996), 61, 7240–7241, Wolfe, Wagaw and Buchwald, J. Am. Chem. Soc. (1996), 118, 7215–7216, and Wolfe and Buchwald, Tetrahedron Letters (1997),38(36), 6359–6362 and references cited therein all of which are incorporated herein by reference.

The "Generic Secondary Amine", "Heteroaryl Amine", "Cyclic Amine", "Alicyclic Amine", and "Heteoaryl Hydroxylamine" amines and hydroxylamines, the "Generic Carbonyl", "Heteroaryl Carbonyl", "Cyclic Carbonyl", and "Cyclic Ketone" aldehydes and ketones, and "Generic Bromide-1", "Generic Bromide-2", "Heteroaryl Bromide", and the like halides, tosylates, mesylates, triflates, and precursor alcohols required to prepare the "Secondary Cyclic Heteroaryl Amine" compounds are available from commercial sources or can be prepared by one skilled in the art from published procedures. Commercial sources include but are not limited to Aldrich Chemical, TCI-America, Lancaster-Synthesis, Oakwood Products, Acros Organics, and Maybridge Chemical. Disclosed procedures for "Generic Amine" amines, hydroxylamines, and hydrazines include Sheradsky and Nov, J. Chem. Soc., Perkin Trans.1 (1980), (12), 2781–6; Marcoux, Doye, and Buchwald, J. Am. Chem. Soc. (1997), 119, 1053–9; Sternbach and Jamison, Tetrahedron Lett. (1981), 22(35), 3331–4; U.S. Pat. No. 5,306,718; EP No. 314435; WO No. 9001874; WO No. 9002113; JP No. 05320117; WO No. 9738973; Swiss Patent No. CH 441366; U.S. Pat. Nos. 3,359,316 and 3,334,017; and references cited therein which are incorporated herein by reference.

Synthetic Schemes 2, 10 and 11 show the preparation of the class of compounds of the present invention corresponding to Formula I-WO ("Alicyclic/Cyclic Aryl/Heteroaryl Aminoalcohols") and Formula I-WA ("Alicyclic/Cyclic Aryl/Heteroaryl tertiary Heteroalkylamines").

Derivatives of "Alicyclic/Cyclic Aryl/Heteroaryl Aminoalcohols" or "Alicyclic/Cyclic Aryl/Heteroaryl tertiary Heteroalkylamines", in which the heteroatom (O, N, or S) is attached to an alkyl group removed from the amine by two or more carbons are readily prepared by anion chemistry using the method of Scheme 2. The anion of "Secondary Amine" amines and hydroxylamines of Formula XIII are readily formed by dissolving the specific amine, hydroxylamine, or hydrazine in an aprotic solvent, such as tetrahydrofuran, toluene, ether, dimethylformamide, and dimethylformamide, under anhydrous conditions. The solution is cooled to a temperature between −78 and 0° C., preferably between −78 and −60° C. and the anion formed by the addition of at least one equivalent of a strong, aprotic, non-nucleophillic base such as NaH or n-butyllithium under an inert atmosphere for each acidic group present. Maintaining the temperature between −78 and 0° C., preferably between −78 and −60° C., with suitable cooling, an appropriate alkyl halide, alkyl benzenesulfonate such as a alkyl tosylate, alkyl mesylate, alkyl triflate or similar alkylating reagent of the general structure:

(XXX)

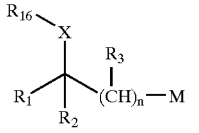

where m is zero, X can be RN, O, and S, and M is a readily displaceable group such as chloride, bromide, iodide, tosylate, triflate, and mesylate. After allowing the reaction mixture to warm to room temperature, the reaction product is added to water, neutralized if necessary, and extracted with a water-immiscible solvent such as diethyl ether or methylene chloride. The combined aprotic solvent extract is washed with saturated brine, dried over drying agent such as anhydrous $MgSO_4$ and concentrated in vacuo to yield crude Formula I-WO ("Alicyclic/Cyclic Aryl/Heteroaryl Aminoalcohols") and Formula I-WA ("Alicyclic/Cyclic Aryl/Heteroaryl tertiary Heteroalkylamines"). This material is purified, for example, by eluting through silica gel with a medium polar solvent such as ethyl acetate in a non-polar solvent such as hexanes to yield purified Formula I-WA and Formula I-WO. Products are structurally confirmed by low and high resolution mass spectrometry and NMR.

Compounds of Formula (XXX), which can be used to prepare I-WA, I-WO, I-WOPA, I-WOPC, I-WOHA, and I-WOHC, are given in Table 2. Reagents 1a and 2a in Table 2 are prepared from the corresponding alcohols. The tosylates are readily obtained by reacting the corresponding alcohol with tosyl chloride using procedures found in House's Modern Synthetic Reactions, Chapter 7, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons, which are incorporated herein by reference.

A preferred procedure for Formula I-WO ("Alicyclic/Cyclic Aryl/Heteroaryl Aminoalcohols") and Formula I-WA ("Alicyclic/Cyclic Aryl/Heteroaryl tertiary Heteroalkylamines" compounds is Method A of Schemes 2, 10, 11, and 14. Oxirane reagents useful in Method A are exemplified, but not limited to those in Table 1. Formula I-WO ("Alicyclic/Cyclic Aryl/Heteroaryl 1-Amino-2-alcohol") and Formula I-WA ("Alicyclic/Cyclic Aryl/Heteroaryl tertiary 2-Heteroalkylamine") compounds are prepared by using "Secondary Cyclic Heteroaryl Amine" and "Alicyclic Heteroaryl Amine" amines and hydroxylamines of Formulas XIIIA-H, CXIIIA-H, CKXIII-AH, ACXIIIA-H, and RACXIIIA-H prepared above with oxiranes of the type listed in Table 1 and represented by the general structure:

(XX)

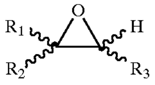

In some cases, the oxiranes are prepared by reaction of epoxidation reagents such as MCPBA and similar type reagents readily selectable by a person of skill-in-the-art with alkenes. Fieser and Fieser in Reagents for Organic Synthesis, John Wiley & Sons provides, along with cited references, numerous suitable epoxidation reagents and reaction conditions, which are incorporated herein by reference.

Formula I-WA ("Alicyclic/Cyclic Aryl/Heteroaryl tertiary 2-Heteroalkylamine") compounds, wherein the 2-hetero group is an amino, substituted amino, or thiol, can be prepared by using appropriate aziridines and thirranes according to Method A of Scheme 2. Aziridine and thiirane reagents useful in Method A are exemplified, but not limited to those in Table 1. These Formula I-WA ("Alicyclic/Cyclic Aryl/Heteroaryl tertiary 2-Heteroalkylamine") compounds, wherein the 2-hetero group is an amino, substituted amino, or thiol, can be prepared by using "Secondary Cyclic Heteroaryl Amine" and "Alicyclic Heteroaryl Amine" amines and hydroxylamines of Formulas XIIIA-H, CXIIIA-H, CKXIII-AH, ACXIIIA-H, and RACXIIIA-H prepared above with aziridines and thiiranes of the type listed in Table 1 and represented by the general structure:

(XX)

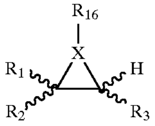

wherein X is selected from N and S and $R_{16}$ is hydrogen or another suitable group when X is N.

TABLE 1

Structure of Oxirane, Aziridine, and Thiirane Reagents.

(XX)

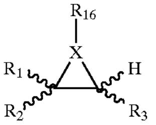

| Rgnt No. | $R_{16}$ | X | $R_1$ | $R_2$ | $R_3$ |
|---|---|---|---|---|---|
| 1 | — | O | $CF_3$ | H | H |
| 2 | — | O | $CCl_3$ | H | H |
| 3 | — | O | $CF_3$ | $CH_3$ | H |
| 4 | — | O | $CF_3CF_2$ | H | H |

TABLE 1-continued

Structure of Oxirane, Aziridine, and Thiirane Reagents.

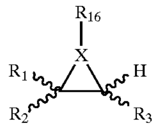

(XX)

| Rgnt No. | $R_{16}$ | X | $R_1$ | $R_2$ | $R_3$ |
|---|---|---|---|---|---|
| 5 | — | O | $CF_3CF_2CF_2$ | H | H |
| 6 | — | O | $CF_3OCF_2CF_2$ | H | H |
| 7 | — | O | $CF_3CH_2$ | H | H |
| 8 | — | O | $CF_3$ | $CHF_2$ | H |
| 9 | — | O | $CF_3$ | H | $CF_3$ |
| 10 | — | O | $CF_3$ | $CF_3$ | H |
| 11 | — | O | $CF_3$ | $C_6H_5$ | H |
| 12 | — | O | $CCl_3$ | $C_6H_5$ | H |
| 13 | — | O | $CCl_3$ | Cyclopropyl | H |
| 14 | — | O | $CCl_3$ | $CH_3$ | H |
| 15 | — | O | $CCl_3$ | $(CH_3)_2CH$ | H |
| 16 | — | O | $CHCl_2$ | H | H |
| 17 | — | O | $CHCl_2$ | Cl | H |
| 18 | — | O | $CF_3$ | H | $CH_3$ |
| 19 | H | N | $CF_3$ | $CF_3$ | H |
| 20 | H | N | $CF_3$ | H | H |
| 21 | Benzyl | N | $CF_3$ | H | H |
| 22 | $CH_3O$ | N | $CF_3$ | H | H |
| 23 | $CH_3$ | N | $CF_3$ | H | H |
| 24 | Benzyloxy | N | $CF_3$ | H | H |
| 25 | — | S | $CF_3$ | H | H |
| 26 | — | S | $CF_3CF_2$ | H | H |
| 27 | — | O | $CCl_3CH_2$ | H | H |
| 28 | — | O | $CBr_3CH_2$ | H | H |
| 29 | — | O | $CHBr_2CH_2$ | H | H |
| 30 | — | O | $CBrCl_2$ | H | H |
| 31 | — | O | $CClF_2$ | H | H |
| 32 | — | O | $CCl_2F$ | H | H |
| 33 | — | O | $CCl_3CCl_2$ | H | H |
| 43 | — | O | $FCH_2$ | H | H |
| 46 | — | O | $CF_3$ | $R_2 + R_3 = (CH_2)_3$ | |
| 47 | — | O | $CF_3$ | $R_2 + R_3 = (CH_2)_4$ | |
| 48 | — | O | $CHF_2$ | $R_2 + R_3 = (CH_2)_4$ | |
| 56 | — | O | $CBrF_2CClFCH_2$ | H | H |
| 57 | — | O | $HCF_2CF_2OCH_2$ | H | H |

TABLE 2

Structure and Source of Alcohol and Glycol Reagents.

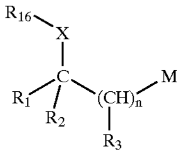

(XXX)

| Reagent Number | $R_1$ | n | M | $R_2$ | $R_3$ | X-$R_{16}$ | Source of Reagent |
|---|---|---|---|---|---|---|---|
| 1A | $CF_3$ | 3 | OTs | H | H | OH | Chiral separation and then tosylation of alcohol from Justus Liebigs Ann. Chem. (1969), 720, 81–97. |
| 2A | $CF_3CH_2CH_2$ | 3 | OTs | H | H | OH | Chiral separation and then tosylation of alcohol from Z. Naturforsch., B: Chem. Sci. (1997), 52 (3). 413–418 |

A mixture of a "Secondary Amine" amine or hydroxylamine and an oxirane of Formula XX are stirred and heated to 40–90° C. for 5 to 48 hours in a tightly capped or contained reaction vessel. A Lewis acid such as ytterbium triflate in acetonitrile may be added to speed up reaction and improve yield. When a Lewis acid is used, the reaction should be carried out under inert, anhydrous conditions using a blanket of dry nitrogen or argon gas. After cooling to room temperature and testing the reaction mixture for complete reaction by thin layer chromatography or high pressure liquid chromatography (hplc), the reaction product is added to water and extracted with a water immiscible solvent such as diethyl ether or methylene chloride. (Note: If the above analysis indicates that reaction is incomplete, heating should be resumed until complete with the optional addition of more of the oxirane). The combined aprotic solvent extract is washed with saturated brine, dried over drying agent such as anhydrous $MgSO_4$ and concentrated in vacuo to yield crude Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds. This material is purified by eluting through silica gel with 5–40% of a medium polar solvent such as ethyl acetate in a non-polar solvent such as hexanes to yield the Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds. Products are tested for purity by HPLC. If necessary, the Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds are purified by additional chromatography or recrystallization. Products are structurally confirmed by low and high resolution mass spectrometry and NMR. Examples of specific Formula VII Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") prepared are summarized in the Examples and Example Tables 1 through 7.

Specific Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") analogs of the Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds summarized in the Examples and Example Tables 1 through 7, wherein the hydroxyl or oxy group are replaced with an amino, substituted amino, aza, or thiol, can be prepared by using the appropriate aziridine reagents or thiirane reagents readily by adapting the procedures in the numerous specific Examples and Schemes disclosed in the present invention. Similarly, intermediates, in which the hydroxyl or oxy group of said intermediates are replaced with an amino, substituted amino, aza, or thiol, can be converted using the numerous specific Examples and Schemes disclosed in the present invention to other Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds.

Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds can further be prepared in an alternate manner to procedures disclosed above and in Schemes 1, 2, and 3. Schemes 12 and 13 detail such procedures to prepare compounds of the present invention by initial formation of an halogenated, oxygen containing primary alkylamine XL ("Generic Substituted Alkylamine"). Said halogenated, oxygen containing primary alkylamine XL, formed in Scheme 12, is itself converted to secondary amine LX-H ("Heteroaryl Alkyl Amine) using procedures disclosed above. Primary alkylamine XL is first reacted with an aldehydic or ketonic carbonyl compound, XI-AH ("Heteroaryl Carbonyl") with azeotropic distillation to form imines, L-H ("Heteroaryl Imine"). Said imine L-H are then reduced with or without prior isolation by Reduction Methods 1, 2 or 3 as disclosed above and in Scheme I to yield secondary amines LX-H ("Heteroaryl Alkyl Amine). Said secondary amine LX-H can be converted according to Scheme 14 to Formula I-WO ("Alicyclic/Cyclic Aryl/Heteroaryl Aminoalcohols").

Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds can further be prepared in an alternate manner to procedures disclosed above and in additional Schemes.

Formula I-WO ("Alicyclic/Cyclic Aryl/Heteroaryl Aminoalcohols") are alternately referred to as Formula I-WO ("Alicyclic/Cyclic Aryl/Heteroaryl 2-hydroxyalkylamines").

Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds can themselves serve as intermediates for conversion to additional compounds of this invention. Compounds of the present invention useful as intermediates include those in which the $R_5$ or $R_7$ position substituent in Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") compounds is a bromo group, hydroxyl-group, sulfhydryl group, bromomethyl or other bromoalkyl groups, nitro group, amino group, methoxy carbonyl or other alkoxy carbonyl groups, cyano group, or acyl groups. Other preferred compounds of the present invention useful as intermediates include those in which the $R_{10}$ position substituent in Formulas I-WA or I-WO is a bromo group, hydroxyl group, sulfhydryl group, bromomethyl or other bromoalkyl groups, nitro group, amino group, methoxy carbonyl or other alkoxy carbonyl groups, cyano group, or acyl groups. Other compounds of Formulas I-WA or I-WO and the present invention useful as intermediates include those in which one or more of $R_6$, $R_{11}$, and $R_{12}$ substituents in Formulas I-WA or I-WO is a bromo group, hydroxyl group, sulfhydryl group, bromomethyl or other bromoalkyl groups, nitro group, amino group, methoxy carbonyl or other alkoxy carbonyl groups, cyano group, or acyl groups.

Formula I-WO ("Alicyclic/Cyclic Aryl/Heteroaryl Aminoalcohols") are alternately referred to as Formula I-WO ("Alicyclic/Cyclic Aryl/Heteroaryl Tertiary 2-hydroxyalkylamines").

A 3-bromo substituent at the $R_5$ position in Formula I-WO ("Alicyclic/Cyclic 3-Bromoaryl Tertiary 2-Hydroxyalkylamines") can be reacted with a phenol to afford 3-phenoxy compounds of the present invention of Formula I-WO ("Alicyclic/Cyclic 3-Phenoxyaryl Tertiary 2-Hydroxyalkylamines").

A 3-bromo substituent at the $R_5$ position in Formula I-WO ("Alicyclic/Cyclic 3-Bromoheteroaryl Tertiary 2-hydroxyalkylamine") can, be reacted, for example, with a phenol to afford additional compounds of the present invention of Formula I-WO ("Alicyclic/Cyclic 3-Aryloxyaryl, 3-Heteroaryloxyaryl, 3-Heteroaryloxyheteroaryl, and 3-Aryloxyheteroaryl Tertiary 2-Hydroxyalkylamines").

A 3-bromo substituent at the $R_5$ position in Formula I-WO ("Alicyclic/Cyclic 3-Bromoaryl Tertiary 2-hydroxyalkylamine") can be reacted with a phenol to afford additional compounds of the present invention of Formula I-WO ("Alicyclic/Cyclic 3-Phenylaryl Tertiary 2-Hydroxyalkylamine").

Conversion of a 3-bromo substituent at the $R_5$ position in Formula I-WO ("Alicyclic/Cyclic 3-Bromoaryl Tertiary 2-hydroxyalkylamine") by reaction with a primary or secondary amine can afford additional compounds of the present invention of Formula I-WO ("Alicyclic/Cyclic 3-$R_{22}$aminoaryl Tertiary 2-Hydroxyalkylamine").

Conversion of a 3-bromo substituent at the $R_5$ position in Formula I-WO ("Alicyclic/Cyclic 3-Bromoaryl Tertiary 2-hydroxyalkylamine") by reaction with an aryl borinate can afford additional compounds of the present invention of Formula I-WO ("Alicyclic/Cyclic 3-Phenylaryl Tertiary 2-Hydroxyalkylamine").

Conversion of a 3-bromo substituent at the $R_5$ position in Formula I-WO ("Alicyclic/Cyclic 3-Bromoaryl Tertiary 2-hydroxyalkylamine") by reaction with a heteroaryl dibutyl tin compound can afford additional compounds of the present invention of Formula I-WO ("Alicyclic/Cyclic 3-Heteroarylaryl Tertiary 2-Hydroxyalkylamine").

Conversion of a 3-bromomethyl substituent at the $R_5$ position in Formula I-WO ("Alicyclic/Cyclic 3-Bromomethylaryl Tertiary 2-hydroxyalkylamine") by reaction with an aryl borinate can afford additional compounds of the present invention of Formula I-WO ("Alicyclic/Cyclic 3-Arylmethylaryl Tertiary 2-Hydroxyalkylamine").

Conversion of a 3-hydroxyl substituent at the $R_5$ position in Formula I-WO ("Alicyclic/Cyclic 3-Hydroxyheteroaryl Tertiary 2-hydroxyalkylamine") by reaction with an aryl bromide or heteroaryl bromide can afford additional compounds of the present invention of Formula I-WO ("Alicyclic/Cyclic 3-Aryloxyaryl, 3-Heteroaryloxyaryl, 3-Heteroaryloxyheteroaryl, and 3-Aryloxyheteroaryl Tertiary 2-Hydroxyalkylamines").

Conversion of a 3-hydroxyl substituent at the $R_5$ position in Formula I-WO ("Alicyclic/Cyclic 3-Hydroxyaryl Tertiary 2-hydroxyalkylamine") by reaction with an aryl bromide can afford additional compounds of the present invention of Formula I-WO ("Alicyclic/Cyclic 3-Phenoxyaryl Tertiary 2-Hydroxyalkylamine").

Conversion of a 3-hydroxyl substituent at the $R_5$ position in Formula I-WO ("Alicyclic/Cyclic 3-Hydroxyheteroaryl Tertiary 2-hydroxyalkylamine") by reaction with an aralkyl bromide or heteroaralkyl bromide can afford additional compounds of the present invention of Formula I-WO ("Alicyclic/Cyclic 3-Aralkyloxyaryl, 3-Heteroaralkyloxyaryl, 3-Heteroaralkyloxyheteroaryl, and 3-Aralkyloxyheteroaryl Tertiary 2-Hydroxyalkylamines").

Conversion of a 3-hydroxyl substituent at the $R_5$ position in Formula I-WO ("Alicyclic/Cyclic 3-Hydroxyaryl Tertiary 2-hydroxyalkylamine") by reaction with an aralkyl bromide can afford additional compounds of the present invention of Formula I-WO ("Alicyclic/Cyclic 3-Aralkyloxyaryl Tertiary 2-Hydroxyalkylamine").

Conversion of a 3-hydroxyl substituent at the $R_5$ position in Formula I-WO ("Alicyclic/Cyclic Polycyclic 3-Hydroxyaryl Tertiary 2-hydroxyalkylamine") by reaction with a displaceable organo bromide can afford additional compounds of the present invention of Formula I-WO ("Alicyclic/Cyclic 3-Organooxyaryl Tertiary 2-Hydroxyalkylamine").

Conversion of a 3-thio substituent at the $R_5$ position in Formula I-WO ("Alicyclic/Cyclic 3-thioaryl Tertiary 2-hydroxyalkylamine") by reaction with a displaceable organo bromide can afford additional compounds of the present invention of Formula 1-WO ("Alicyclic/Cyclic 3-Organothiaaryl Tertiary 2-Hydroxyalkylamine"). "Alicyclic/Cyclic 3-Organothiaaryl Tertiary 2-Hydroxyalkylamines" can be oxidized to sulfonyl compounds of 3-Organosulfonylaryl Tertiary 2-Hydroxyalkylamine").

Conversion of a 3-nitro substituent at the $R_5$ position in Formula I-WO ("Alicyclic/Cyclic 3-Nitroaryl Tertiary 2-hydroxyalkylamine") by hydrogenation can afford additional compounds of the present invention of Formula I-WO ("Alicyclic/Cyclic 3-Aminoaryl Tertiary 2-Hydroxyalkylamine"). Formula I-WO ("Alicyclic/Cyclic 3-Aminoaryl Tertiary 2-Hydroxyalkylamines") can be acylated to acyl amide compounds of Formula I-WO ("Alicyclic/Cyclic 3-Acylaminoaryl Tertiary 2-Hydroxyalkylamine").

Conversion of a 3-amino substituent at the $R_5$ position in Formula I-WO ("Alicyclic/Cyclic 3-Aminoaryl Tertiary 2-hydroxyalkylamine") by reaction with carbonyl compounds can afford additional compounds of the present invention of Formula I-WO ("Alicyclic/Cyclic 3-(Saturated Nitrogen Heterocycl-1yl)aryl Tertiary 2-Hydroxyalkylamine" and "Alicyclic/Cyclic 3-(Unsaturated Nitrogen Heterocycl-1yl)aryl Tertiary 2-Hydroxyalkylamine").

Conversion of a 3-methoxycarbonyl substituent at the $R_5$ position in Formula I-WO ("Alicyclic/Cyclic 3-Carbomethoxyaryl Tertiary 2-hydroxyalkylamine") by reaction with amination reagents can afford additional compounds of the present invention of Formula I-WO ("Alicyclic/Cyclic 3-Carboxamidoaryl Tertiary 2-Hydroxyalkylamine").

Conversion of a 3-cyano substituent at the $R_5$ position in Formula I-WO ("Alicyclic/Cyclic 3-Cyanoaryl Tertiary 2-hydroxyalkylamine") by reaction with organometallic reagents can afford additional compounds of the present invention of Formula I-WO ("Alicyclic/Cyclic 3-Acylaryl Tertiary 2-Hydroxyalkylamine"). Said "Alicyclic/Cyclic 3-Acylaryl Tertiary 2-Hydroxyalkylamines", can be reduced to hydroxyl compounds of Formula I-WO ("Alicyclic/Cyclic 3-Hydroxysubstitutedmethylaryl Tertiary 2-Hydroxyalkylamine").

Conversion of a 3-methoxycarbonyl substituent at the $R_{10}$ position in Formula I-WO ("Alicyclic/Cyclic 3-Carbomethoxyaryl Tertiary 2-hydroxyalkylamine") by reaction with amination reagents can afford additional compounds of the present invention of Formula I-WO ("Alicyclic/Cyclic 3-Carboxamidoaryl Tertiary 2-Hydroxyalkylamine").

Conversion of a 3-methoxycarbonyl substituent at the $R_{10}$ position in Formula I-WO ("Alicyclic/Cyclic 3-Carbomethoxyaryl Tertiary 2-hydroxyalkylamine") by reaction with an organometallic reagent can afford additional compounds of the present invention of Formula I-WO ("Alicyclic/Cyclic 3-(bis-Organohydroxymethyl)aryl Tertiary 2-Hydroxyalkylamine").

Conversion of a 3-methoxycarbonyl substituent at the $R_{10}$ position in Formula I-WO ("Alicyclic/Cyclic 3-Carbomethoxyaryl Tertiary 2-hydroxyalkylamine") by reaction with lithium aluminum hydride can afford additional compounds of the present invention of Formula I-WO ("Alicyclic/Cyclic 3-Hydroxymethylaryl Tertiary 2-Hydroxyalkylamine").

Conversion of a 3-methoxycarbonyl substituent at the $R_{10}$ position in Formula I-WO ("Alicyclic/Cyclic 3-Carbomethoxyaryl Tertiary 2-hydroxyalkylamine") by reaction with an alkylation reagent can afford additional compounds of the present invention of Formula I-WO ("Alicyclic/Cyclic 3-(bis-Organo-hydroxymethyl)aryl Tertiary 2-Hydroxyalkylamine").

Conversion of a 3-methoxycarbonyl substituent at the $R_{10}$ position in Formula I-WO ("Alicyclic/Cyclic 3-Carbomethoxyaryl Tertiary 2-hydroxyalkylamine") by reaction intially with an amidation reagent and then an organometallic reagent can afford additional compounds of the present invention of Formula I-WO ("Alicyclic/Cyclic 3-(Organo-carbonyl)aryl Tertiary 2-Hydroxyalkylamine").

Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") and other compounds of this invention poss-sessing hydroxyl, thiol, and amine functional groups can be converted to a wide variety derivatives. The hydroxyl group X, wherein $R_{16}$ is a hydrogen, of compounds of the present invention can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. In like manner, compounds that have at least one hydroxyl group present in the form of an alcohol or phenol can be acylated to its corresponding esters. Similarly, carbamic acid esters (urethans) can be obtained by reacting any hydroxyl group with isocyanates and carbamoyl chlorides. Sulfonate, phosphonate, and phosphate esters can be prepared using the corresponding acid chloride and similar reagents. Compounds that have at least one thiol group present can be converted to the corresponding thioesters derivatives analogous to those of alcohols and phenols using the same reagents and comparable reaction conditions. Compounds of Formulas I-WA, I-WO, and other compounds of the present invention that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley &

Sons. Reagents of a wide variety that can be used to derivatize hydroxyl, thiol, and amines of compounds of Formulas I-WA, I-WO, and other compounds of the present invention are available from commerical sources or the references cited above, which are incorporated herein by reference.

Formula I-WO ("Alicyclic/Cyclic Aryl/Heteroaryl Aminoalcohols") and Formula I-WA ("Alicyclic/Cyclic Aryl/Heteroaryl tertiary Heteroalkylamines") and other compounds of this invention possessing hydroxyl, thiol, and amine functional groups can be alkylated to a wide variety derivatives. The hydroxyl group X, wherein $R_{16}$ is a hydrogen, of compounds of Formulas I-WA, I-WO, and other compounds of the present invention can be readily converted to ethers. Alkylation to form an ether is readily effected using a suitable alkylating reagent such as an alkyl bromide, alkyl iodide or alkyl sulfonate.

The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents, amine catalyst such as pyridine in an inert solvent. In like manner, compounds of Formulas I-WA, I-WO, and the like that have at least one hydroxyl group present in the form of an alcohol or phenol can be alkylated to their corresponding ethers. Compounds of Formulas I-WA, I-WO, and other compounds that have at least one thiol group present can be converted to the corresponding thioether derivatives analogous to those of alcohols and phenols using the same reagents and comparable reaction conditions. Compounds of Formulas I-WA, I-WO, and other compounds that have at least one primary, secondary or tertiary amine group present can be converted to the corresponding quaternary ammonium derivatives. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Tertiary amines can be prepared from the corresponding primary or secondary amine by reductive alkylation with aldehydes and ketones using reduction methods 1, 2, or 3 as shown in Scheme 1. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formulas I-WA, I-WO, and the like are available from commerical sources or the references cited above, which are incorporated herein by reference.

The following examples are provided to illustrate the present invention and are not intended to limit the scope thereof. Those skilled in the art will readily understand that known variations of the conditions and processes of the following preparative procedures can be used to prepare these compounds.

Scheme 1

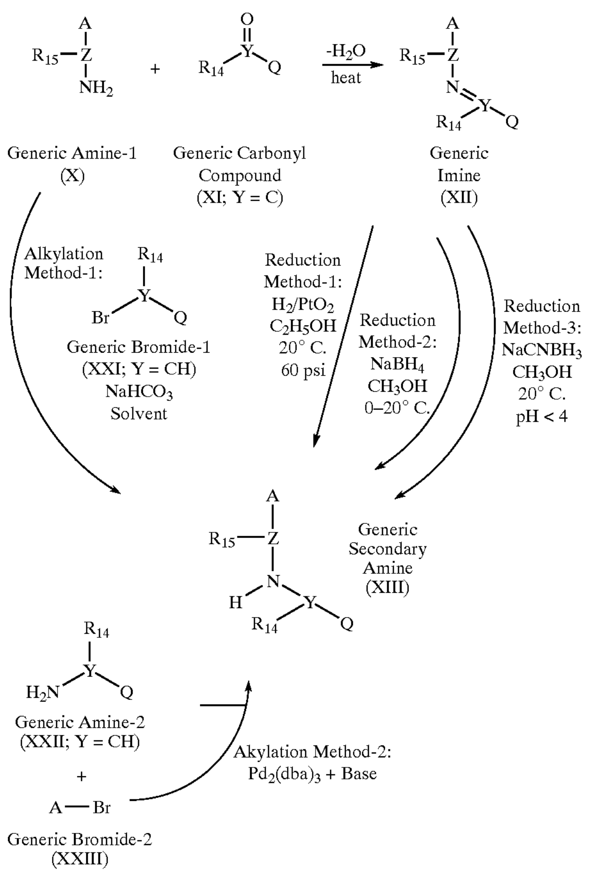

Scheme 2

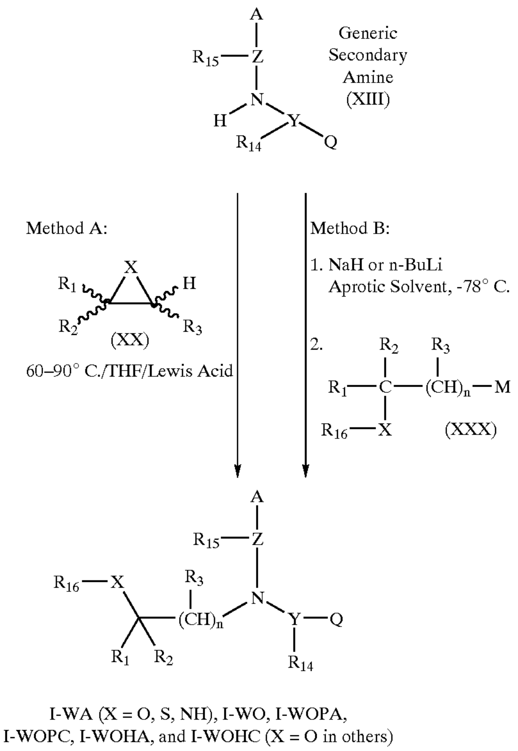

I-WA (X = O, S, NH), I-WO, I-WOPA, I-WOPC, I-WOHA, and I-WOHC (X = O in others)

Scheme 3
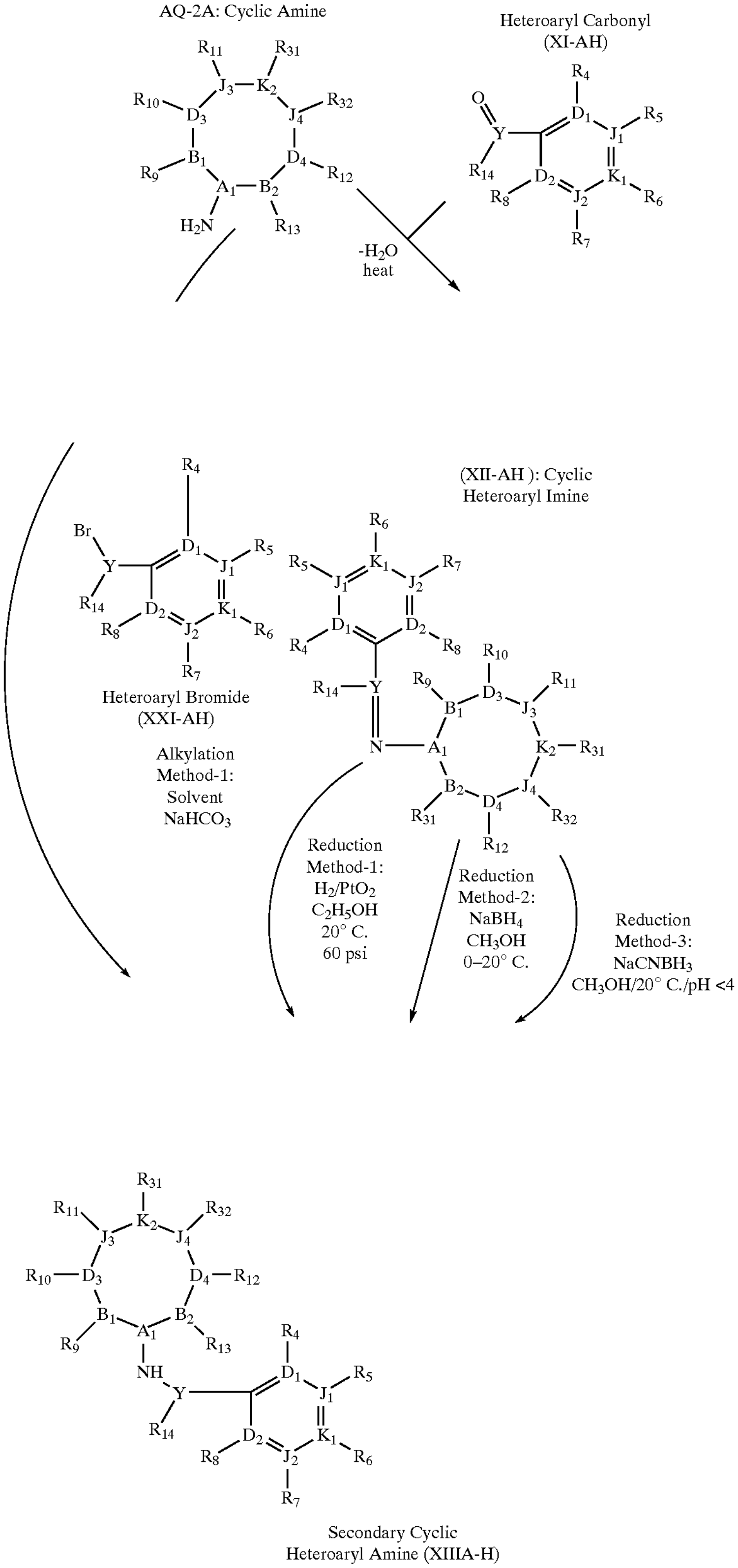
AQ-2A: Cyclic Amine
Heteroaryl Carbonyl (XI-AH)
Heteroaryl Bromide (XXI-AH)
(XII-AH): Cyclic Heteroaryl Imine
Secondary Cyclic Heteroaryl Amine (XIIIA-H)

Scheme 4
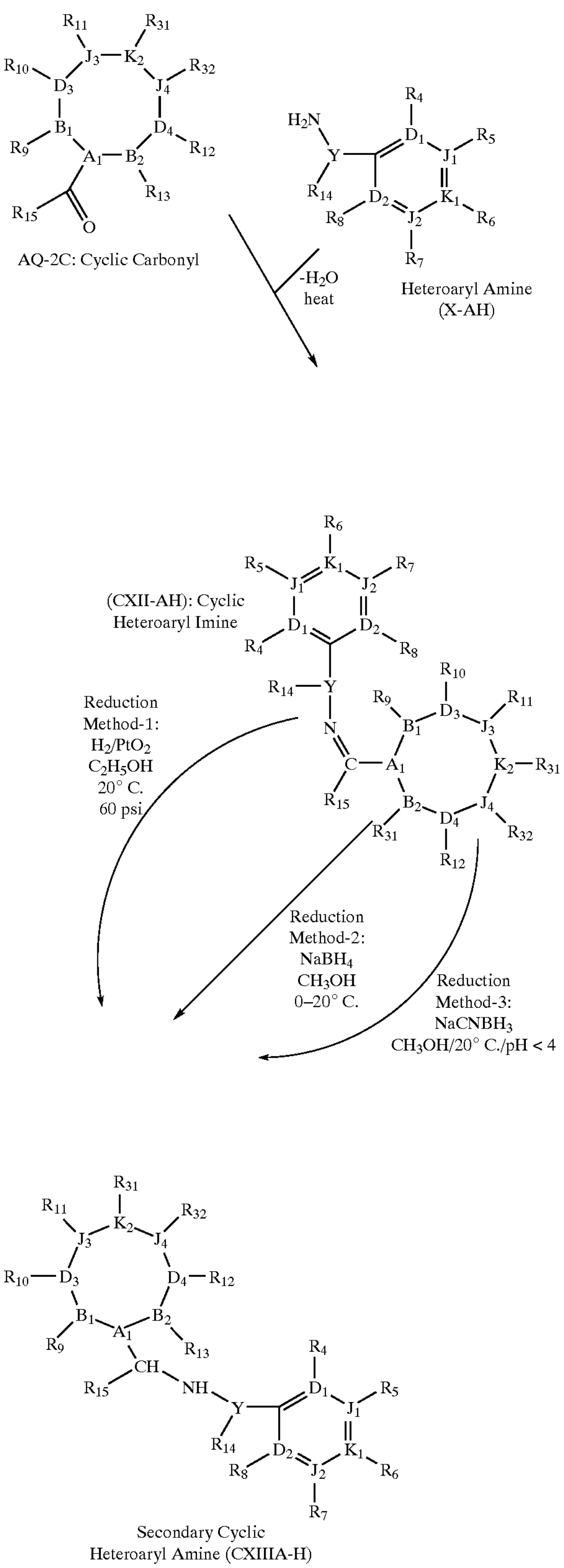
Secondary Cyclic
Heteroaryl Amine (CXIIIA-H)
Scheme 5
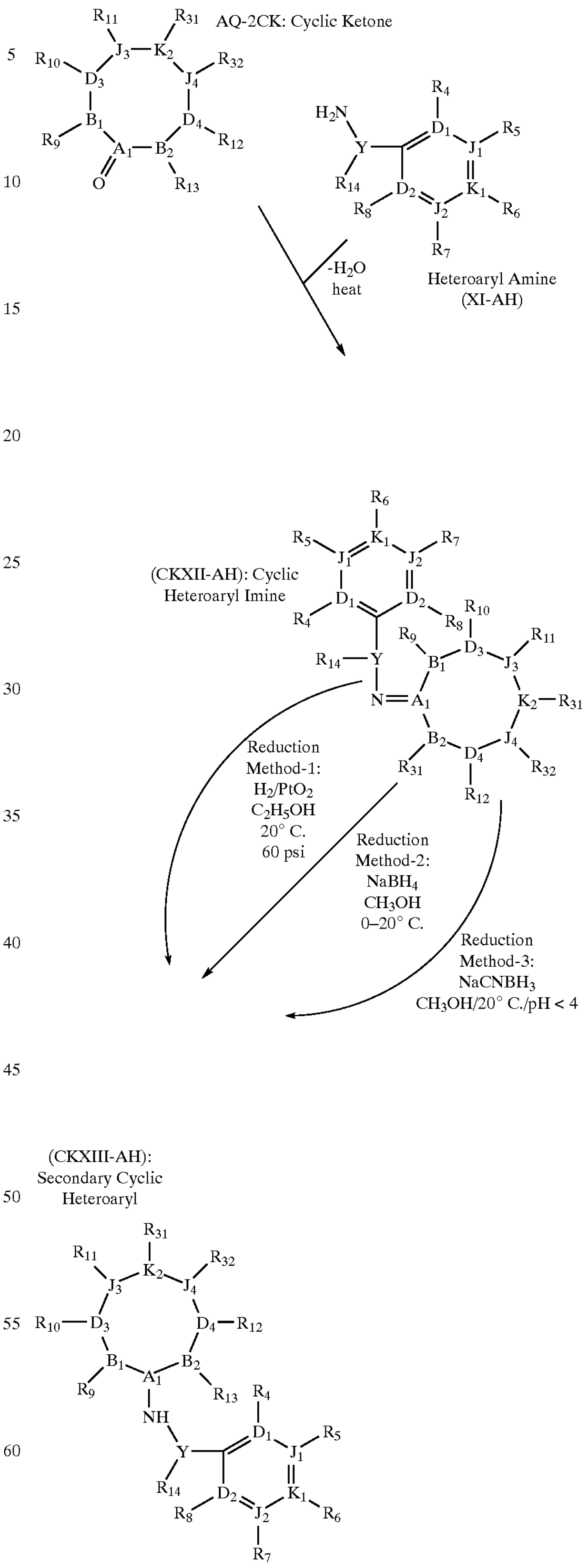

Scheme 6
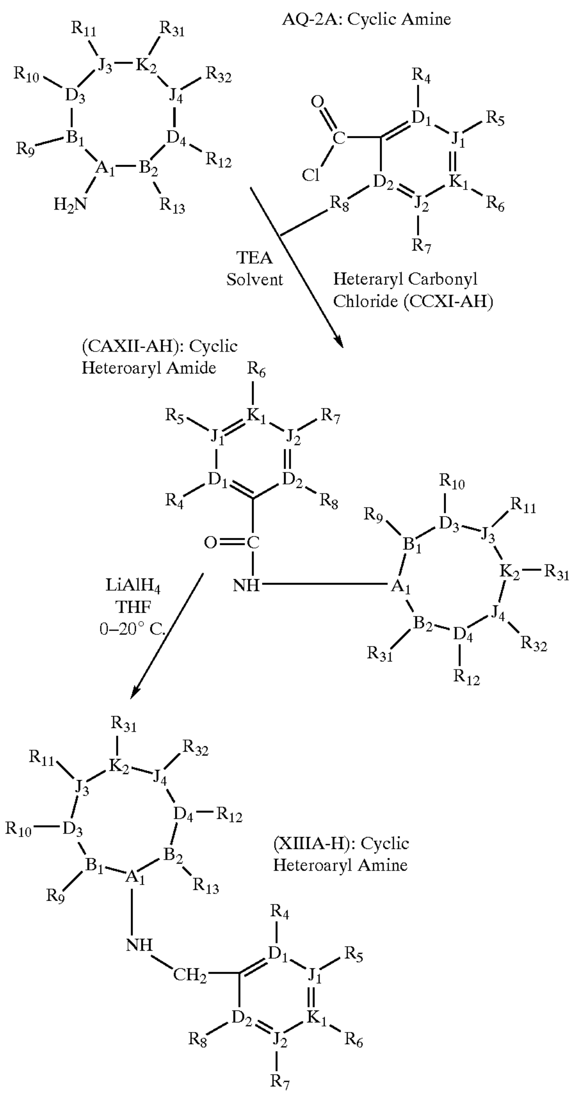
Scheme 7
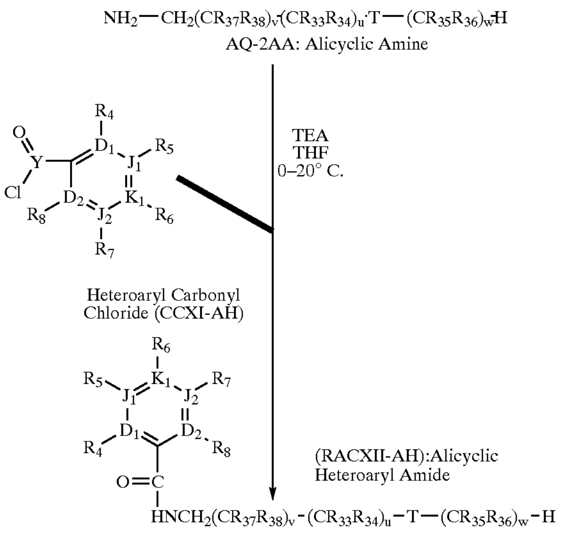
-continued
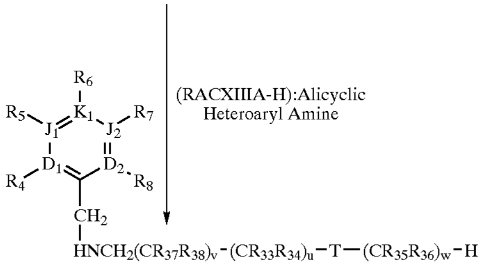
Scheme 8
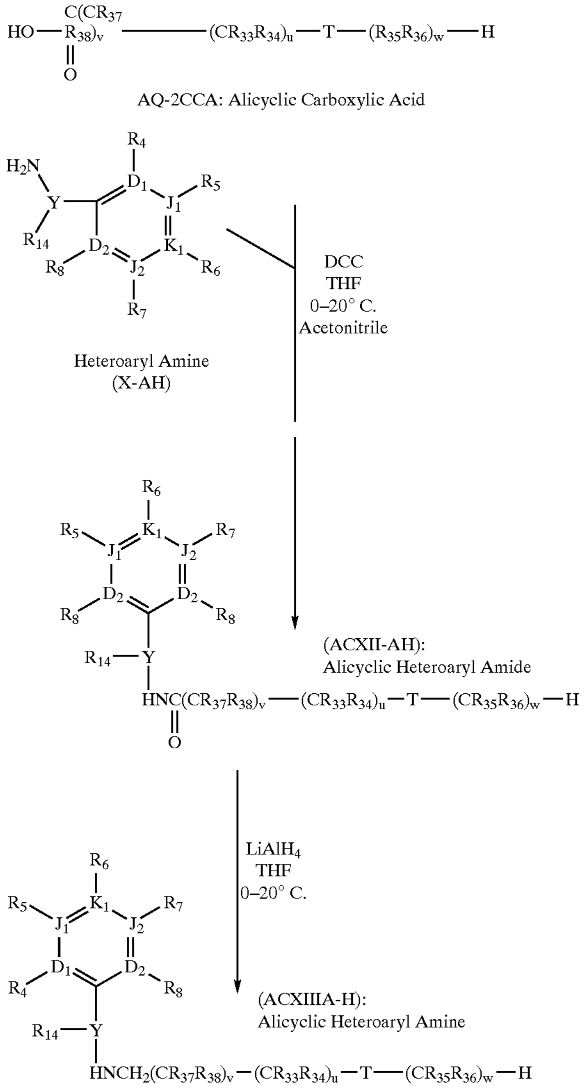
Scheme 9
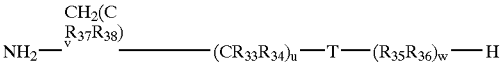
AQ-2AA: Alicyclic Amine -continued

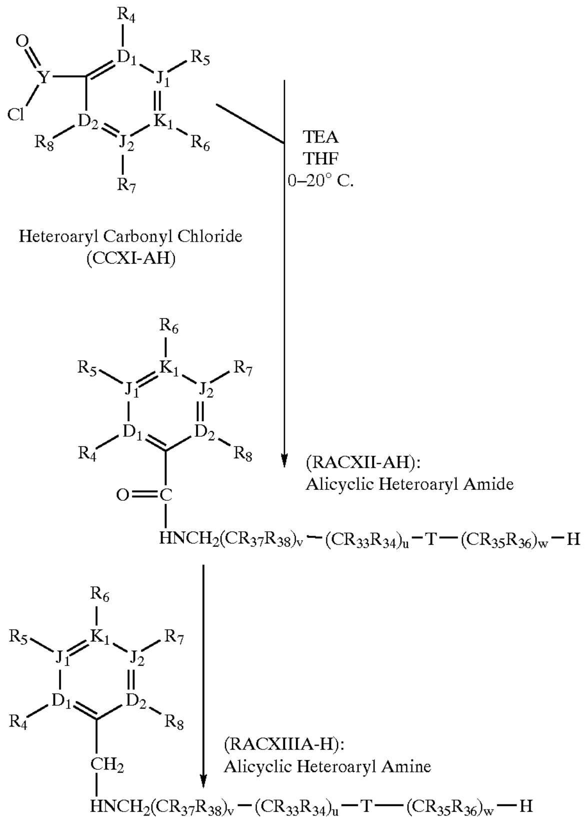

Heteroaryl Carbonyl Chloride (CCXI-AH)

(RACXII-AH): Alicyclic Heteroaryl Amide (RACXIIIA-H): Alicyclic Heteroaryl Amine Scheme 10

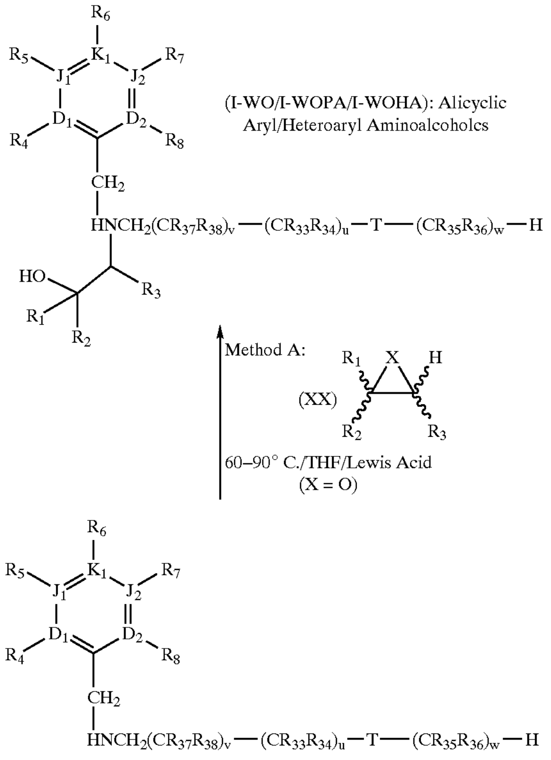

(I-WO/I-WOPA/I-WOHA): Alicyclic Aryl/Heteroaryl Aminoalcoholcs (RACXIIIA-H): Alicyclic Heteroaryl Amine Scheme 11

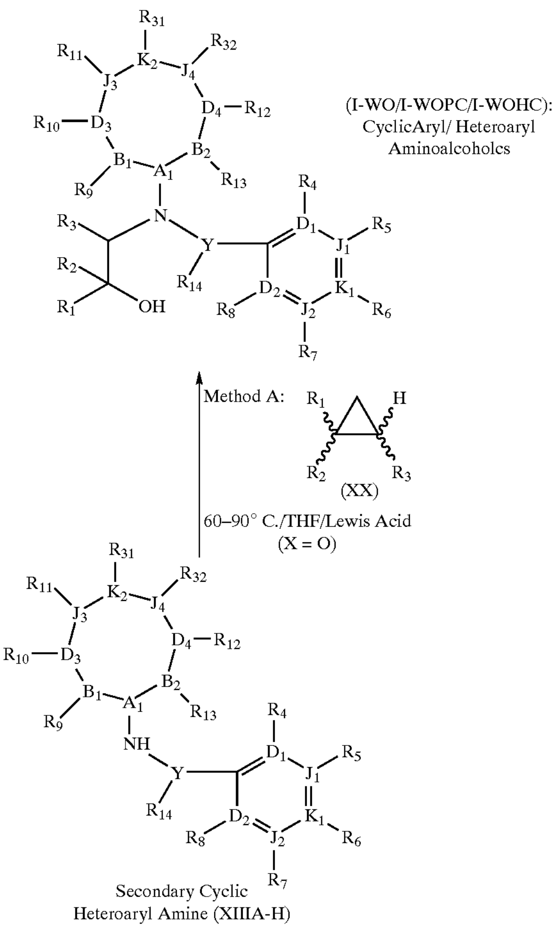

(I-WO/I-WOPC/I-WOHC): CyclicAryl/ Heteroaryl Aminoalcoholcs

Secondary Cyclic Heteroaryl Amine (XIIIA-H)

Scheme 12

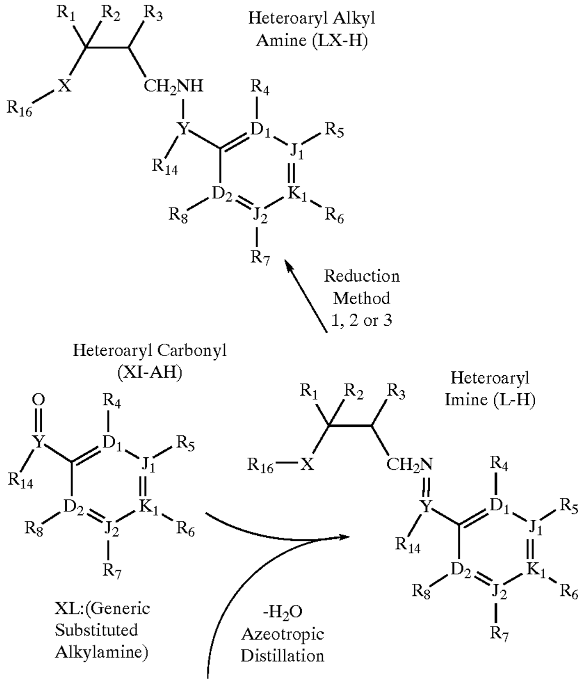

Heteroaryl Alkyl Amine (LX-H)

Heteroaryl Carbonyl (XI-AH)

Heteroaryl Imine (L-H)

XL:(Generic Substituted Alkylamine)

-continued
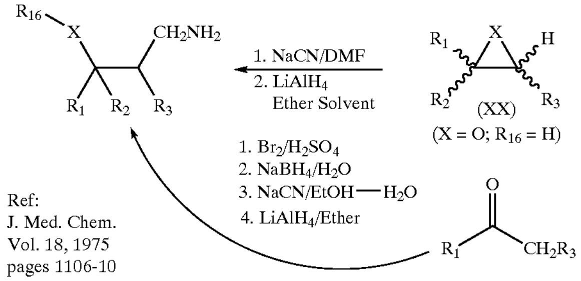
-continued
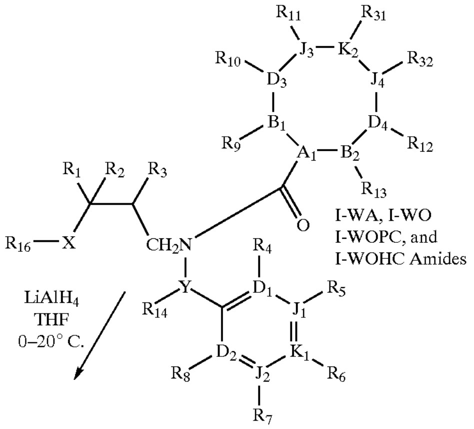
Scheme 13
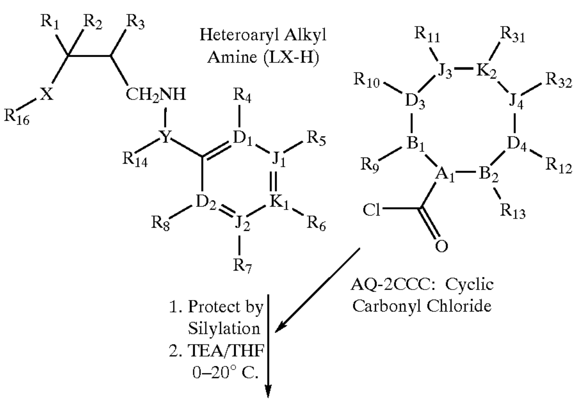
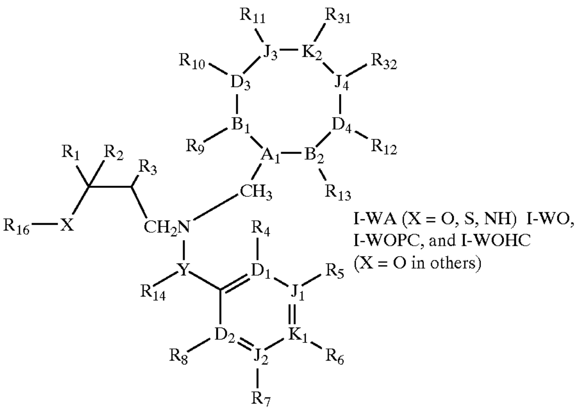
Scheme 14
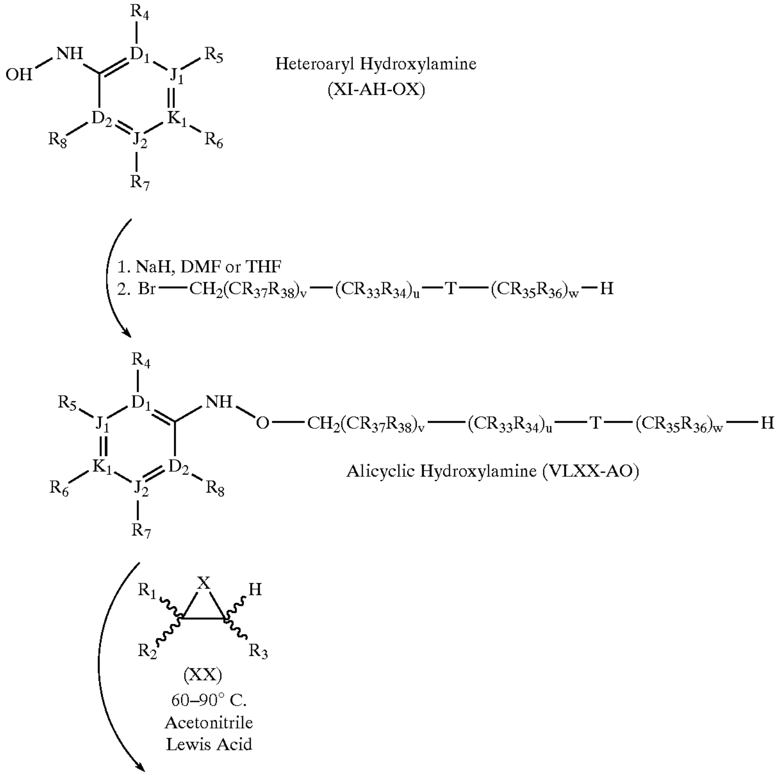

-continued

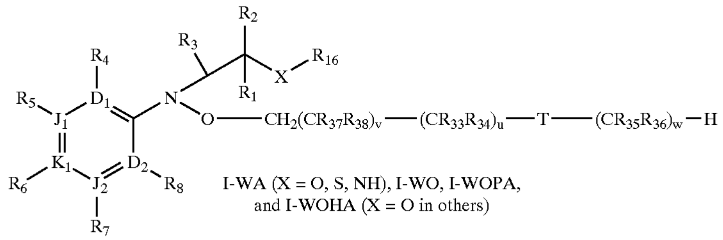

I-WA (X = O, S, NH), I-WO, I-WOPA, and I-WOHA (X = O in others)

The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR and mass spectrometry. These compounds also may be formed in vivo.

The following examples contain detailed descriptions of the methods of preparation of compounds of Formula V-H. These detailed descriptions fall within the scope and are presented for illustrative purposes only and are not intended as a restriction on the scope of the invention. All parts are by weight and temperatures are Degrees centigrade unless otherwise indicated.

EXAMPLE 1

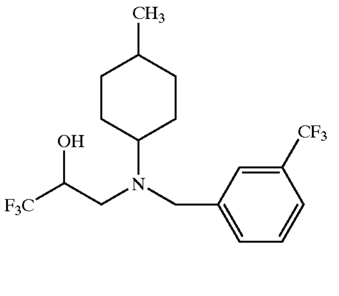

3-[(4-methylcyclohexyl)[[(3-trifluoromethyl)phenyl] methyl]amino]-1,1,1-trifluoro-2-propanol EX-1A) 4-Methylcyclohexylamine (1.15 g, 10 mmol, 97%, mixture of cis and trans isomers) and 3-trifluoromethylbenzaldehyde (1.74 g, 10 mmol) were dissolved in anhydrous chloroform (25 mL) and heated under reflux for 4 h using a Dean-Stark trap to remove water. The volatile components were removed in vacuo to give the desired imine (2.69 g) product quantitatively as a colorless oil, MS m/z=269 [$M^+$]. The oil was dissolved in methanol, and after cooling to 0° C., solid sodium borohydride was added (0.64 g, 17 mmol). The mixture was allowed to warm to room temperature and stirred for 2 h, then acidified with 1 N HCl solution. After neutralizing to pH 7.5 with 2.5 N sodium hydroxide, the mixture was extracted with diethyl ether (3x20 mL). The organic layer was washed with brine and water, then dried over anhydrous $MgSO_4$, and evaporated to give 1.96 g (68.4%) of the desired N-(4-methylcyclohexyl)[[3-(trifluoromethyl)-phenyl]methyl] amine product as a colorless oil, which was greater than 90% pure by reverse phase HPLC analysis. MS m/z=271 [$M^+$].

EX-1B) The benzylamine product from EX-1A (1.08 g, 4 mmol) and 3,3,3-trifluoro-1,2-epoxypropane (0.67 g, 6 mmol) were dissolved in 1.0 mL of acetonitrile. Ytterbium (III) trifluoromethanesulfonate (0.21 g, 0.33 mmol) was added, and the stirred solution was warmed to 50° C. for 2 h under an atmosphere of nitrogen, at which time HPLC analysis indicated that no amine starting material remained. The reaction was quenched with water and extracted with ether. The ether layer was washed with water and brine, then dried over anhydrous $MgSO_4$. The crude product was purified by flash column chromatography on silica gel eluting with ethyl acetate in hexane (1:12) to give 1.18 g (77%) of the desired 3-[(4-methyl-cyclohexyl)[[(3-trifluoromethyl) phenyl]-methyl]amino]-1,1,1-trifluoro-2-propanol product as a light amber oil, 99% pure by HPLC analysis. HRMS calculated for $C_{18}H_{23}F_6NO$: 384.1762 $[M+H]^+$, found: 384.1754. $^1$H NMR ($CDCl_3$) δ 0.92 (dd, 3H), 1.17–1.81 (m, 8H), 1.93 (m, 1H), 2.48 (m, 1H), 2.80 (m, 2H), 3.76 (d, 2H), 3.79 (m, 1H), 3.94 (s, 1H), 7.45–7.60 (m, 4H). $^{19}$F NMR ($CDCl_3$) δ–79.2 (d, 3F), –63.1 (s, 3F).

Additional substituted 3-[(N-alkyl and N-cycloalkyl) [aryl]methyl]amino-1,1,1-trifluoro-2-propanols can be prepared by one skilled in the art using similar methods, as shown in Example Table 1.

EXAMPLE TABLE 1

Substituted 3-[(N-alkyl and N-cycloalkyl)[aryl]methyl]amino-1,1,1-trifluoro-2-propanols.

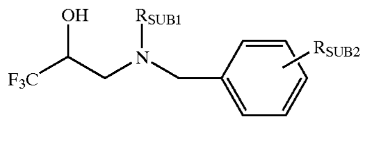

| Ex. No. | $R_{SUB1}$ | $R_{SUB2}$ | Calculated Mass $[M + H]^+$ | Observed Mass $[M + H]^+$ |
|---|---|---|---|---|
| 2 | cyclopropyl | 4-$OCF_3$ | 344.1085 | 344.1086 |
| 3 | isopropyl | 4-$OCF_3$ | 346.1242 | 346.1245 |
| 4 | cyclopropyl | 3-$OCF_3$ | 344.1085 | 344.1085 |
| 5 | isopropyl | 3-$OCF_3$ | 346.1242 | 346.1239 |
| 6 | n-propyl | 3-$OCF_3$ | 346.1242 | 346.1252 |
| 7 | cyclopentyl | 3-$OCF_3$ | 372.1398 | 372.1409 |

EXAMPLE 8

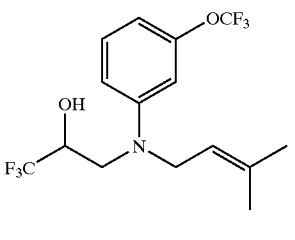

3-[(3-methyl-2-butenyl)[(3-(trifluoromethoxy) phenyl]amino]-1,1,1-trifluoro-2-propanol EX-8A) 3-Trifluoromethoxy aniline (23.81 g, 134.4 mmol) and 3,3,3-trifluoro-1,2-epoxypropane (3.76 g, 33.6 mmol) were placed into a sealed tube and heated at 80° C. for 24 h. The excess aniline was removed by distillation (70° C. at 80 torr). The resulting residue contained 8.6 g (>95%) of the desired 3-[[(trifluoromethoxy)phenyl]-amino]-1,1,1-trifluoro-2-propanol product as a light yellow oil. $^{1}H$ NMR ($CDCl_3$) δ 3.29–3.37 (m, 1H), 3.55 (dd, 1H), 4.20 (m, 1H), 6.48–6.63 (m, 3H), 7.12 (t, 1H). $^{19}F$ NMR ($CDCl_3$) δ −79.36 (s, 3F), −58.44 (s, 3F).

EX-8B) The 3-[[(trifluoromethoxy)phenyl]amino]-1,1,1-trifluoro-2-propanol product from EX-8A (18.68 g, 64.6 mmol) and imidazole (10.99 g, 0.162 mmol) were dissolved in dimethylformamide (40.0 mL) and t-butyldimethylsilylchloride (11.69 g, 77.6 mmol) was added in 3.0 g portions over 15 min. The reaction was stirred at 23° C. for 18 h. The resulting solution was diluted with ethyl acetate and washed with water and brine. The organic layer was dried ($MgSO_4$) and concentrated in vacuo. The residue was purified by column chromatography on silica gel eluting with 25% ethyl acetate in hexane to afford 17.08 g of the desired silylated product as a light golden oil. FABMS m/z=404 $[M+H]^+$. $^{1}H$ NMR ($CDCl_3$) δ 0.042 (s, 3H), 0.085 (s, 3H), 0.91 (s, 9H), 3.25–3.35 (m, 1H), 3.50 (dd, 1H), 4.10 (m, 1H), 6.40 (bs, 1H), 6.50 (dd, 1H), 6.59 (d, 1H), 7.17 (t, 1H).

EX-8C) The silylated product from EX-8B (0.15 g, 0.372 mmol) was dissolved in THF (0.5 mL) in a 2-dram glass vial with stir bar and cooled to 0° C. in an ice bath. KOtBu (1 M in THF, 1.2 eq, 0.446 mmol, 0.446 mL) was added to the cold solution in one portion. The reaction mixture was stirred at 0° C. for 5 min, then 1-chloro-3-methyl-2-butene (38.9 mg, 0.372 mmol) in 0.5 mL of THF was added in one portion to the cold reaction mixture. The ice bath was removed, and the reaction was stirred at 23° C. for 18 h. The resulting solution was diluted with ethyl acetate and washed with water and brine. The organic layer was dried ($MgSO_4$) and concentrated under a nitrogen stream. The crude residue was dissolved in 2.0 mL of THF and treated with tetrabutylammonium fluoride (1 M in THF, 1.2 eq, 0.446 mmol, 0.446 mL). The reaction mixture was stirred at 23° C. for 3 h. The reaction was diluted with ethyl acetate and washed with water and brine. The organic layer wad dried ($MgSO_4$) and concentrated under a nitrogen stream. The crude residue was purified using 0.5 g of silica gel eluting with hexane (100%) followed by 30% ethyl acetate in hexane to give 59.1 mg (44.4% yield) of the desired 3-[(3-methyl-2-butenyl)[(3-(trifluoromethoxy)-phenyl]amino]-1,1,1-trifluoro-2-propanol product as a golden oil. FABMS m/z=358 $[M+H]^+$.

Additional examples of substituted 3-[(N-alkyl, N-alkenyl and N-alkynyl)-[(trifluoromethoxy)phenyl] amino]-1,1,1-trifluoro-2-propanols can be prepared by one skilled in the art using similar methods, as shown in Example Table 2.

EXAMPLE TABLE 2

3-[(N-alkyl, N-alkenyl and N-alkynyl)[(trifluoromethoxy)phenyl] amino]-1,1,1-trifluoro-2-propanols.

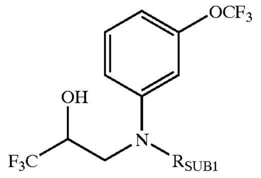

| Ex. No. | $R_{SUB1}$ | Calculated Mol. Wt. | Observed Mass $[M + H]^+$ |
|---|---|---|---|
| 9 | 2,3-octenyl | 399 | 400 |
| 10 | 2,3-propynyl | 327 | 328 |
| 11 | 3-methyl-butyl | 359 | 360 |
| 12 | 2-(carbomethoxy)-2-propenyl | 387 | 388 |
| 13 | 3-(carbomethoxy)-2-propenyl | 387 | 388 |
| 14 | 4-methoxy-2-butenyl | 373 | 374 |

EXAMPLE 15

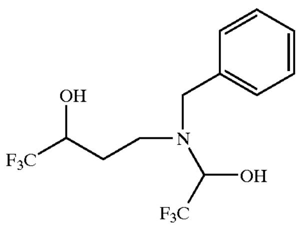

1,1'-[(Phenylmethyl)imino]bis[3,3,3-trifluoro-2-propanol]

Benzylamine (1.5 eq, 2.88 g, 2.94 mL, 26.8 mmol) was combined with 3,3,3-trifluoro-1,2-epoxypropane (2.0 g, 17.86 mmol) in a sealed glass tube and heated at 80° C. for 18 h. Upon cooling to room temperature, the reaction mixture formed a slushy white solid. The solid was collected by filtration and washed with diethyl ether. The mother liquor was concentrated in vacuo to give 1.71 g (43%) of the desired 1,1'-[(phenyl-methyl)imino]bis[3,3,3-trifluoro-2-propanol] product as a colorless oil. FABMS m/z=332 $[M+H]^+$. $^{1}H$ NMR ($CDCl_3$) δ 2.85–2.96 (m, 4H), 3.94 (s, 2H), 3.94–3.97 (m, 2H), 7.24–7.37 (m, 5H).

Additional examples of substituted 1,1'-[(phenylmethyl) imino]bis[3,3,3-tri-fluoro-2-propanols] can be prepared by one skilled in the art using similar methods, as shown in Example Table 3.

EXAMPLE TABLE 3

Substituted 1,1'-[(phenylmethyl)imino]bis[3,3,3-trifluoro-2-propanols]

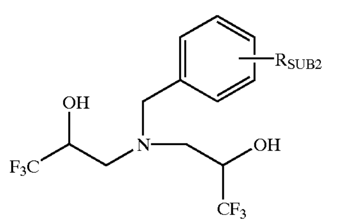

| Ex. No. | $R_{SUB2}$ | Calculated Mass [M + H]+ | Observed Mass [M + H]+ |
|---|---|---|---|
| 16 | 3-trifluoromethyl | 400.0959 | 400.0923 |
| 17 | 4-trifluoromethoxy | 416.0908 | 416.0905 |

EXAMPLE 18

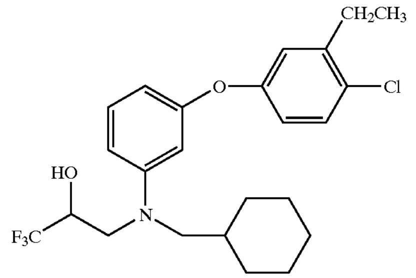

3-[[3-(4-chloro-3-ethylphenoxy)phenyl][3-cyclohexylmethyl]amino]-1,1,1-trifluoro-2-propanol EX-18A) To a solution of 1,3-dinitrobenzene (16.8 g, 0.1 mol) and 4-chloro-3-ethylphenol (15.6 g, 0.1 mol) in 200 mL of dimethylsulfoxide was added cesium carbonate (65 g, 0.2 mol). The reaction mixture was heated at 100° C. under nitrogen overnight then cooled to room temperature. The reaction mixture was filtered through celite then rinsed with diethyl ether and a small amount of water. The filtrate was extracted several times with diethyl ether. The organic layers were combined, washed with water and brine, dried over $MgSO_4$, and concentrated in vacuo to give 21.8 g (78%) of the desired 3-(4-chloro-3-ethylphenoxy)-1-nitrobenzene product as a dark orange oil, which was greater than 90% pure by reverse phase HPLC analysis. HRMS calcd. for $C_{14}H_{12}ClNO_3$: 295.0849 $[M+NH_4]^+$, found 295.0862.

EX-18B) To a solution of 3-(4-chloro-3-ethylphenoxy)-1-nitrobenzene (10 g, 0.036 mol) from EX-18A in 400 mL of glacial acetic acid and 1 mL of water was added zinc metal (20 g, 0.305 mol) at room temperature, and the resultant mixture was stirred for 1 h. The reaction mixture was filtered through celite. The filtrate was neutralized with ammonium hydroxide and extracted with diethyl ether. The organic layer was washed with water and brine, dried over $MgSO_4$, and concentrated in vacuo to give 10 g (100%) of the desired 3-(4-chloro-3-ethylphenoxy)aniline product as a dark orange oil, which was greater than 90% pure by reverse phase HPLC analysis. HRMS calcd. for $C_{14}H_{14}ClNO$: 248.0842 $[M+H]^+$, found: 248.0833.

EX-18C) The 3-(4-chloro-3-ethylphenoxy)aniline (0.545 g, 0.002 mol) product from EX-18B was mixed with neat 3,3,3-trifluoro-1,2-epoxypropane (0.220 g, 0.002 mol) in a pressurized vial. The resulting mixture was heated at 90° C. for 18 h, cooled, and the excess 3,3,3-trifluoro-1,2-epoxypropane was removed in vacuo. The crude product was purified by flash column chromatography on silica gel eluting with 1:4 ethyl acetate in hexane to give 0.254 g (35%) of the desired 3-[[3-(4-chloro-3-ethyl-phenoxy)phenyl]amino]-1,1,1-trifluoro-2-propanol product as a pure orange oil. Anal calcd. for $C_{17}H_{17}NOF_3Cl$: C, 56.75; H, 4.76; N, 3.89. Found: C, 56.72; H, 4.70; N, 3.85. HRMS calcd.: 360.0978 $[M+H]^+$, found: 360.0969. $^1H$ NMR ($CDCl_3$) δ 1.50 (t, 3H), 2.72 (m, 2H), 3.36 (m, 1H), 3.54 (m, 1H), 4.20 (m, 1H), 6.42 (m, 2H), 6.81 (dd, 1H), 6.94 (d, 1H), 7.18 (d, 1H), 7.25 (m, 2H).

The 3-[[3-(4-chloro-3-ethylphenoxy)phenyl]amino]-1,1,1-trifluoro-2-propanol product from EX-18C was dissolved in 12 mL of tetrahydrofuran. To this stirred solution was added cyclohexanecarboxaldehyde (0.032 g, 0.285 mmol), followed by sodium tri-acetoxyborohydride (0.079 g, 0.370 mmol and concentrated acetic acid (0.020 g, 0.325 mmol). The resulting mixture was stirred at room temperature for 18 h. Additional cyclohexanecarboxaldehyde (0.032 g, 0.285 mmol) was added and the mixture was allowed to stir at room temperature for another 18 h. The reaction was quenched with saturated sodium bicarbonate and extracted with methylene chloride. The organic layers were combined, dried over $MgSO_4$ and concentrated to an orange/brown oil. The crude product was purified by flash column chromatography on silica gel eluting with 1:4 ethyl acetate in hexane to give 0.080 g (61%) of the desired 3-[[3-(4-chloro-3-ethylphenoxy)phenyl][3-cyclohexylmethyl]amino]-1,1,1-trifluoro-2-propanol product as a yellow-orange oil (>95% pure by HPLC). HRMS calcd.: 456.1917 $[M+H]^+$, found: 456.1942. $^1H$ NMR ($CDCl_3$) δ 0.82–1.01 (m, 2H), 1.22–1.27 (m, 3H), 1.73–1.76 (m, 5H), 2.74 (dd, 2H), 3.15 (dd, 2H), 3.23 (dd, 1H), 3.52 (m, 1H), 3.80 (dd, 1H), 4.28 (m, 1H), 6.34 (d, 2H), 6.42 (d, 1H), 6.83 (dd, 1H), 6.98 (d, 1H), 7.19 (t, 1H), 7.29 (d, 1H). $^{19}F$ NMR ($CDCl_3$) δ–79.06 (d, 3F).

Based on the preceding procedures, additional substituted 3-[(N-alkyl)-[[aryl]methyl]amino]-1,1,1-trifluoro-2-propanols and 3-[(N-cycloalkyl)-([[aryl]methyl]-amino]-halo-2-propanols are prepared by one skilled in the art using similar methods, as shown in Example Tables 4 and 5. Similarly, substituted 3-[(N-aryl)[[cycloalkyl]-methyl]amino]-halo-2-propanols and substituted 3-[(N-aryl)[[haloalkyl]methyl]amino]-halo-2-propanols are prepared by one skilled in the art using analogous methods, as shown in Example Tables 6 and 7.

EXAMPLE TABLE 4

3-[(N-alkyl)[[aryl]methyl]amino]-1,1,1-trifluoro-2-propanols.

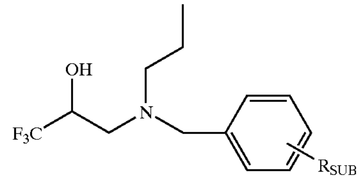

| Ex. No. | $R_{SUB}$ |
|---|---|
| 19 | 4-$OCF_3$ |
| 20 | 3-$OCF_2CF_2H$ |
| 21 | 2-F, 5-$CF_3$ |
| 22 | 2-F, 4-$CF_3$ |

EXAMPLE TABLE 4-continued

3-[(N-alkyl)[[aryl]methyl]amino]-1,1,1-trifluoro-2-propanols.

| Ex. No. | $R_{SUB}$ |
|---|---|
| 23 | 3-$CF_3$, 4-F |
| 24 | 3-$CF_3CF_2$ |
| 25 | 3-cyclopentyl |
| 26 | 3-isopropoxy |
| 27 | 3-$SCF_3$ |
| 28 | 3-sec-butoxy |
| 29 | 3-$C(CF_3)_2OH$ |
| 30 | 3-(2-furyl) |
| 31 | 3-(3-furyl) |
| 32 | 3-isobutyl |
| 33 | 3-isobutoxy |
| 34 | 3-ethoxy |
| 35 | 3-$OCH_2CF_3$ |
| 36 | 3-propoxy |
| 37 | 3-tert-butoxy |
| 38 | 3-(2-thienyl) |
| 39 | 3-cyclopropyl |
| 40 | 4-F, 3-(2-furyl) |
| 41 | 3-(3-$CF_3$-phenoxy) |
| 42 | 3,4-($OCF_2CF_2O$) |
| 43 | 3-$OCF_2CF_3$ |
| 44 | 3-cyclopentoxy |
| 45 | 3-(cyclopropyl)methoxy |
| 46 | 3-$OCH_2CH(OH)CF_3$ |
| 47 | 3-$CF_3$ |
| 48 | 4-$CF_3$ |
| 49 | 3-$CH_2CF_2CF_3$ |
| 50 | 3-$CH_2CF_3$ |
| 51 | 3-$CH(CF_3)_2$ |
| 52 | 3-$CF_2CF_2CF_3$ |
| 53 | 3-phenoxy |
| 54 | 3-phenyl |
| 55 | 3-(tetrahydro-2-furyl) |
| 56 | isoamyl |

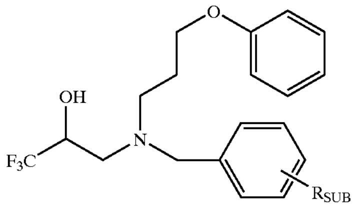

| Ex. No. | $R_{SUB}$ |
|---|---|
| 57 | 3-$OCF_3$ |
| 58 | 3-$OCF_2CF_2H$ |
| 59 | 2-F, 5-$CF_3$ |
| 60 | 2-F, 4-$CF_3$ |
| 61 | 3-$CF_3$, 4-F |
| 62 | 3-$CF_3CF_2$ |
| 63 | 3-cyclopentyl |
| 64 | 3-isopropoxy |
| 65 | 3-$SCF_3$ |
| 66 | 3-sec-butoxy |
| 67 | 3-$C(CF_3)_2OH$ |
| 68 | 3-(2-furyl) |
| 69 | 3-(3-furyl) |
| 70 | 3-isobutyl |
| 71 | 3-isobutoxy |
| 72 | 3-ethoxy |
| 73 | 3-$OCH_2CF_3$ |
| 74 | 3-propoxy |
| 75 | 3-tert-butoxy |
| 76 | 3-(2-thienyl) |
| 77 | 3-cyclopropyl |
| 78 | 4-F, 3-(2-furyl) |
| 79 | 3-(3-$CF_3$-phenoxy) |
| 80 | 3,4-($OCF_2CF_2O$) |
| 81 | 3-$OCF_2CF_3$ |
| 82 | 3-cyclopentoxy |
| 83 | 3-(cyclopropyl)methoxy |
| 84 | 3-$OCH_2CH(OH)CF_3$ |
| 85 | 3-$CF_3$ |

EXAMPLE TABLE 4-continued

3-[(N-alkyl)[[aryl]methyl]amino]-1,1,1-trifluoro-2-propanols.

| Ex. No. | $R_{SUB}$ |
|---|---|
| 86 | 4-$CF_3$ |
| 87 | 3-$CH_2CF_2CF_3$ |
| 88 | 3-$CH_2CF_3$ |
| 89 | 3-$CH(CF_3)_2$ |
| 90 | 3-$CF_2CF_2CF_3$ |
| 91 | 3-phenoxy |
| 92 | 3-phenyl |
| 93 | 3-(tetrahydro-2-furyl) |
| 94 | isoamyl |

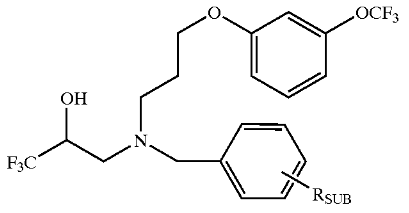

| Ex. No. | $R_{SUB}$ |
|---|---|
| 95 | 3-$OCF_3$ |
| 96 | 3-$OCF_2CF_2H$ |
| 97 | 2-F, 5-$CF_3$ |
| 98 | 2-F, 4-$CF_3$ |
| 99 | 3-$CF_3$, 4-F |
| 100 | 3-$CF_3CF_2$ |
| 101 | 3-cyclopentyl |
| 102 | 3-isopropoxy |
| 103 | 3-$SCF_3$ |
| 104 | 3-sec-butoxy |
| 105 | 3-$C(CF_3)_2OH$ |
| 106 | 3-(2-furyl) |
| 107 | 3-(3-furyl) |
| 108 | 3-isobutyl |
| 109 | 3-isobutoxy |
| 110 | 3-ethoxy |
| 111 | 3-$OCH_2CF_3$ |
| 112 | 3-propoxy |
| 113 | 3-tert-butoxy |
| 114 | 3-(2-thienyl) |
| 115 | 3-cyclopropyl |
| 116 | 4-F, 3-(2-furyl) |
| 117 | 3-(3-$CF_3$-phenoxy) |
| 118 | 3,4-($OCF_2CF_2O$) |
| 119 | 3-$OCF_2CF_3$ |
| 120 | 3-cyclopentoxy |
| 121 | 3-(cyclopropyl)methoxy |
| 122 | 3-$OCH_2CH(OH)CF_3$ |
| 123 | 3-$CF_3$ |
| 124 | 4-$CF_3$ |
| 125 | 3-$CH_2CF_2CF_3$ |
| 126 | 3-$CH_2CF_3$ |
| 127 | 3-$CH(CF_3)_2$ |
| 128 | 3-$CF_2CF_2CF_3$ |
| 129 | 3-phenoxy |
| 130 | 3-phenyl |
| 131 | 3-(tetrahydro-2-furyl) |
| 132 | isoamyl |

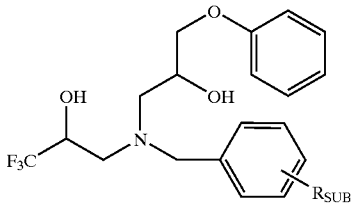

| Ex. No. | $R_{SUB}$ |
|---|---|
| 133 | 3-$OCF_3$ |
| 134 | 3-$OCF_2CF_2H$ |
| 135 | 2-F, 5-$CF_3$ |
| 136 | 2-F, 4-$CF_3$ |
| 137 | 3-$CF_3$, 4-F |

EXAMPLE TABLE 4-continued

3-[(N-alkyl)[[aryl]methyl]amino]-1,1,1-trifluoro-2-propanols.

| Ex. No. | $R_{SUB}$ |
|---|---|
| 138 | 3-$CF_3CF_2$ |
| 139 | 3-cyclopentyl |
| 140 | 3-isopropoxy |
| 141 | 3-$SCF_3$ |
| 142 | 3-sec-butoxy |
| 143 | 3-$C(CF_3)_2OH$ |
| 144 | 3-(2-furyl) |
| 145 | 3-(3-furyl) |
| 146 | 3-isobutyl |
| 147 | 3-isobutoxy |
| 148 | 3-ethoxy |
| 149 | 3-$OCH_2CF_3$ |
| 150 | 3-propoxy |
| 151 | 3-tert-butoxy |
| 152 | 3-(2-thienyl) |
| 153 | 3-cyclopropyl |
| 154 | 4-F, 3-(2-furyl) |
| 155 | 3-(3-$CF_3$-phenoxy) |
| 156 | 3,4-($OCF_2CF_2O$) |
| 157 | 3-$OCF_2CF_3$ |
| 158 | 3-cyclopentoxy |
| 159 | 3-(cyclopropyl)methoxy |
| 160 | 3-$OCH_2CH(OH)CF_3$ |
| 161 | 3-$CF_3$ |
| 162 | 4-$CF_3$ |
| 163 | 3-$CH_2CF_2CF_3$ |
| 164 | 3-$CH_2CF_3$ |
| 165 | 3-$CH(CF_3)_2$ |
| 166 | 3-$CF_2CF_2CF_3$ |
| 167 | 3-phenoxy |
| 168 | 3-phenyl |
| 169 | 3-(tetrahydro-2-furyl) |
| 170 | isoamyl |

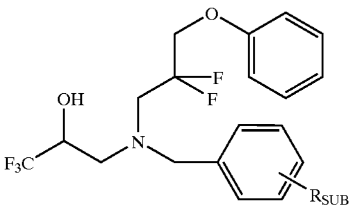

| Ex. No. | $R_{SUB}$ |
|---|---|
| 171 | 3-$OCF_3$ |
| 172 | 3-$OCF_2CF_2H$ |
| 173 | 2-F, 5-$CF_3$ |
| 174 | 2-F, 4-$CF_3$ |
| 175 | 3-$CF_3$, 4-F |
| 176 | 3-$CF_3CF_2$ |
| 177 | 3-cyclopentyl |
| 178 | 3-isopropoxy |
| 179 | 3-$SCF_3$ |
| 180 | 3-sec-butoxy |
| 181 | 3-$C(CF_3)_2OH$ |
| 182 | 3-(2-furyl) |
| 183 | 3-(3-furyl) |
| 184 | 3-isobutyl |
| 185 | 3-isobutoxy |
| 186 | 3-ethoxy |
| 187 | 3-$OCH_2CF_3$ |
| 188 | 3-propoxy |
| 189 | 3-tert-butoxy |
| 190 | 3-(2-thienyl) |
| 191 | 3-cyclopropyl |
| 192 | 4-F, 3-(2-furyl) |
| 193 | 3-(3-$CF_3$-phenoxy) |
| 194 | 3,4-($OCF_2CF_2O$) |
| 195 | 3-$OCF_2CF_3$ |
| 196 | 3-cyclopentoxy |
| 197 | 3-(cyclopropyl)methoxy |

EXAMPLE TABLE 4-continued

3-[(N-alkyl)[[aryl]methyl]amino]-1,1,1-trifluoro-2-propanols.

| Ex. No. | $R_{SUB}$ |
|---|---|
| 198 | 3-$OCH_2CH(OH)CF_3$ |
| 199 | 3-$CF_3$ |
| 200 | 4-$CF_3$ |
| 201 | 3-$CH_2CF_2CF_3$ |
| 202 | 3-$CH_2CF_3$ |
| 203 | 3-$CH(CF_3)_2$ |
| 204 | 3-$CF_2CF_2CF_3$ |
| 205 | 3-phenoxy |
| 206 | 3-phenyl |
| 207 | 3-(tetrahydro-2-furyl) |
| 208 | isoamyl |

EXAMPLE TABLE 5

| Ex. No. | $R_{SUB}$ |
|---|---|

3-[(N-cycloalkyl)[[aryl]methyl]amino]-1,1,1-trifluoro-2-propanols.

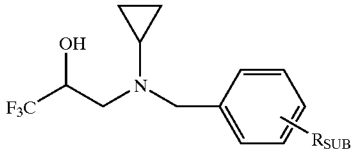

| Ex. No. | $R_{SUB}$ |
|---|---|
| 209 | 3-tert-butoxy |
| 210 | 3-$OCF_2CF_2H$ |
| 211 | 2-F 5-$CF_3$ |
| 212 | 2-F, 4-$CF_3$ |
| 213 | 3-$CF_3$, 4-F |
| 214 | 3-$CF_3CF_2$ |
| 215 | 3-cyclopentyl |
| 216 | 3-isopropoxy |
| 217 | 3-$SCF_3$ |
| 218 | 3-sec-butoxy |
| 219 | 3-$C(CF_3)_2OH$ |
| 220 | 3-(2-furyl) |
| 221 | 3-(3-furyl) |
| 222 | 3-isobutyl |
| 223 | 3-isobutoxy |
| 224 | 3-ethoxy |
| 225 | 3-$OCH_2CF_3$ |
| 226 | 3-propoxy |
| 227 | 3-(2-pyridyl) |
| 228 | 3-(2-thienyl) |
| 229 | 3-cyclopropyl |
| 230 | 4-F, 3-(2-furyl) |
| 231 | 3-(3-$CF_3$-phenoxy) |
| 232 | 3,4-($OCF_2CF_2O$) |
| 233 | 3-$OCF_2CF_3$ |
| 234 | 3-cyclopentoxy |
| 235 | 3-(cyclopropyl)methoxy |
| 236 | 3-$OCH_2CH(OH)CF_3$ |
| 237 | 3-$CF_3$ |
| 238 | 4-$CF_3$ |
| 239 | 3-$CH_2CF_2CF_3$ |
| 240 | 3-$CH_2CF_3$ |
| 241 | 3-$CH(CF_3)_2$ |
| 242 | 3-$CF_2CF_2CF_3$ |
| 243 | 3-phenoxy |
| 244 | 3-phenyl |
| 245 | 3-(tetrahydro-2-furyl) |
| 246 | isoamyl |

EXAMPLE TABLE 5-continued

| Ex. No. | $R_{SUB}$ |
|---|---|

3-[(N-cycloalkyl)[[aryl]methyl]amino]-halo-2-propanols.

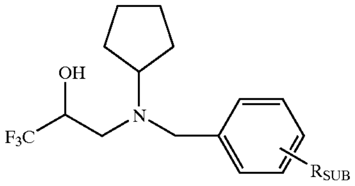

| Ex. No. | $R_{SUB}$ |
|---|---|
| 247 | 4-$OCF_3$ |
| 248 | 3-$OCF_2CF_2H$ |
| 249 | 2-F, 5-$CF_3$ |
| 250 | 2-F, 4-$CF_3$ |
| 251 | 3-$CF_3$, 4-F |
| 252 | 3-$CF_3CF_2$ |
| 253 | 3-cyclopentyl |
| 254 | 3-isopropoxy |
| 255 | 3-$SCF_3$ |
| 256 | 3-sec-butoxy |
| 257 | 3-$C(CF_3)_2OH$ |
| 258 | 3-(2-furyl) |
| 259 | 3-(3-furyl) |
| 260 | 3-isobutyl |
| 261 | 3-isobutoxy |
| 262 | 3-ethoxy |
| 263 | 3-$OCH_2CF_3$ |
| 264 | 3-propoxy |
| 265 | 3-tert-butoxy |
| 266 | 3-(2-thienyl) |
| 267 | 3-cyclopropyl |
| 268 | 4-F, 3-(2-furyl) |
| 269 | 3-(3-$CF_3$-phenoxy) |
| 270 | 3,4-($OCF_2CF_2O$) |
| 271 | 3-$OCF_2CF_3$ |
| 272 | 3-cyclopentoxy |
| 273 | 3-(cyclopropyl)methoxy |
| 274 | 3-$OCH_2CH(OH)CF_3$ |
| 275 | 3-$CF_3$ |
| 276 | 4-$CF_3$ |
| 277 | 3-$CH_2CF_2CF_3$ |
| 278 | 3-$CH_2CF_3$ |
| 279 | 3-$CH(CF_3)_2$ |
| 280 | 3-$CF_2CF_2CF_3$ |
| 281 | 3-phenoxy |
| 282 | 3-phenyl |
| 283 | 3-(tetrahydro-2-furyl) |
| 284 | isoamyl |

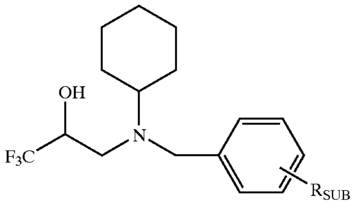

| Ex. No. | $R_{SUB}$ |
|---|---|
| 285 | 3-$OCF_3$ |
| 286 | 3-$OCF_2CF_2H$ |
| 287 | 2-F, 5-$CF_3$ |
| 288 | 2-F, 4-$CF_3$ |
| 289 | 3-$CF_3$, 4-F |
| 290 | 3-$CF_3CF_2$ |
| 291 | 3-cyclopentyl |
| 292 | 3-isopropoxy |
| 293 | 3-$SCF_3$ |
| 294 | 3-sec-butoxy |
| 295 | 3-$C(CF_3)_2OH$ |
| 296 | 3-(2-furyl) |
| 297 | 3-(3-furyl) |
| 298 | 3-isobutyl |
| 299 | 3-isobutoxy |

EXAMPLE TABLE 5-continued

| Ex. No. | $R_{SUB}$ |
|---|---|
| 300 | 3-ethoxy |
| 301 | 3-$OCH_2CF_3$ |
| 302 | 3-propoxy |
| 303 | 3-tert-butoxy |
| 304 | 3-(2-thienyl) |
| 305 | 3-cyclopropyl |
| 306 | 4-F, 3-(2-furyl) |
| 307 | 3-(3-$CF_3$-phenoxy) |
| 308 | 3,4-($OCF_2CF_2O$) |
| 309 | 3-$OCF_2CF_3$ |
| 310 | 3-cyclopentoxy |
| 311 | 3-(cyclopropyl)methoxy |
| 312 | 3-$OCH_2CH(OH)CF_3$ |
| 313 | 3-$CF_3$ |
| 314 | 4-$CF_3$ |
| 315 | 3-$CH_2CF_2CF_3$ |
| 316 | 3-$CH_2CF_3$ |
| 317 | 3-$CH(CF_3)_2$ |
| 318 | 3-$CF_2CF_2CF_3$ |
| 319 | 3-phenoxy |
| 320 | 3-phenyl |
| 321 | 3-(tetrahydro-2-furyl) |

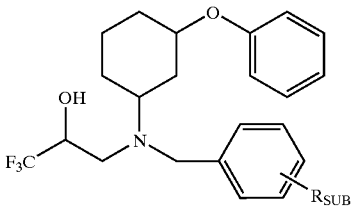

| Ex. No. | $R_{SUB}$ |
|---|---|
| 322 | isoamyl |
| 323 | 3-$OCF_3$ |
| 324 | 3-$OCF_2CF_2H$ |
| 325 | 2-F, 5-$CF_3$ |
| 326 | 2-F, 4-$CF_3$ |
| 327 | 3-$CF_3$, 4-F |
| 328 | 3-$CF_3CF_2$ |
| 329 | 3-cyclopentyl |
| 330 | 3-isopropoxy |
| 331 | 3-$SCF_3$ |
| 332 | 3-sec-butoxy |
| 333 | 3-$C(CF_3)_2OH$ |
| 334 | 3-(2-furyl) |
| 335 | 3-(3-furyl) |
| 336 | 3-isobutyl |
| 337 | 3-isobutoxy |
| 338 | 3-ethoxy |
| 339 | 3-$OCH_2CF_3$ |
| 340 | 3-propoxy |
| 341 | 3-tert-butoxy |
| 342 | 3-(2-thienyl) |
| 343 | 3-cyclopropyl |
| 344 | 4-F, 3-(2-furyl) |
| 345 | 3-(3-$CF_3$-phenoxy) |
| 346 | 3,4-($OCF_2CF_2O$) |
| 347 | 3-$OCF_2CF_3$ |
| 348 | 3-cyclopentoxy |
| 349 | 3-(cyclopropyl)methoxy |
| 350 | 3-$OCH_2CH(OH)CF_3$ |
| 351 | 3-$CF_3$ |
| 352 | 4-$CF_3$ |
| 353 | 3-$CH_2CF_2CF_3$ |
| 354 | 3-$CH_2CF_3$ |
| 355 | 3-$CH(CF_3)_2$ |
| 356 | 3-$CF_2CF_2CF_3$ |
| 357 | 3-phenoxy |
| 358 | 3-phenyl |
| 359 | 3-(tetrahydro-2-furyl) |
| 360 | isoamyl |

EXAMPLE TABLE 5-continued

| Ex. No. | $R_{SUB}$ |
|---|---|
| 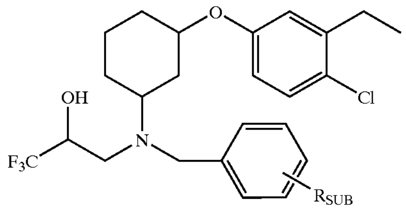 | |
| 361 | 3-$OCF_3$ |
| 362 | 3-$OCF_2CF_2H$ |
| 363 | 2-F, 5-$CF_3$ |
| 364 | 2-F, 4-$CF_3$ |
| 365 | 3-$CF_3$, 4-F |
| 366 | 3-$CF_3CF_2$ |
| 367 | 3-cyclopentyl |
| 368 | 3-isopropoxy |
| 369 | 3-$SCF_3$ |
| 370 | 3-sec-butoxy |
| 371 | 3-$C(CF_3)_2OH$ |
| 372 | 3-(2-furyl) |
| 373 | 3-(3-furyl) |
| 374 | 3-isobutyl |
| 375 | 3-isobutoxy |
| 376 | 3-ethoxy |
| 377 | 3-$OCH_2CF_3$ |
| 378 | 3-propoxy |
| 379 | 3-tert-butoxy |
| 380 | 3-(2-thienyl) |
| 381 | 3-cyclopropyl |
| 382 | 4-F, 3-(2-furyl) |
| 383 | 3-(3-$CF_3$-phenoxy) |
| 384 | 3,4-($OCF_2CF_2O$) |
| 385 | 3-$OCF_2CF_3$ |
| 386 | 3-cyclopentoxy |
| 387 | 3-(cyclopropyl)methoxy |
| 388 | 3-$OCH_2CH(OH)CF_3$ |
| 389 | 3-$CF_3$ |
| 390 | 4-$CF_3$ |
| 391 | 3-$CH_2CF_2CF_3$ |
| 392 | 3-$CH_2CF_3$ |
| 393 | 3-$CH(CF_3)_2$ |
| 394 | 3-$CF_2CF_2CF_3$ |
| 395 | 3-phenoxy |
| 396 | 3-phenyl |
| 397 | 3-(tetrahydro-2-furyl) |
| 398 | isoamyl |
| 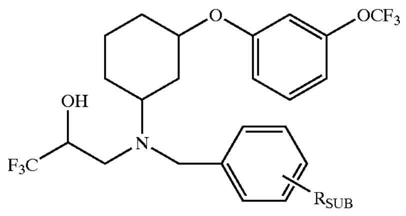 | |
| 399 | 3-$OCF_3$ |
| 400 | 3-$OCF_2CF_2H$ |
| 401 | 2-F, 5-$CF_3$ |
| 402 | 2-F, 4-$CF_3$ |
| 403 | 3-$CF_3$, 4-F |
| 404 | 3-$CF_3CF_2$ |
| 405 | 3-cyclopentyl |
| 406 | 3-isopropoxy |
| 407 | 3-$SCF_3$ |
| 408 | 3-sec-butoxy |
| 409 | 3-$C(CF_3)_2OH$ |
| 410 | 3-(2-furyl) |
| 411 | 3-(3-furyl) |
| 412 | 3-isobutyl |
| 413 | 3-isobutoxy |
| 414 | 3-ethoxy |

EXAMPLE TABLE 5-continued

| Ex. No. | $R_{SUB}$ |
|---|---|
| 415 | 3-$OCH_2CF_3$ |
| 416 | 3-propoxy |
| 417 | 3-tert-butoxy |
| 418 | 3-(2-thienyl) |
| 419 | 3-cyclopropyl |
| 420 | 4-F, 3-(2-furyl) |
| 421 | 3-(3-$CF_3$-phenoxy) |
| 422 | 3,4-($OCF_2CF_2O$) |
| 423 | 3-$OCF_2CF_3$ |
| 424 | 3-cyclopentoxy |
| 425 | 3-(cyclopropyl)methoxy |
| 426 | 3-$OCH_2CH(OH)CF_3$ |
| 427 | 3-$CF_3$ |
| 428 | 4-$CF_3$ |
| 429 | 3-$CH_2CF_2CF_3$ |
| 430 | 3-$CH_2CF_3$ |
| 431 | 3-$CH(CF_3)_2$ |
| 432 | 3-$CF_2CF_2CF_3$ |
| 433 | 3-phenoxy |
| 434 | 3-phenyl |
| 435 | 3-(tetrahydro-2-furyl) |
| 436 | isoamyl |
| 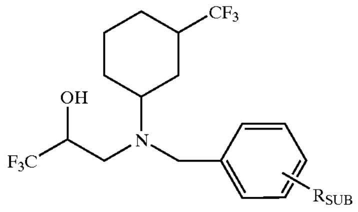 | |
| 437 | 3-$OCF_3$ |
| 438 | 3-$OCF_2CF_2H$ |
| 439 | 2-F, 5-$CF_3$ |
| 440 | 2-F, 4-$CF_3$ |
| 441 | 3-$CF_3$, 4-F |
| 442 | 3-$CF_3CF_2$ |
| 443 | 3-cyclopentyl |
| 444 | 3-isopropoxy |
| 445 | 3-$SCF_3$ |
| 446 | 3-sec-butoxy |
| 447 | 3-$C(CF_3)_2OH$ |
| 448 | 3-(2-furyl) |
| 449 | 3-(3-furyl) |
| 450 | 3-isobutyl |
| 451 | 3-isobutoxy |
| 452 | 3-ethoxy |
| 453 | 3-$OCH_2CF_3$ |
| 454 | 3-propoxy |
| 455 | 3-tert-butoxy |
| 456 | 3-(2-thienyl) |
| 457 | 3-cyclopropyl |
| 458 | 4-F, 3-(2-furyl) |
| 459 | 3-(3-$CF_3$-phenoxy) |
| 460 | 3,4-($OCF_2CF_2O$) |
| 461 | 3-$OCF_2CF_3$ |
| 462 | 3-cyclopentoxy |
| 463 | 3-(cyclopropyl)methoxy |
| 464 | 3-$OCH_2CH(OH)CF_3$ |
| 465 | 3-$CF_3$ |
| 466 | 4-$CF_3$ |
| 467 | 3-$CH_2CF_2CF_3$ |
| 468 | 3-$CH_2CF_3$ |
| 469 | 3-$CH(CF_3)_2$ |
| 470 | 3-$CF_2CF_2CF_3$ |
| 471 | 3-phenoxy |
| 472 | 3-phenyl |
| 473 | 3-(tetrahydro-2-furyl) |
| 474 | isoamyl |

EXAMPLE TABLE 5-continued

| Ex. No. | $R_{SUB}$ |
|---|---|

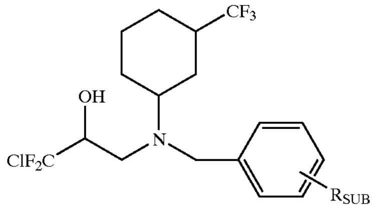

| Ex. No. | $R_{SUB}$ |
|---|---|
| 475 | 3-$OCF_3$ |
| 476 | 3-$OCF_2CF_2H$ |
| 477 | 2-F, 5-$CF_3$ |
| 478 | 2-F, 4-$CF_3$ |
| 479 | 3-$CF_3$, 4-F |
| 480 | 3-$CF_3CF_2$ |
| 481 | 3-cyclopentyl |
| 482 | 3-isopropoxy |
| 483 | 3-$SCF_3$ |
| 484 | 3-sec-butoxy |
| 485 | 3-$C(CF_3)_2OH$ |
| 486 | 3-(2-furyl) |
| 487 | 3-(3-furyl) |
| 488 | 3-isobutyl |
| 489 | 3-isobutoxy |
| 490 | 3-ethoxy |
| 491 | 3-$OCH_2CF_3$ |
| 492 | 3-propoxy |
| 493 | 3-tert-butoxy |
| 494 | 3-(2-thienyl) |
| 495 | 3-cyclopropyl |
| 496 | 4-F, 3-(2-furyl) |
| 497 | 3-(3-$CF_3$-phenoxy) |
| 498 | 3,4-($OCF_2CF_2O$) |
| 499 | 3-$OCF_2CF_3$ |
| 500 | 3-cyclopentoxy |
| 501 | 3-(cyclopropyl)methoxy |
| 502 | 3-$OCH_2CH(OH)CF_3$ |
| 503 | 3-$CF_3$ |
| 504 | 4-$CF_3$ |
| 505 | 3-$CH_2CF_2CF_3$ |
| 506 | 3-$CH_2CF_3$ |
| 507 | 3-$CH(CF_3)_2$ |
| 508 | 3-$CF_2CF_2CF_3$ |
| 509 | 3-phenoxy |
| 510 | 3-phenyl |
| 511 | 3-(tetrahydro-2-furyl) |
| 512 | isoamyl |

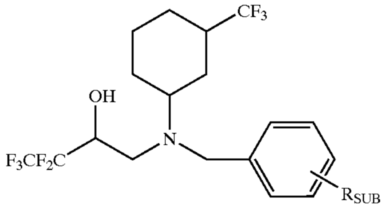

| Ex. No. | $R_{SUB}$ |
|---|---|
| 513 | 3-$OCF_3$ |
| 514 | 3-$OCF_2CF_2H$ |
| 515 | 2-F, 5-$CF_3$ |
| 516 | 2-F, 4-$CF_3$ |
| 517 | 3-$CF_3$, 4-F |
| 518 | 3-$CF_3CF_2$ |
| 519 | 3-cyclopentyl |
| 520 | 3-isopropoxy |
| 521 | 3-$SCF_3$ |
| 522 | 3-sec-butoxy |
| 523 | 3-$C(CF_3)_2OH$ |
| 524 | 3-(2-furyl) |
| 525 | 3-(3-furyl) |
| 526 | 3-isobutyl |
| 527 | 3-isobutoxy |
| 528 | 3-ethoxy |

EXAMPLE TABLE 5-continued

| Ex. No. | $R_{SUB}$ |
|---|---|
| 529 | 3-$OCH_2CF_3$ |
| 530 | 3-propoxy |
| 531 | 3-tert-butoxy |
| 532 | 3-(2-thienyl) |
| 533 | 3-cyclopropyl |
| 534 | 4-F, 3-(2-furyl) |
| 535 | 3-(3-$CF_3$-phenoxy) |
| 536 | 3,4-($OCF_2CF_2O$) |
| 537 | 3-$OCF_2CF_3$ |
| 538 | 3-cyclopentoxy |
| 539 | 3-(cyclopropyl)methoxy |
| 540 | 3-$OCH_2CH(OH)CF_3$ |
| 541 | 3-$CF_3$ |
| 542 | 4-$CF_3$ |
| 543 | 3-$CH_2CF_2CF_3$ |
| 544 | 3-$CH_2CF_3$ |
| 545 | 3-$CH(CF_3)_2$ |
| 546 | 3-$CF_2CF_2CF_3$ |
| 547 | 3-phenoxy |
| 548 | 3-phenyl |
| 549 | 3-(tetrahydro-2-furyl) |
| 550 | isoamyl |

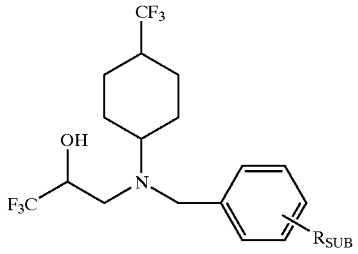

| Ex. No. | $R_{SUB}$ |
|---|---|
| 551 | 3-$OCF_3$ |
| 552 | 3-$OCF_2CF_2H$ |
| 553 | 2-F, 5-$CF_3$ |
| 554 | 2-F, 4-$CF_3$ |
| 555 | 3-$CF_3$, 4-F |
| 556 | 3-$CF_3CF_2$ |
| 557 | 3-cyclopentyl |
| 558 | 3-isopropoxy |
| 559 | 3-$SCF_3$ |
| 560 | 3-sec-butoxy |
| 561 | 3-$C(CF_3)_2OH$ |
| 562 | 3-(2-furyl) |
| 563 | 3-(3-furyl) |
| 564 | 3-isobutyl |
| 565 | 3-isobutoxy |
| 566 | 3-ethoxy |
| 567 | 3-$OCH_2CF_3$ |
| 568 | 3-propoxy |
| 569 | 3-tert-butoxy |
| 570 | 3-(2-thienyl) |
| 571 | 3-cyclopropyl |
| 572 | 4-F, 3-(2-furyl) |
| 573 | 3-(3-$CF_3$-phenoxy) |
| 574 | 3,4-($OCF_2CF_2O$) |
| 575 | 3-$OCF_2CF_3$ |
| 576 | 3-cyclopentoxy |
| 577 | 3-(cyclopropyl)methoxy |
| 578 | 3-$OCH_2CH(OH)CF_3$ |
| 579 | 3-$CF_3$ |
| 580 | 4-$CF_3$ |
| 581 | 3-$CH_2CF_2CF_3$ |
| 582 | 3-$CH_2CF_3$ |
| 583 | 3-$CH(CF_3)_2$ |
| 584 | 3-$CF_2CF_2CF_3$ |
| 585 | 3-phenoxy |
| 586 | 3-phenyl |
| 587 | 3-(tetrahydro-2-furyl) |
| 588 | isoamyl |

EXAMPLE TABLE 5-continued

| Ex. No. | $R_{SUB}$ |
|---|---|
| | 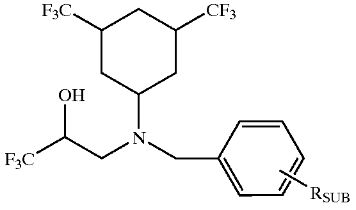 |
| 589 | 3-$OCF_3$ |
| 590 | 3-$OCF_2CF_2H$ |
| 591 | 2-F, 5-$CF_3$ |
| 592 | 2-F, 4-$CF_3$ |
| 593 | 3-$CF_3$, 4-F |
| 594 | 3-$CF_3CF_2$ |
| 595 | 3-cyclopentyl |
| 596 | 3-isopropoxy |
| 597 | 3-$SCF_3$ |
| 598 | 3-sec-butoxy |
| 599 | 3-$C(CF_3)_2OH$ |
| 600 | 3-(2-furyl) |
| 601 | 3-(3-furyl) |
| 602 | 3-isobutyl |
| 603 | 3-isobutoxy |
| 604 | 3-ethoxy |
| 605 | 3-$OCH_2CF_3$ |
| 606 | 3-propoxy |
| 607 | 3-tert-butoxy |
| 608 | 3-(2-thienyl) |
| 609 | 3-cyclopropyl |
| 610 | 4-F, 3-(2-furyl) |
| 611 | 3-(3-$CF_3$-phenoxy) |
| 612 | 3,4-($OCF_2CF_2O$) |
| 613 | 3-$OCF_2CF_3$ |
| 614 | 3-cyclopentoxy |
| 615 | 3-(cyclopropyl)methoxy |
| 616 | 3-$OCH_2CH(OH)CF_3$ |
| 617 | 3-$CF_3$ |
| 618 | 4-$CF_3$ |
| 619 | 3-$CH_2CF_2CF_3$ |
| 620 | 3-$CH_2CF_3$ |
| 621 | 3-$CH(CF_3)_2$ |
| 622 | 3-$CF_2CF_2CF_3$ |
| 623 | 3-phenoxy |
| 624 | 3-phenyl |
| 625 | 3-(tetrahydro-2-furyl) |
| 626 | isoamyl |
| | 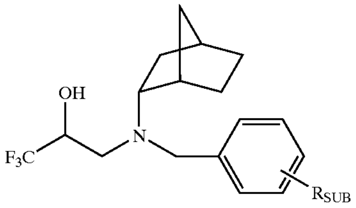 |
| 627 | 3-$OCF_3$ |
| 628 | 3-$OCF_2CF_2H$ |
| 629 | 2-F, $SCF_3$ |
| 630 | 2-F, 4-$CF_3$ |
| 631 | 3-$CF_3$, 4-F |
| 632 | 3-$CF_3CF_2$ |
| 633 | 3-cyclopentyl |
| 634 | 3-isopropoxy |
| 635 | 3-$SCF_3$ |
| 636 | 3-sec-butoxy |
| 637 | 3-$C(CF_3)_2OH$ |
| 638 | 3-(2-furyl) |
| 639 | 3-(3-furyl) |
| 640 | 3-isobutyl |
| 641 | 3-isobutoxy |
| 642 | 3-ethoxy |

EXAMPLE TABLE 5-continued

| Ex. No. | $R_{SUB}$ |
|---|---|
| 643 | 3-$OCH_2CF_3$ |
| 644 | 3-propoxy |
| 645 | 3-tert-butoxy |
| 646 | 3-(2-thienyl) |
| 647 | 3-cyclopropyl |
| 648 | 4-F, 3-(2-furyl) |
| 649 | 3-(3-$CF_3$-phenoxy) |
| 650 | 3,4-($OCF_2CF_2O$) |
| 651 | 3-$OCF_2CF_3$ |
| 652 | 3-cyclopentoxy |
| 653 | 3-(cyclopropyl)methoxy |
| 654 | 3-$OCH_2CH(OH)CF_3$ |
| 655 | 3-$CF_3$ |
| 656 | 4-$CF_3$ |
| 657 | 3-$CH_2CF_2CF_3$ |
| 658 | 3-$CH_2CF_3$ |
| 659 | 3-$CH(CF_3)_2$ |
| 660 | 3-$CF_2CF_2CF_3$ |
| 661 | 3-phenoxy |
| 662 | 3-phenyl |
| 663 | 3-(tetrahydro-2-furyl) |
| 664 | isoamyl |
| | 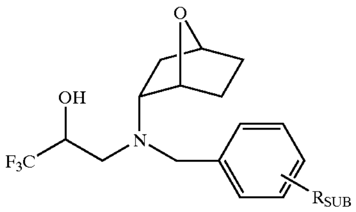 |
| 665 | 3-$OCF_3$ |
| 666 | 3-$OCF_2CF_2H$ |
| 667 | 2-F, 5-$CF_3$ |
| 668 | 2-F, 4-$CF_3$ |
| 669 | 3-$CF_3$, 4-F |
| 670 | 3-$CF_3CF_2$ |
| 671 | 3-cyclopentyl |
| 672 | 3-isopropoxy |
| 673 | 3-$SCF_3$ |
| 674 | 3-sec-butoxy |
| 675 | 3-$C(CF_3)_2OH$ |
| 676 | 3-(2-furyl) |
| 677 | 3-(3-furyl) |
| 678 | 3-isobutyl |
| 679 | 3-isobutoxy |
| 680 | 3-ethoxy |
| 681 | 3-$OCH_2CF_3$ |
| 682 | 3-propoxy |
| 683 | 3-tert-butoxy |
| 684 | 3-(2-thienyl) |
| 685 | 3-cyclopropyl |
| 686 | 4-F, 3-(2-furyl) |
| 687 | 3-(3-$CF_3$-phenoxy) |
| 688 | 3,4-($OCF_2CF_2O$) |
| 689 | 3-$OCF_2CF_3$ |
| 690 | 3-cyclopentoxy |
| 691 | 3-(cyclopropyl)methoxy |
| 692 | 3-$OCH_2CH(OH)CF_3$ |
| 693 | 3-$CF_3$ |
| 694 | 4-$CF_3$ |
| 695 | 3-$CH_2CF_2CF_3$ |
| 696 | 3-$CH_2CF_3$ |
| 697 | 3-$CH(CF_3)_2$ |
| 698 | 3-$CF_2CF_2CF_3$ |
| 699 | 3-phenoxy |
| 700 | 3-phenyl |
| 701 | 3-(tetrahydro-2-furyl) |
| 702 | isoamyl |

EXAMPLE TABLE 5-continued

| Ex. No. | $R_{SUB}$ |
|---|---|

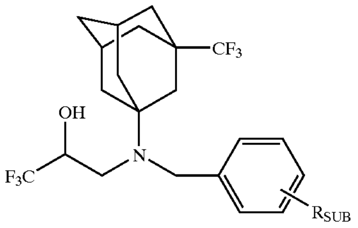

| Ex. No. | $R_{SUB}$ |
|---|---|
| 703 | 3-$OCF_3$ |
| 704 | 3-$OCF_2CF_2H$ |
| 705 | 2-F, $SCF_3$ |
| 706 | 2-F, 4-$CF_3$ |
| 707 | 3-$CF_3$, 4-F |
| 708 | 3-$CF_3CF_2$ |
| 709 | 3-cyclopentyl |
| 710 | 3-isopropoxy |
| 711 | 3-$SCF_3$ |
| 712 | 3-sec-butoxy |
| 713 | 3-$C(CF_3)_2OH$ |
| 714 | 3-(2-furyl) |
| 715 | 3-(3-furyl) |
| 716 | 3-isobutyl |
| 717 | 3-isobutoxy |
| 718 | 3-ethoxy |
| 719 | 3-$OCH_2CF_3$ |
| 720 | 3-propoxy |
| 721 | 3-tert-butoxy |
| 722 | 3-(2-thienyl) |
| 723 | 3-cyclopropyl |
| 724 | 4-F, 3-(2-furyl) |
| 725 | 3-(3-$CF_3$-phenoxy) |
| 726 | 3,4-($OCF_2CF_2O$) |
| 727 | 3-$OCF_2CF_3$ |
| 728 | 3-cyclopentoxy |
| 729 | 3-(cyclopropyl)methoxy |
| 730 | 3-$OCH_2CH(OH)CF_3$ |
| 731 | 3-$CF_3$ |
| 732 | 4-$CF_3$ |
| 733 | 3-$CH_2CF_2CF_3$ |
| 734 | 3-$CH_2CF_3$ |
| 735 | 3-$CH(CF_3)_2$ |
| 736 | 3-$CF_2CF_2CF_3$ |
| 737 | 3-phenoxy |
| 738 | 3-phenyl |
| 739 | 3-(tetrahydro-2-furyl) |
| 740 | isoamyl |

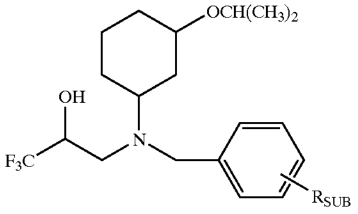

| Ex. No. | $R_{SUB}$ |
|---|---|
| 741 | 3-$OCF_3$ |
| 742 | 3-$OCF_2CF_2H$ |
| 743 | 2-F, 5-$CF_3$ |
| 744 | 2-F, 4-$CF_3$ |
| 745 | 3-$CF_3$, 4-F |
| 746 | 3-$CF_3CF_2$ |
| 747 | 3-cyclopentyl |
| 748 | 3-isopropoxy |
| 749 | 3-$SCF_3$ |
| 750 | 3-sec-butoxy |
| 751 | 3-$C(CF_3)_2OH$ |
| 752 | 3-(2-furyl) |
| 753 | 3-(3-furyl) |
| 754 | 3-isobutyl |
| 755 | 3-isobutoxy |

EXAMPLE TABLE 5-continued

| Ex. No. | $R_{SUB}$ |
|---|---|
| 756 | 3-ethoxy |
| 757 | 3-$OCH_2CF_3$ |
| 758 | 3-propoxy |
| 759 | 3-tert-butoxy |
| 760 | 3-(2-thienyl) |
| 761 | 3-cyclopropyl |
| 762 | 4-F, 3-(2-furyl) |
| 763 | 3-(3-$CF_3$-phenoxy) |
| 764 | 3,4-($OCF_2CF_2O$) |
| 765 | 3-$OCF_2CF_3$ |
| 766 | 3-cyclopentoxy |
| 767 | 3-(cyclopropyl)methoxy |
| 768 | 3-$OCH_2CH(OH)CF_3$ |
| 769 | 3-$CF_3$ |
| 770 | 4-$CF_3$ |
| 771 | 3-$CH_2CF_2CF_3$ |
| 772 | 3-$CH_2CF_3$ |
| 773 | 3-$CH(CF_3)_2$ |
| 774 | 3-$CF_2CF_2CF_3$ |
| 775 | 3-phenoxy |
| 776 | 3-phenyl |
| 777 | 3-(tetrahydro-2-furyl) |
| 778 | isoamyl |

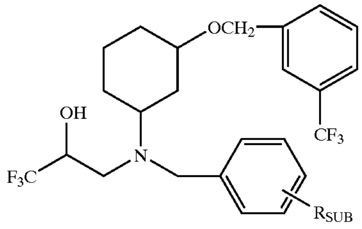

| Ex. No. | $R_{SUB}$ |
|---|---|
| 779 | 3-$OCF_3$ |
| 780 | 3-$OCF_2CF_2H$ |
| 781 | 2-F, 5-$CF_3$ |
| 782 | 2-F, 4-$CF_3$ |
| 783 | 3-$CF_3$, 4-F |
| 784 | 3-$CF_3CF_2$ |
| 785 | 3-cyclopentyl |
| 786 | 3-isopropoxy |
| 787 | 3-$SCF_3$ |
| 788 | 3-sec-butoxy |
| 789 | 3-$C(CF_3)_2OH$ |
| 790 | 3-(2-furyl) |
| 791 | 3-(3-furyl) |
| 792 | 3-isobutyl |
| 793 | 3-isobutoxy |
| 794 | 3-ethoxy |
| 795 | 3-$OCH_2CF_3$ |
| 796 | 3-propoxy |
| 797 | 3-tert-butoxy |
| 798 | 3-(2-thienyl) |
| 799 | 3-cyclopropyl |
| 800 | 4-F, 3-(2-furyl) |
| 801 | 3-(3-$CF_3$-phenoxy) |
| 802 | 3,4-($OCF_2CF_2O$) |
| 803 | 3-$OCF_2CF_3$ |
| 804 | 3-cyclopentoxy |
| 805 | 3-(cyclopropyl)methoxy |
| 806 | 3-$OCH_2CH(OH)CF_3$ |
| 807 | 3-$CF_3$ |
| 808 | 4-$CF_3$ |
| 809 | 3-$CH_2CF_2CF_3$ |
| 810 | 3-$CH_2CF_3$ |
| 811 | 3-$CH(CF_3)_2$ |
| 812 | 3-$CF_2CF_2CF_3$ |
| 813 | 3-phenoxy |
| 814 | 3-phenyl |
| 815 | 3-(tetrahydro-2-furyl) |
| 816 | isoamyl |

EXAMPLE TABLE 5-continued

| Ex. No. | $R_{SUB}$ |
|---|---|
| 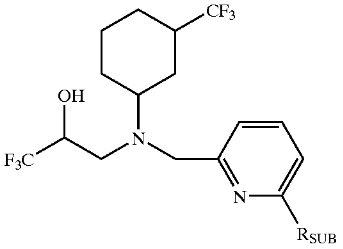 | |
| 817 | $OCF_3$ |
| 818 | $OCF_2CF_2H$ |
| 819 | $OCF_2CF_3$ |
| 820 | $CH_2CF_3$ |
| 821 | $CF_3$ |
| 822 | $CF_3CF_2$ |
| 823 | cyclopentyl |
| 824 | isopropoxy |
| 825 | $SCF_3$ |
| 826 | sec-butoxy |
| 827 | $C(CF_3)_2OH$ |
| 828 | (2-furyl) |
| 829 | (3-furyl) |
| 830 | isobutyl |
| 831 | isobutoxy |
| 832 | ethoxy |
| 833 | $OCH_2CF_3$ |
| 834 | (2-thienyl) |
| 835 | cyclopropyl |
| 836 | (3-$CF_3$-phenoxy) |
| 837 | cyclopentoxy |
| 838 | (cyclopropyl)methoxy |
| 839 | $OCH_2CH(OH)CF_3$ |
| 840 | $CH_2CF_2CF_3$ |
| 841 | $CH(CF_3)_2$ |
| 842 | $CH(CF_3)_2$ |
| 843 | $CF_2CF_2CF_3$ |
| 844 | phenoxy |
| 845 | phenyl |
| 846 | (tetrahydro-2-furyl) |
| 847 | isoamyl |
| 848 | propoxy |
| 849 | tert-butoxy |
| 850 | (2-pyridyl) |

EXAMPLE TABLE 5-continued

| Ex. No. | $R_{SUB}$ |
|---|---|
| 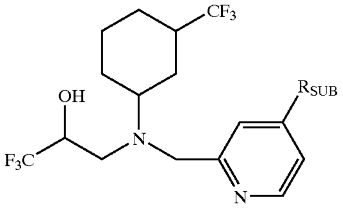 | |
| 851 | $OCF_3$ |
| 852 | $OCF_2CF_2H$ |
| 853 | $OCF_2CF_3$ |
| 854 | $CH_2CF_3$ |
| 855 | $CF_3$ |
| 856 | $CF_3CF_2$ |
| 857 | cyclopentyl |
| 858 | isopropoxy |
| 859 | $SCF_3$ |
| 860 | sec-butoxy |
| 861 | $C(CF_3)_2OH$ |
| 862 | (2-furyl) |
| 863 | (3-furyl) |
| 864 | isobutyl |
| 865 | isobutoxy |
| 866 | ethoxy |
| 867 | $OCH_2CF_3$ |
| 868 | (2-thienyl) |
| 869 | cyclopropyl |
| 870 | (3-$CF_3$-phenoxy) |
| 871 | cyclopentoxy |
| 872 | (cyclopropyl)methoxy |
| 873 | $OCH_2CH(OH)CF_3$ |
| 874 | $CH_2CF_2CF_3$ |
| 875 | $CH(CF_3)_2$ |
| 876 | $CH(CF_3)_2$ |
| 877 | $CF_2CF_2CF_3$ |
| 878 | phenoxy |
| 879 | phenyl |
| 880 | (tetrahydro-2-furyl) |
| 881 | isoamyl |
| 882 | propoxy |
| 883 | tert-butoxy |
| 884 | (2-pyridyl) |

EXAMPLE TABLE 6

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 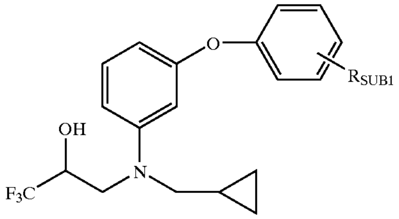 | | 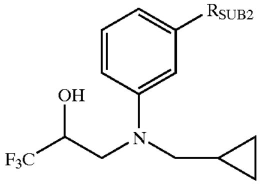 | |
| 885 | 3-isopropyl | 909 | 3-$CF_3O$-benzyloxy |

EXAMPLE TABLE 6-continued

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 886 | 2-Cl, 3-Cl | 910 | 3-$CF_3$-benzyloxy |
| 887 | 3-$CF_3O$ | 911 | 3-F, 5-F-benzyloxy |
| 888 | 4-F | 912 | cyclohexylmethyleneoxy |
| 889 | 4-$CH_3$ | 913 | benzyloxy |
| 890 | 2-F, 5-Br | 914 | 3-$CF_3$, 5-$CF_3$-benzyloxy |
| 891 | 4-Cl, 3-$CH_3CH_2$ | 915 | 4-$CF_3O$-benzyloxy |
| 892 | 3-$CH_3CH_2$ | 916 | 4-$CH_3CH_2$-benzyloxy |
| 893 | 3-$CH_3$, 5-$CH_3$ | 917 | isopropoxy |
| 894 | 3-$(CH_3)_3C$ | 918 | 3-$CF_3$-benzyl |
| 895 | 4-F, 3-$CH_3$ | 919 | isopropylthio |
| 896 | 3-Cl, 4-Cl | 920 | cyclopentoxy |
| 897 | 3,4-$(CH_2)_4$ | 921 | 3-Cl-5-pyridinyloxy |
| 898 | 3-$HCF_2CF_2O$ | 922 | 3-$CF_3S$-benzyloxy |
| 899 | 3-$CHF_2O$ | 923 | 3-$CH_3$, 4-$CH_3$-benzyloxy |
| 900 | 3-$(CH_3)_2N$ | 924 | 2-F, 3-$CF_3$-benzyloxy |
| 901 | 3-cyclopropyl | 925 | 3-F, 5-$CF_3$-benzyloxy |
| 902 | 3-(2-furyl) | 926 | 4-$(CH_3)_2CH$-benzyloxy |
| 903 | 3-$CF_3CF_2$ | 927 | 1-phenylethoxy |
| 904 | 4-$NH_2$ | 928 | 4-F, 3-$CH_3$-benzoyl |
| 905 | 3-$CH_3$, 4-$CH_3$, 5-$CH_3$ | 929 | 3-$CF_3$-phenyl |
| 906 | 4-$CH_3CH_2CH_2O$ | 930 | 4-$CH_3O$-phenylamino |
| 907 | 3-$CF_3$ | 931 | cyclopropoxy |
| 908 | 2-$NO_2$ | 932 | 4-$NO_2$-phenylthio |

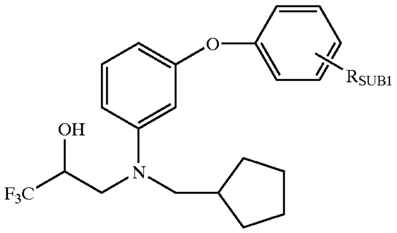

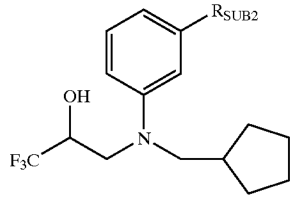

| Ex. No. | $R_{SUB1}$ | Ex. No. | $R_{SUB2}$ |
|---|---|---|---|
| 933 | 3-isopropyl | 957 | 3-$CF_3O$-benzyloxy |
| 934 | 2-Cl, 3-Cl | 958 | 3-$CF_3$-benzyloxy |
| 935 | 3-$CF_3O$ | 959 | 5-F-benzyloxy |
| 936 | 4-F | 960 | cyclohexylmethyleneoxy |
| 937 | 4-$CH_3$ | 961 | benzyloxy |
| 938 | 2-F, 5-Br | 962 | 3-$CF_3$, 5-$CF_3$-benzyloxy |
| 939 | 4-Cl, 3-$CH_3CH_2$ | 963 | 4-$CF_3O$-benzyloxy |
| 940 | 3-$CH_3CH_2$ | 964 | 4-$CH_3CH_2$-benzyloxy |
| 941 | 3-$CH_3$, 5-$CH_3$ | 965 | isopropoxy |
| 942 | 3-$(CH_3)_3C$ | 966 | 3-$CF_3$-benzyl |
| 943 | 4-F, 3-$CH_3$ | 967 | isopropylthio |
| 944 | 3-Cl, 4-Cl | 968 | cyclopentoxy |
| 945 | 3,4-$(CH_2)_4$ | 969 | 3-Cl-5-pyridinyloxy |
| 946 | 3-$HCF_2CF_2O$ | 970 | 3-$CF_3S$-benzyloxy |
| 947 | 3-$CHF_2O$ | 971 | 3-$CH_3$, 4-$CH_3$-benzyloxy |
| 948 | 3-$(CH_3)_2N$ | 972 | 2-F, 3-$CF_3$-benzyloxy |
| 949 | 3-cyclopropyl | 973 | 3-F, 5-$CF_3$-benzyloxy |
| 950 | 3-(2-furyl) | 974 | 4-$(CH_3)_2CH$-benzyloxy |
| 951 | 3-$CF_3CF_2$ | 975 | 1-phenylethoxy |
| 952 | 4-$NH_2$ | 976 | 4-F, 3-$CH_3$-benzoyl |
| 953 | 3-$CH_3$, 4-$CH_3$, 5-$CH_3$ | 977 | 3-$CF_3$-phenyl |
| 954 | 4-$CH_3CH_2CH_2O$ | 978 | 4-$CH_3O$-phenylamino |
| 955 | 3-$CF_3$ | 979 | cyclopropoxy |
| 956 | 2-$NO_2$ | 980 | 4-$NO_2$-phenylthio |

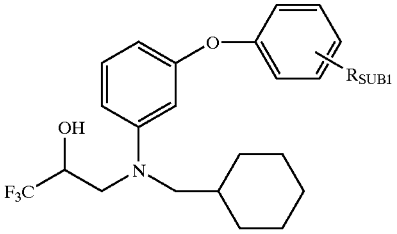

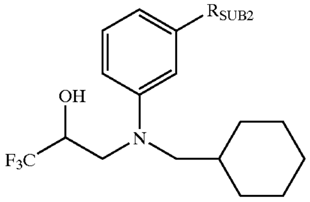

| Ex. No. | $R_{SUB1}$ | Ex. No. | $R_{SUB2}$ |
|---|---|---|---|
| 981 | 3-isopropyl | 1005 | 3-$CF_3O$-benzyloxy |
| 982 | 2-Cl, 3-Cl | 1006 | 3-$CF_3$-benzyloxy |

EXAMPLE TABLE 6-continued

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 983 | 3-$CF_3O$ | 1007 | 3-F, 5-F-benzyloxy |
| 984 | 4-F | 1008 | cyclohexylmethyleneoxy |
| 985 | 4-$CH_3$ | 1009 | benzyloxy |
| 986 | 2-F, 5-Br | 1010 | 3-$CF_3$, 5-$CF_3$-benzyloxy |
| 987 | 4-F, 3-$CF_3$ | 1011 | 4-$CF_3O$-benzyloxy |
| 988 | 3-$CH_3CH_2$ | 1012 | 4-$CH_3CH_2$-benzyloxy |
| 989 | 3-$CH_3$, 5-$CH_3$ | 1013 | isopropoxy |
| 990 | 3-$(CH_3)_3C$ | 1014 | 3-$CF_3$-benzyl |
| 991 | 4-F, 3-$CH_3$ | 1015 | isopropylthio |
| 992 | 3-Cl, 4-Cl | 1016 | cyclopentoxy |
| 993 | 3,4-$(CH_2)_4$ | 1017 | 3-Cl-5-pyridinyloxy |
| 994 | 3-$HCF_2CF_2O$ | 1018 | 3-$CF_3S$-benzyloxy |
| 995 | 3-$CHF_2O$ | 1019 | 3-$CH_3$, 4-$CH_3$-benzyloxy |
| 996 | 3-$(CH_3)_2N$ | 1020 | 2-F, 3-$CF_3$-benzyloxy |
| 997 | 3-cyclopropyl | 1021 | 3-F, 5-$CF_3$-benzyloxy |
| 998 | 3-(2-furyl) | 1022 | 4-$(CH_3)_2CH$-benzyloxy |
| 999 | 3-$CF_3CF_2$ | 1023 | 1-phenylethoxy |
| 1000 | 4-$NH_2$ | 1024 | 4-F, 3-$CH_3$-benzoyl |
| 1001 | 3-$CH_3$, 4-$CH_3$, 5-$CH_3$ | 1025 | 3-$CF_3$-phenyl |
| 1002 | 4-$CH_3CH_2CH_2O$ | 1026 | 4-$CH_3O$-phenylamino |
| 1003 | 3-$CF_3$ | 1027 | cyclopropoxy |
| 1004 | 2-$NO_2$ | 1028 | 4-$NO_2$-phenylthio |

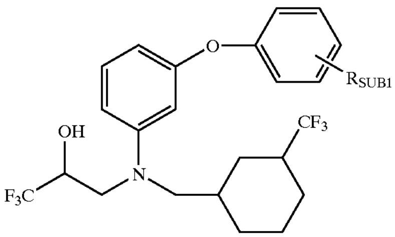

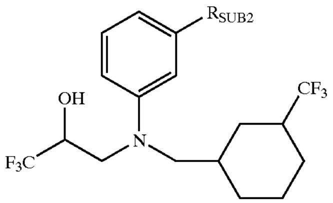

| Ex. No. | $R_{SUB1}$ | Ex. No. | $R_{SUB2}$ |
|---|---|---|---|
| 1029 | 3-isopropyl | 1053 | 3-$CF_3O$-benzyloxy |
| 1030 | 2-Cl, 3-Cl | 1054 | 3-$CF_3$-benzyloxy |
| 1031 | 3-$CF_3O$ | 1055 | 3-F, 5-F-benzyloxy |
| 1032 | 4-F | 1056 | cyclohexylmethyleneoxy |
| 1033 | 4-$CH_3$ | 1057 | benzyloxy |
| 1034 | 2-F, 5-Br | 1058 | 3-$CF_3$, 5-$CF_3$-benzyloxy |
| 1035 | 4-Cl, 3-$CH_3CH_2$ | 1059 | 4-$CF_3O$-benzyloxy |
| 1036 | 3-$CH_3CH_2$ | 1060 | 4-$CH_3CH_2$-benzyloxy |
| 1037 | 3-$CH_3$, 5-$CH_3$ | 1061 | isopropoxy |
| 1038 | 3-$(CH_3)_3C$ | 1062 | 3-$CF_3$-benzyl |
| 1039 | 4-F, 3-$CH_3$ | 1063 | isopropylthio |
| 1040 | 3-Cl, 4-Cl | 1064 | cyclopentoxy |
| 1041 | 3,4-$(CH_2)_4$ | 1065 | 3-Cl-5-pyridinyloxy |
| 1042 | 3-$HCF_2CF_2O$ | 1066 | 3-$CF_3S$-benzyloxy |
| 1043 | 3-$CHF_2O$ | 1067 | 3-$CH_3$, 4-$CH_3$-benzyloxy |
| 1044 | 3-$(CH_3)_2N$ | 1068 | 2-F, 3-$CF_3$-benzyloxy |
| 1045 | 3-cyclopropyl | 1069 | 3-F, 5-$CF_3$-benzyloxy |
| 1046 | 3-(2-furyl) | 1070 | 4-$(CH_3)_2CH$-benzyloxy |
| 1047 | 3-$CF_3CF_2$ | 1071 | 1-phenylethoxy |
| 1048 | 4-$NH_2$ | 1072 | 4-F, 3-$CH_3$-benzoyl |
| 1049 | 3-$CH_3$, 4-$CH_3$, 5-$CH_3$ | 1073 | 3-$CF_3$-phenyl |
| 1050 | 4-$CH_3CH_2CH_2O$ | 1074 | 4-$CH_3O$-phenylamino |
| 1051 | 3-$CF_3$ | 1075 | cyclopropoxy |
| 1052 | 2-$NO_2$ | 1076 | 4-$NO_2$-phenylthio |

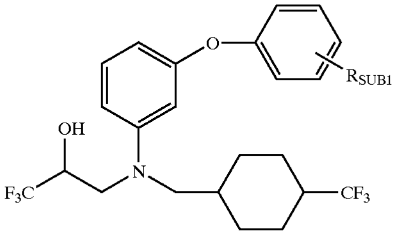

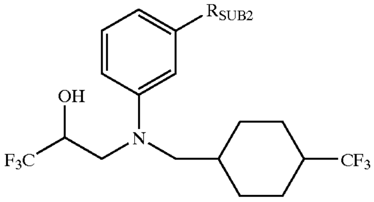

| Ex. No. | $R_{SUB1}$ | Ex. No. | $R_{SUB2}$ |
|---|---|---|---|
| 1077 | 3-isopropyl | 1101 | 3-$CF_3O$-benzyloxy |
| 1078 | 2-Cl, 3-Cl | 1102 | 3-$CF_3$-benzyloxy |

EXAMPLE TABLE 6-continued

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 1079 | $3-CF_3O$ | 1103 | 3-F, 5-F-benzyloxy |
| 1080 | 4-F | 1104 | cyclohexylmethyleneoxy |
| 1081 | $4-CH_3$ | 1105 | benzyloxy |
| 1082 | 2-F, 5-Br | 1106 | $3-CF_3$, $5-CF_3$-benzyloxy |
| 1083 | 4-Cl, $3-CH_3CH_2$ | 1107 | $4-CF_3O$-benzyloxy |
| 1084 | $3-CH_3CH_2$ | 1108 | $4-CH_3CH_2$-benzyloxy |
| 1085 | $3-CH_3$, $5-CH_3$ | 1109 | isopropoxy |
| 1086 | $3-(CH_3)_3C$ | 1110 | $3-CF_3$-benzyl |
| 1087 | 4-F, $3-CH_3$ | 1111 | isopropylthio |
| 1088 | 3-Cl, 4-Cl | 1112 | cyclopentoxy |
| 1089 | $3,4-(CH_2)_4$ | 1113 | 3-Cl-5-pyridinyloxy |
| 1090 | $3-HCF_2CF_2O$ | 1114 | $3-CF_3S$-benzyloxy |
| 1091 | $3-CHF_2O$ | 1115 | $3-CH_3$, $4-CH_3$-benzyloxy |
| 1092 | $3-(CH_3)_2N$ | 1116 | 2-F, $3-CF_3$-benzyloxy |
| 1093 | 3-cyclopropyl | 1117 | 3-F, $5-CF_3$-benzyloxy |
| 1094 | 3-(2-furyl) | 1118 | $4-(CH_3)_2CH$-benzyloxy |
| 1095 | $3-CF_3CF_2$ | 1119 | 1-phenylethoxy |
| 1096 | $4-NH_2$ | 1120 | 4-F, $3-CH_3$-benzoyl |
| 1097 | $3-CH_3$, $4-CH_3$, $5-CH_3$ | 1121 | $3-CF_3$-phenyl |
| 1098 | $4-CH_3CH_2CH_2O$ | 1122 | $4-CH_3O$-phenylamino |
| 1099 | $3-CF_3$ | 1123 | cyclopropoxy |
| 1100 | $2-NO_2$ | 1124 | $4-NO_2$-phenylthio |

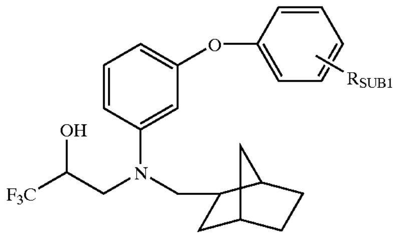

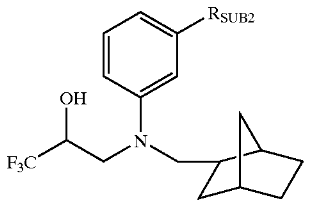

| Ex. No. | $R_{SUB1}$ | Ex. No. | $R_{SUB2}$ |
|---|---|---|---|
| 1125 | 3-isopropyl | 1149 | $3-CF_3O$-benzyloxy |
| 1126 | 2-Cl, 3-Cl | 1150 | $3-CF_3$-benzyloxy |
| 1127 | $3-CF_3O$ | 1151 | 3-F, 5-F-benzyloxy |
| 1128 | 4-F | 1152 | cyclohexylmethyleneoxy |
| 1129 | $4-CH_3$ | 1153 | benzyloxy |
| 1130 | 2-F, 5-Br | 1154 | $3-CF_3$, $5-CF_3$-benzyloxy |
| 1131 | 4-Cl, $3-CH_3CH_2$ | 1155 | $4-CF_3O$-benzyloxy |
| 1132 | $3-CH_3CH_2$ | 1156 | $4-CH_3CH_2$-benzyloxy |
| 1133 | $3-CH_3$, $5-CH_3$ | 1157 | isopropoxy |
| 1134 | $3-(CH_3)_3C$ | 1158 | $3-CF_3$-benzyl |
| 1135 | 4-F, $3-CH_3$ | 1159 | isopropylthio |
| 1136 | 3-Cl, 4-Cl | 1160 | cyclopentoxy |
| 1137 | $3,4-(CH_2)_4$ | 1161 | 3-Cl-5-pyridinyloxy |
| 1138 | $3-HCF_2CF_2O$ | 1162 | $3-CF_3S$-benzyloxy |
| 1139 | $3-CHF_2O$ | 1163 | $3-CH_3$, $4-CH_3$-benzyloxy |
| 1140 | $3-(CH_3)_2N$ | 1164 | 2-F, $3-CF_3$-benzyloxy |
| 1141 | 3-cyclopropyl | 1165 | 3-F, $5-CF_3$-benzyloxy |
| 1142 | 3-(2-furyl) | 1166 | $4-(CH_3)_2CH$-benzyloxy |
| 1143 | $3-CF_3CF_2$ | 1167 | 1-phenylethoxy |
| 1144 | $4-NH_2$ | 1168 | 4-F, $3-CH_3$-benzoyl |
| 1145 | $3-CH_3$, $4-CH_3$, $5-CH_3$ | 1169 | $3-CF_3$-phenyl |
| 1146 | $4-CH_3CH_2CH_2O$ | 1170 | $4-CH_3O$-phenylamino |
| 1147 | $3-CF_3$ | 1171 | cyclopropoxy |
| 1148 | $2-NO_2$ | 1172 | $4-NO_2$-phenylthio |

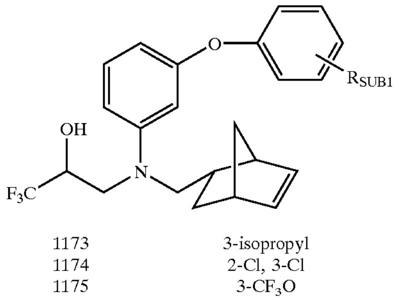

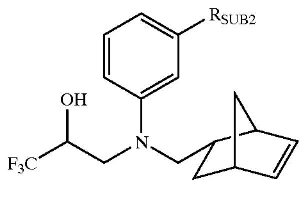

| Ex. No. | $R_{SUB1}$ | Ex. No. | $R_{SUB2}$ |
|---|---|---|---|
| 1173 | 3-isopropyl | 1197 | $3-CF_3O$-benzyloxy |
| 1174 | 2-Cl, 3-Cl | 1198 | $3-CF_3$-benzyloxy |
| 1175 | $3-CF_3O$ | 1199 | 3-F, 5-F-benzyloxy |
| 1176 | 4-F | 1200 | cyclohexylmethyleneoxy |

EXAMPLE TABLE 6-continued

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 1177 | 4-$CH_3$ | 1201 | benzyloxy |
| 1178 | 2-F, 5-Br | 1202 | 3-$CF_3$, 5-$CF_3$-benzyloxy |
| 1179 | 4-Cl, 3-$CH_3CH_2$ | 1203 | 4-$CF_3O$-benzyloxy |
| 1180 | 3-$CH_3CH_2$ | 1204 | 4-$CH_3CH_2$-benzyloxy |
| 1181 | 3-$CH_3$, 5-$CH_3$ | 1205 | isopropoxy |
| 1182 | 3-$(CH_3)_3C$ | 1206 | 3-$CF_3$-benzyl |
| 1183 | 4-F, 3-$CH_3$ | 1207 | isopropylthio |
| 1184 | 3-Cl, 4-Cl | 1208 | cyclopentoxy |
| 1185 | 3,4-$(CH_2)_4$ | 1209 | 3-Cl-5-pyridinyloxy |
| 1186 | 3-$HCF_2CF_2O$ | 1210 | 3-$CF_3S$-benzyloxy |
| 1187 | 3-$CHF_2O$ | 1211 | 3-$CH_3$, 4-$CH_3$-benzyloxy |
| 1188 | 3-$(CH_3)_2N$ | 1212 | 2-F, 3-$CF_3$-benzyloxy |
| 1189 | 3-cyclopropyl | 1213 | 3-F, 5-$CF_3$-benzyloxy |
| 1190 | 3-(2-furyl) | 1214 | 4-$(CH_3)_2CH$-benzyloxy |
| 1191 | 3-$CF_3CF_2$ | 1215 | 1-phenylethoxy |
| 1192 | 4-$NH_2$ | 1216 | 4-F, 3-$CH_3$-benzoyl |
| 1193 | 3-$CH_3$, 4-$CH_3$, 5-$CH_3$ | 1217 | 3-$CF_3$-phenyl |
| 1194 | 4-$CH_3CH_2CH_2O$ | 1218 | 4-$CH_3O$-phenylamino |
| 1195 | 3-$CF_3$ | 1219 | cyclopropoxy |
| 1196 | 2-$NO_2$ | 1220 | 4-$NO_2$-phenylthio |

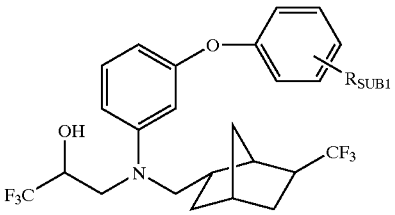

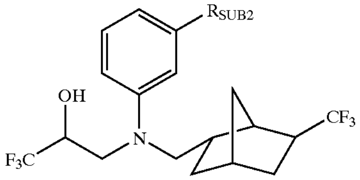

| Ex. No. | $R_{SUB1}$ | Ex. No. | $R_{SUB2}$ |
|---|---|---|---|
| 1221 | 3-isopropyl | 1245 | 3-$CF_3O$-benzyloxy |
| 1222 | 2-Cl, 3-Cl | 1246 | 3-$CF_3$-benzyloxy |
| 1223 | 3-$CF_3O$ | 1247 | 3-F, 5-F-benzyloxy |
| 1224 | 4-F | 1248 | cyclohexylmethyleneoxy |
| 1225 | 4-$CH_3$ | 1249 | benzyloxy |
| 1226 | 2-F, 5-Br | 1250 | 3-$CF_3$, 5-$CF_3$-benzyloxy |
| 1227 | 4-Cl, 3-$CH_3CH_2$ | 1251 | 4-$CF_3O$-benzyloxy |
| 1228 | 3-$CH_3CH_2$ | 1252 | 4-$CH_3CH_2$-benzyloxy |
| 1229 | 3-$CH_3$, 5-$CH_3$ | 1253 | isopropoxy |
| 1230 | 3-$(CH_3)_3C$ | 1254 | 3-$CF_3$-benzyl |
| 1231 | 4-F, 3-$CH_3$ | 1255 | isopropylthio |
| 1232 | 3-Cl, 4-Cl | 1256 | cyclopentoxy |
| 1233 | 3,4-$(CH_2)_4$ | 1257 | 3-Cl-5-pyridinyloxy |
| 1234 | 3-$HCF_2CF_2O$ | 1258 | 3-$CF_3S$-benzyloxy |
| 1235 | 3-$CHF_2O$ | 1259 | 3-$CH_3$, 4-$CH_3$-benzyloxy |
| 1236 | 3-$(CH_3)_2N$ | 1260 | 2-F, 3-$CF_3$-benzyloxy |
| 1237 | 3-cyclopropyl | 1261 | 3-F, 5-$CF_3$-benzyloxy |
| 1238 | 3-(2-furyl) | 1262 | 4-$(CH_3)_2CH$-benzyloxy |
| 1239 | 3-$CF_3CF_2$ | 1263 | 1-phenylethoxy |
| 1240 | 4-$NH_2$ | 1264 | 4-F, 3-$CH_3$-benzoyl |
| 1241 | 3-$CH_3$, 4-$CH_3$, 5-$CH_3$ | 1265 | 3-$CF_3$-phenyl |
| 1242 | 4-$CH_3CH_2CH_2O$ | 1266 | 4-$CH_3O$-phenylamino |
| 1243 | 3-$CF_3$ | 1267 | cyclopropoxy |
| 1244 | 2-$NO_2$ | 1268 | 4-$NO_2$-phenylthio |

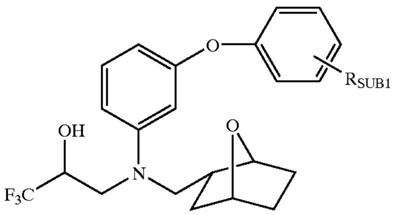

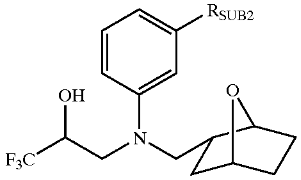

| Ex. No. | $R_{SUB1}$ | Ex. No. | $R_{SUB2}$ |
|---|---|---|---|
| 1269 | 3-isopropyl | 1293 | 3-$CF_3O$-benzyloxy |
| 1270 | 2-Cl, 3-Cl | 1294 | 3-$CF_3$-benzyloxy |
| 1271 | 3-$CF_3O$ | 1295 | 3-F, 5-F-benzyloxy |
| 1272 | 4-F | 1296 | cyclohexylmethyleneoxy |
| 1273 | 4-$CH_3$ | 1297 | benzyloxy |
| 1274 | 2-F, 5-Br | 1298 | 3-$CF_3$, 5-$CF_3$-benzyloxy |
| 1275 | 4-Cl, 3-$CH_3CH_2$ | 1299 | 4-$CF_3O$-benzyloxy |

EXAMPLE TABLE 6-continued

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 1276 | $3-CH_3CH_2$ | 1300 | $4-CH_3CH_2$-benzyloxy |
| 1277 | $3-CH_3$, $5-CH_3$ | 1301 | isoproxy |
| 1278 | $3-(CH_3)_3C$ | 1302 | $3-CF_3$-benzyl |
| 1279 | 4-F, $3-CH_3$ | 1303 | isopropylthio |
| 1280 | 3-Cl, 4-Cl | 1304 | cyclopentoxy |
| 1281 | $3,4-(CH_2)_4$ | 1305 | 3-Cl-5-pyridinyloxy |
| 1282 | $3-HCF_2CF_2O$ | 1306 | $3-CF_3S$-benzyloxy |
| 1283 | $3-CHF_2O$ | 1307 | $3-CH_3$, $4-CH_3$-benzyloxy |
| 1284 | $3-(CH_3)_2N$ | 1308 | 2-F, $3-CF_3$-benzyloxy |
| 1285 | 3-cyclopropyl | 1309 | 3-F, $5-CF_3$-benzyloxy |
| 1286 | 3-(2-furyl) | 1310 | $4-(CH_3)_2CH$-benzyloxy |
| 1287 | $3-CF_3CF_2$ | 1311 | 1-phenylethoxy |
| 1288 | $4-NH_2$ | 1312 | 4-F, $3-CH_3$-benzoyl |
| 1289 | $3-CH_3$, $4-CH_3$, $5-CH_3$ | 1313 | $3-CF_3$-phenyl |
| 1290 | $4-CH_3CH_2CH_2O$ | 1314 | $4-CH_3O$-phenylamino |
| 1291 | $3-CF_3$ | 1315 | cyclopropoxy |
| 1292 | $2-NO_2$ | 1316 | $4-NO_2$-phenylthio |

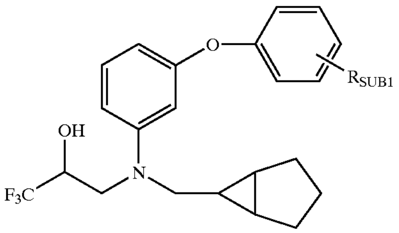

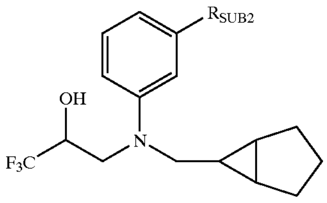

| | | | |
|---|---|---|---|
| 1317 | 3-isopropyl | 1341 | $3-CF_3O$-benzyloxy |
| 1318 | 2-Cl, 3-Cl | 1342 | $3-CF_3$-benzyloxy |
| 1319 | $3-CF_3O$ | 1343 | 3-F, 5-F-benzyloxy |
| 1320 | 4-F | 1344 | cyclohexylmethyleneoxy |
| 1321 | $4-CH_3$ | 1345 | benzyloxy |
| 1322 | 2-F, 5-Br | 1346 | $3-CH_3$, $5-CF_3$-benzyloxy |
| 1323 | 4-Cl, $3-CH_3CH_2$ | 1347 | $4-CF_3O$-benzyloxy |
| 1324 | $3-CH_3CH_2$ | 1348 | $4-CH_3CH_2$-benzyloxy |
| 1325 | $3-CH_3$, $5-CH_3$ | 1349 | isopropoxy |
| 1326 | $3-(CH_3)_3C$ | 1350 | $3-CF_3$-benzyl |
| 1327 | 4-F, $3-CH_3$ | 1351 | isopropylthio |
| 1328 | 3-Cl, 4-Cl | 1352 | cyclopentoxy |
| 1329 | $3,4-(CH_2)_4$ | 1353 | 3-Cl-5-pyridinyloxy |
| 1330 | $3-HCF_2CF_2O$ | 1354 | $3-CF_3S$-benzyloxy |
| 1331 | $3-CHF_2O$ | 1355 | $3-CH_3$, $4-CH_3$-benzyloxy |
| 1332 | $3-(CH_3)_2N$ | 1356 | 2-F, $3-CF_3$-benzyloxy |
| 1333 | 3-cyclopropyl | 1357 | 3-F, $5-CF_3$-benzyloxy |
| 1334 | 3-(2-furyl) | 1358 | $4-(CH_3)_2CH$-benzyloxy |
| 1335 | $3-CF_3CF_2$ | 1359 | 1-phenylethoxy |
| 1336 | $4-NH_2$ | 1360 | 4-F, $3-CH_3$-benzoyl |
| 1337 | $3-CH_3$, $4-CH_3$, $5-CH_3$ | 1361 | $3-CF_3$-phenyl |
| 1338 | $4-CH_3CH_2CH_2O$ | 1362 | $4-CH_3O$-phenylamino |
| 1339 | $3-CF_3$ | 1363 | cyclopropoxy |
| 1340 | $2-NO_2$ | 1364 | $4-NO_2$-phenylthio |

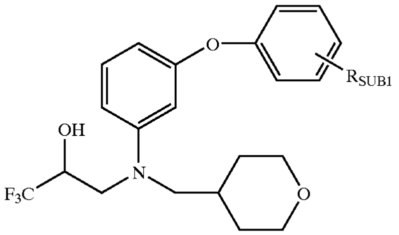

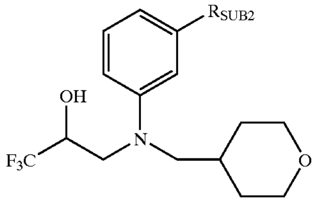

| | | | |
|---|---|---|---|
| 1365 | 3-isopropyl | 1389 | $3-CF_3O$-benzyloxy |
| 1366 | 2-Cl, 3-Cl | 1390 | $3-CF_3$-benzyloxy |
| 1367 | $3-CF_3O$ | 1391 | 3-F, 5-F-benzyloxy |
| 1368 | 4-F | 1392 | cyclohexylmethyleneoxy |
| 1369 | $4-CH_3$ | 1393 | benzyloxy |
| 1370 | 2-F, 5-Br | 1394 | $3-CF_3$, $5-CF_3$-benzyloxy |
| 1371 | 4-Cl, $3-CH_3CH_2$ | 1395 | $4-CF_3O$-benzyloxy |
| 1372 | $3-CH_3CH_2$ | 1396 | $4-CH_3CH_2$-benzyloxy |

EXAMPLE TABLE 6-continued

3-[(N-aryl)[[cycloalkyl]methyl]amino]-halo-2-propanols.

| Ex. No. | $R_{SUB1}$ | Ex. No. | $R_{SUB2}$ |
|---|---|---|---|
| 1373 | 3-$CH_3$, 5-$CH_3$ | 1397 | isopropoxy |
| 1374 | 3-$(CH_3)_3C$ | 1398 | 3-$CF_3$-benzyl |
| 1375 | 4-F, 3-$CH_3$ | 1399 | isopropylthio |
| 1376 | 3-Cl, 4-Cl | 1400 | cyclopentoxy |
| 1377 | 3,4-$(CH_2)_4$ | 1401 | 3-Cl-5-pyridinyloxy |
| 1378 | 3-$HCF_2CF_2O$ | 1402 | 3-$CF_3S$-benzyloxy |
| 1379 | 3-$CHF_2O$ | 1403 | 3-$CH_3$, 4-$CH_3$-benzyloxy |
| 1380 | 3-$(CH_3)_2N$ | 1404 | 2-F, 3-$CF_3$-benzyloxy |
| 1381 | 3-cyclopropyl | 1405 | 3-F, 5-$CF_3$-benzyloxy |
| 1382 | 3-(2-furyl) | 1406 | 4-$(CH_3)_2CH$-benzyloxy |
| 1383 | 3-$CF_3CF_2$ | 1407 | 1-phenylethoxy |
| 1384 | 4-$NH_2$ | 1408 | 4-F, 3-$CH_3$-benzoyl |
| 1385 | 3-$CH_3$, 4-$CH_3$, 5-$CH_3$ | 1409 | 3-$CF_3$-phenyl |
| 1386 | 4-$CH_3CH_2CH_2O$ | 1410 | 4-$CH_3O$-phenylamino |
| 1387 | 3-$CF_3$ | 1411 | cyclopropoxy |
| 1388 | 2-$NO_2$ | 1412 | 4-$NO_2$-phenylthio |

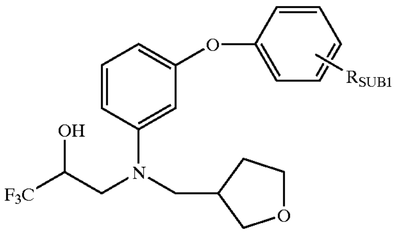

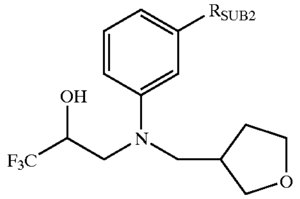

| Ex. No. | $R_{SUB1}$ | Ex. No. | $R_{SUB2}$ |
|---|---|---|---|
| 1413 | 3-isopropyl | 1437 | 3-$CF_3O$-benzyloxy |
| 1414 | 2-Cl, 3-Cl | 1438 | 3-$CF_3$-benzyloxy |
| 1415 | 3-$CF_3O$ | 1439 | 3-F, 5-F-benzyloxy |
| 1416 | 4-F | 1440 | cyclohexylmethyleneoxy |
| 1417 | 4-$CH_3$ | 1441 | benzyloxy |
| 1418 | 2-F, 5-Br | 1442 | 3-$CF_3$, 5-$CF_3$-benzyloxy |
| 1419 | 4-Cl, 3-$CH_3CH_2$ | 1443 | 4-$CF_3O$-benzyloxy |
| 1420 | 3-$CH_3CH_2$ | 1444 | 4-$CH_3CH_2$-benzyloxy |
| 1421 | 3-$CH_3$, 5-$CH_3$ | 1445 | isopropoxy |
| 1422 | 3-$(CH_3)_3C$ | 1446 | 3-$CF_3$-benzyl |
| 1423 | 4-F, 3-$CH_3$ | 1447 | isopropylthio |
| 1424 | 3-Cl, 4-Cl | 1448 | cyclopentoxy |
| 1425 | 3,4-$(CH_2)_4$ | 1449 | 3-Cl-5-pyridinyloxy |
| 1426 | 3-$HCF_2CF_2O$ | 1450 | 3-$CF_3S$-benzyloxy |
| 1427 | 3-$CHF_2O$ | 1451 | 3-$CH_3$, 4-$CH_3$-benzyloxy |
| 1428 | 3-$(CH_3)_2N$ | 1452 | 2-F, 3-$CF_3$-benzyloxy |
| 1429 | 3-cyclopropyl | 1453 | 3-F, 5-$CF_3$-benzyloxy |
| 1430 | 3-(2-furyl) | 1454 | 4-$(CH_3)_2CH$-benzyloxy |
| 1431 | 3-$CF_3CF_2$ | 1455 | 1-phenylethoxy |
| 1432 | 4-$NH_2$ | 1456 | 4-F, 3-$CH_3$-benzoyl |
| 1433 | 3-$CH_3$, 4-$CH_3$, 5-$CH_3$ | 1457 | 3-$CF_3$-phenyl |
| 1434 | 4-$CH_3CH_2CH_2O$ | 1458 | 4-$CH_3O$-phenylamino |
| 1435 | 3-$CF_3$ | 1459 | cyclopropoxy |
| 1436 | 2-$NO_2$ | 1460 | 4-$NO_2$-phenylthio |

EXAMPLE TABLE 7

3-[(N-aryl)[[haloalkyl]methyl]amino]-halo-2-propanols.

| Ex. No. | $R_{SUB1}$ | Ex. No. | $R_{SUB2}$ |
|---|---|---|---|

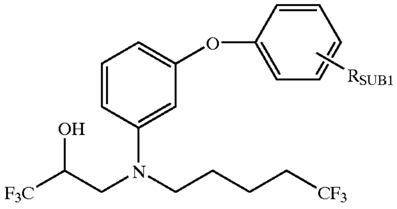

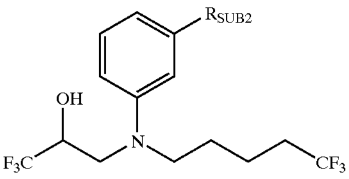

| Ex. No. | $R_{SUB1}$ | Ex. No. | $R_{SUB2}$ |
|---|---|---|---|
| 1461 | 3-isopropyl | 1485 | 3-$CF_3O$-benzyloxy |
| 1462 | 2-Cl, 3-Cl | 1486 | 3-$CF_3$-benzyloxy |

EXAMPLE TABLE 7-continued

3-[(N-aryl)[[haloalkyl]methyl]amino]-halo-2-propanols.

| Ex. No. | $R_{SUB1}$ | Ex. No. | $R_{SUB2}$ |
|---|---|---|---|
| 1463 | 3-$CF_3O$ | 1487 | 3-F, 5-F-benzyloxy |
| 1464 | 4-F | 1488 | cyclohexylmethyleneoxy |
| 1465 | 4-$CH_3$ | 1489 | benzyloxy |
| 1466 | 2-F, 5-Br | 1490 | 3-$CF_3$, 5-$CF_3$-benzyloxy |
| 1467 | 4-Cl, 3-$CH_3CH_2$ | 1491 | 4-$CF_3O$-benzyloxy |
| 1468 | 3-$CH_3CH_2$ | 1492 | 4-$CH_3CH_2$-benzyloxy |
| 1469 | 3-$CH_3$, 5-$CH_3$ | 1493 | isopropoxy |
| 1470 | 3-$(CH_3)_3C$ | 1494 | 3-$CF_3$-benzyl |
| 1471 | 4-F, 3-$CH_3$ | 1495 | isopropylthio |
| 1472 | 3-Cl, 4-Cl | 1496 | cyclopentoxy |
| 1473 | 3,4-$(CH_2)_4$ | 1497 | 3-Cl-5-pyridinyloxy |
| 1474 | 3-$HCF_2CF_2O$ | 1498 | 3-$CF_3S$-benzyloxy |
| 1475 | 3-$CHF_2O$ | 1499 | 3-$CH_3$, 4-$CH_3$-benzyloxy |
| 1476 | 3-$(CH_3)_2N$ | 1500 | 2-F, 3-$CF_3$-benzyloxy |
| 1477 | 3-cyclopropyl | 1501 | 3-F, 5-$CF_3$-benzyloxy |
| 1478 | 3-(2-furyl) | 1502 | 4-$(CH_3)_2CH$-benzyloxy |
| 1479 | 3-$CF_3CF_2$ | 1503 | 1-phenylethoxy |
| 1480 | 4-$NH_2$ | 1504 | 4-F, 3-$CH_3$-benzoyl |
| 1481 | 3-$CH_3$, 4-$CH_3$, 5-$CH_3$ | 1505 | 3-$CF_3$-phenyl |
| 1482 | 4-$CH_3CH_2CH_2O$ | 1506 | 4-$CH_3O$-phenylamino |
| 1483 | 3-$CF_3$ | 1507 | cyclopropoxy |
| 1484 | 2-$NO_2$ | 1508 | 4-$NO_2$-phenylthio |
| 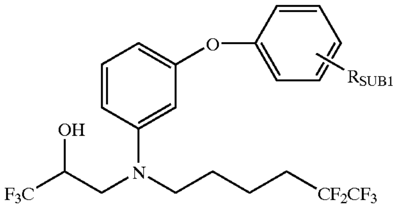 | | 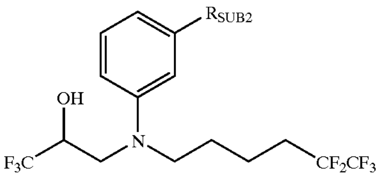 | |
| 1509 | 3-isopropyl | 1533 | 3-$CF_3O$-benzyloxy |
| 1510 | 2-Cl, 3-Cl | 1534 | 3-$CF_3$-benzyloxy |
| 1511 | 3-$CF_3O$ | 1535 | 3-F, 5-F-benzyloxy |
| 1512 | 4-F | 1536 | cyclohexylmethyleneoxy |
| 1513 | 4-$CH_3$ | 1537 | benzyloxy |
| 1514 | 2-F, 5-Br | 1538 | 3-$CF_3$, 5-$CF_3$-benzyloxy |
| 1515 | 4-Cl, 3-$CH_3CH_2$ | 1539 | 4-$CF_3O$-benzyloxy |
| 1516 | 3-$CH_3CH_2$ | 1540 | 4-$CH_3CH_2$-benzyloxy |
| 1517 | 3-$CH_3$, 5-$CH_3$ | 1541 | isopropoxy |
| 1518 | 3-$(CH_3)_3C$ | 1542 | 3-$CF_3$-benzyl |
| 1519 | 4-F, 3-$CH_3$ | 1543 | isopropylthio |
| 1520 | 3-Cl, 4-Cl | 1544 | cyclopentoxy |
| 1521 | 3,4-$(CH_2)_4$ | 1545 | 3-Cl-5-pyridinyloxy |
| 1522 | 3-$HCF_2CF_2O$ | 1546 | 3-$CF_3S$-benzyloxy |
| 1523 | 3-$CHF_2O$ | 1547 | 3-$CH_3$, 4-$CH_3$-benzyloxy |
| 1524 | 3-$(CH_3)_2N$ | 1548 | 2-F, 3-$CF_3$-benzyloxy |
| 1525 | 3-cyclopropyl | 1549 | 3-F, 5-$CF_3$-benzyloxy |
| 1526 | 3-(2-furyl) | 1550 | 4-$(CH_3)_2CH$-benzyloxy |
| 1527 | 3-$CF_3CF_2$ | 1551 | 1-phenylethoxy |
| 1528 | 4-$NH_2$ | 1552 | 4-F, 3-$CH_3$-benzoyl |
| 1529 | 3-$CH_3$, 4-$CH_3$, 5-$CH_3$ | 1553 | 3-$CF_3$-phenyl |
| 1530 | 4-$CH_3CH_2CH_2O$ | 1554 | 4-$CH_3O$-phenylamino |
| 1531 | 3-$CF_3$ | 1555 | cyclopropoxy |
| 1532 | 2-$NO_2$ | 1556 | 4-$NO_2$-phenylthio |
| 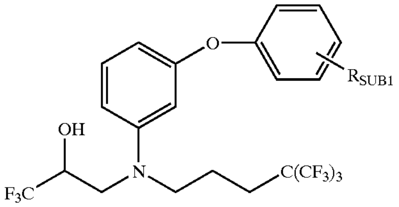 | | 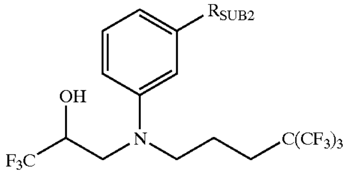 | |
| 1557 | 3-isopropyl | 1581 | 3-$CF_3O$-benzyloxy |
| 1558 | 2-Cl, 3-Cl | 1582 | 3-$CF_3$-benzyloxy |
| 1559 | 3-$CF_3O$ | 1583 | 3-F, 5-F-benzyloxy |
| 1560 | 4-F | 1584 | cyclohexylmethyleneoxy |
| 1561 | 4-$CH_3$ | 1585 | benzyloxy |

EXAMPLE TABLE 7-continued

3-[(N-aryl)][[haloalkyl]methyl]amino]-halo-2-propanols.

| Ex. No. | $R_{SUB1}$ | Ex. No. | $R_{SUB2}$ |
|---|---|---|---|
| 1562 | 2-F, 5-Br | 1586 | 3-$CF_3$, 5-$CF_3$-benzyloxy |
| 1563 | 4-Cl, 3-$CH_3CH_2$ | 1587 | 4-$CF_3O$-benzyloxy |
| 1564 | 3-$CH_3CH_2$ | 1588 | 4-$CH_3CH_2$-benzyloxy |
| 1565 | 3-$CH_3$, 5-$CH_3$ | 1589 | isopropoxy |
| 1566 | 3-$(CH_3)_3C$ | 1590 | 3-$CF_3$-benzyl |
| 1567 | 4-F, 3-$CH_3$ | 1591 | isopropylthio |
| 1568 | 3-Cl, 4-Cl | 1592 | cyclopentoxy |
| 1569 | 3,4-$(CH_2)_4$ | 1593 | 3-Cl-5-pyridinyloxy |
| 1570 | 3-$HCF_2CF_2O$ | 1594 | 3-$CF_3S$-benzyloxy |
| 1571 | 3-$CHF_2O$ | 1595 | 3-$CH_3$, 4-$CH_3$-benzyloxy |
| 1572 | 3-$(CH_3)_2N$ | 1596 | 2-F, 3-$CF_3$-benzyloxy |
| 1573 | 3-cyclopropyl | 1597 | 3-F, 5-$CF_3$-benzyloxy |
| 1574 | 3-(2-furyl) | 1598 | 4-$(CH_3)_2CH$-benzyloxy |
| 1575 | 3-$CF_3CF_2$ | 1599 | 1-phenylethoxy |
| 1576 | 4-$NH_2$ | 1600 | 4-F, 3-$CH_3$-benzoyl |
| 1577 | 3-$CH_3$, 4-$CH_3$, 5-$CH_3$ | 1601 | 3-$CF_3$-phenyl |
| 1578 | 4-$CH_3CH_2CH_2O$ | 1602 | 4-$CH_3O$-phenylamino |
| 1579 | 3-$CF_3$ | 1603 | cyclopropoxy |
| 1580 | 2-$NO_2$ | 1604 | 4-$NO_2$-phenylthio |

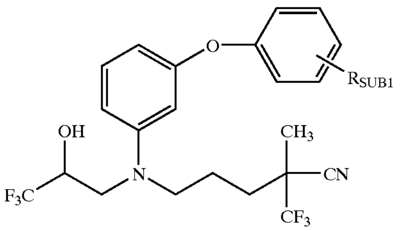

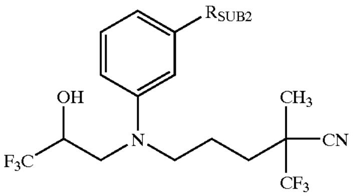

| Ex. No. | $R_{SUB1}$ | Ex. No. | $R_{SUB2}$ |
|---|---|---|---|
| 1605 | 3-isopropyl | 1629 | 3-$CF_3O$-benzyloxy |
| 1606 | 2-Cl, 3-Cl | 1630 | 3-$CF_3$-benzyloxy |
| 1607 | 3-$CF_3O$ | 1631 | 3-F, 5-F-benzyloxy |
| 1608 | 4-F | 1632 | cyclohexylmethyleneoxy |
| 1609 | 4-$CH_3$ | 1633 | benzyloxy |
| 1610 | 2-F, 5-Br | 1634 | 3-$CF_3$, 5-$CF_3$-benzyloxy |
| 1611 | 4-Cl, 3-$CH_3CH_2$ | 1635 | 4-$CF_3O$-benzyloxy |
| 1612 | 3-$CH_3CH_2$ | 1636 | 4-$CH_3CH_2$-benzyloxy |
| 1613 | 3-$CH_3$, 5-$CH_3$ | 1637 | isopropoxy |
| 1614 | 3-$(CH_3)_3C$ | 1638 | 3-$CF_3$-benzyl |
| 1615 | 4-F, 3-$CH_3$ | 1639 | isopropylthio |
| 1616 | 3-Cl, 4-Cl | 1640 | cyclopentoxy |
| 1617 | 3,4-$(CH_2)_4$ | 1641 | 3-Cl-5-pyridinyloxy |
| 1618 | 3-$HCF_2CF_2O$ | 1642 | 3-$CF_3S$-benzyloxy |
| 1619 | 3-$CHF_2O$ | 1643 | 3-$CH_3$, 4-$CH_3$-benzyloxy |
| 1620 | 3-$(CH_3)_2N$ | 1644 | 2-F, 3-$CF_3$-benzyloxy |
| 1621 | 3-cyclopropyl | 1645 | 3-F, 5-$CF_3$-benzyloxy |
| 1622 | 3-(2-furyl) | 1646 | 4-$(CH_3)_2CH$-benzyloxy |
| 1623 | 3-$CF_3CF_2$ | 1647 | 1-phenylethoxy |
| 1624 | 4-$NH_2$ | 1648 | 4-F, 3-$CH_3$-benzoyl |
| 1625 | 3-$CH_3$, 4-$CH_3$, 5-$CH_3$ | 1649 | 3-$CF_3$-phenyl |
| 1626 | 4-$CH_3CH_2CH_2O$ | 1650 | 4-$CH_3O$-phenylamino |
| 1627 | 3-$CF_3$ | 1651 | cyclopropoxy |
| 1628 | 2-$NO_2$ | 1652 | 4-$NO_2$-phenylthio |

Bioassays

CETP Activity In Vitro

Assay of CETP Inhibition Using Purified Components (Reconstituted Buffer Assay)

The ability of compounds to inhibit CETP activity was assessed using an in vitro assay that measured the rate of transfer of radiolabeled cholesteryl ester ([$^3$H]CE) from HDL donor particles to LDL acceptor particles. Details of the assay are provided by Glenn, K. C. et al. (Glenn and Melton, "Quantification of Cholesteryl Ester Transfer Protein (CETP): A) CETP Activity and B) Immunochemical Assay of CETP Protein," *Meth. Enzymol.,* 263, 339–351 (1996)). Human recombinant CETP can be obtained from the serum-free conditioned medium of CHO cells transfected with a cDNA for CETP and purified as described by Wang, S. et al. (*J. Biol. Chem.* 267, 17487–17490 (1992)). To measure CETP activity, [$^3$H]CE-labeled-HDL, LDL, CETP and assay buffer (50 mM tris(hydroxymethyl) aminomethane, pH 7.4; 150 mM sodium chloride; 2 mM ethylenediamine-tetraacetic acid (EDTA); 1% bovine serum albumin) were incubated in a final volume of 200 μL, for 2 hours at 37° C. in 96 well plates. Inhibitors were included in the assay by diluting from a 10 mM DMSO stock solution into 16% (v/v) aqueous DMSO so that the final concentration of inhibitor was 800 μM. The inhibitors were then diluted 1:1 with CETP in assay buffer, and then 25 μL of that solution was mixed with 175 μL of lipoprotein pool for assay. Following incubation, LDL was differentially precipitated by the addition of 50 μL of 1% (w/v) dextran sulfate/0.5 M magnesium chloride, mixed by vortex, and incubated at room temperature for 10 minutes. A potion of the solution (200 $\mu$L) was transferred to a filter plate (Millipore). After filtration, the radioactivity present in the precipitated LDL was measured by liquid scintillation counting. Correction for non-specific transfer or precipitation was made by including samples that do not contain CETP. The rate of [$^3$H]CE transfer using this assay was linear with respect to time and CETP concentration, up to 25–30% of [$^3$H]CE transferred.

The potency of test compounds was determined by performing the above described assay in the presence of varying concentrations of the test compounds and determining the concentration required for 50% inhibition of transfer of [3H]CE from HDL to LDL. This value was defined as the $IC_{50}$. The $IC_{50}$ values determined from this assay are accurate when the $IC_{50}$ is greater than 10 nM. In the case where compounds have greater inhibitory potency, accurate measurements of $IC_{50}$ may be determined using longer incubation times (up to 18 hours) and lower final concentrations of CETP (<50 nM).

Examples of $IC_{50}$ values determined by these methods are summarized in Table 3.

TABLE 3

Inhibition of CETP Activity by Examples in Reconstituted Buffer Assay.

| Ex. No. | $IC_{50}$ ($\mu$M) |
|---|---|
| 18 | 11 |
| 1 | 15 |
| 16 | 15 |
| 9 | 18 |
| 4 | 20 |
| 11 | 45 |
| 8 | 45 |
| 10 | 50 |
| 14 | 55 |
| 12 | 60 |
| 17 | 60 |
| 13 | 80 |
| 7 | 100 |
| 2 | 100 |
| 6 | >100.0 |
| 5 | >100.0 |
| 15 | >100.0 |
| 3 | not tested |

What we claim is:

1. A compound of Formula G:

(G)

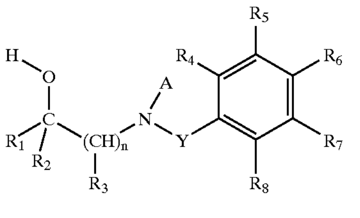

or a pharmaceutically acceptable salt thereof, wherein;

n is 1 or 2;

$R_1$ is haloalkyl or haloalkoxymethyl, with the proviso that said haloalkyl has two or more halo substituents;

$R_2$ is selected from the group consisting of hydrogen, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrogen, aryl, alkyl, alkenyl, haloalkyl, and haloalkoxyalkyl;

Y is oxy or a C1–C2 alkylene;

A is a C3–C10 cycloalkyl ring or a C5–C10 cycloalkenyl ring, wherein said cycloalkyl ring or said cycloalkenyl ring is optionally substituted with any one of $R_{10}$, $R_{11}$, $R_{12}$, $R_{31}$ and $R_{32}$, at each ring carbon other than the ring carbon attached to the backbone nitrogen atom of Formula G and other than the two ring carbons adjacent to said ring carbon attached to the backbone nitrogen;

$R_4$ is hydrogen or halo, unless $R_4$ is bonded together with $R_5$;

$R_5$ is hydrogen or $R_{10}$, unless $R_5$ is bonded together with $R_4$ or $R_6$;

$R_6$ is hydrogen or $R_{11}$, unless $R_6$ is bonded together with $R_5$ or $R_7$;

$R_7$ is hydrogen or $R_{12}$, unless $R_7$ is bonded together with $R_6$ or $R_8$;

$R_8$ is hydrogen or halo, unless $R_8$ is bonded together with $R_7$;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, heterocyclyl, alkylamino, alkenyloxy, aralkylaryl, heteroaryloxyalkyl, heteroarylthio, and heteroarylsulfonyl;

$R_4$ and $R_5$ are optionally taken together or $R_5$ and $R_6$ are optionally taken together or $R_6$ and $R_7$ are optionally taken together or $R_7$ and $R_8$ are optionally taken together to form a ring selected from the group consisting of a cycloalkenyl ring having 5 through 8 members, a partially saturated heterocyclyl ring having 5 through 8 members, a heteroaryl ring having 5 or 6 members, and an aryl ring;

with the proviso that at least one of $R_4$, $R_5$, $R_6$, $R_7$, or $R_8$ is not hydrogen.

2. A compound of claim 1, or a pharmaceutically acceptable salt thereof, wherein;

n is 1;

$R_1$ is haloalkyl or haloalkoxymethyl, with the proviso that said haloalkyl has two or more halo substituents;

$R_2$ is selected from the group consisting of hydrogen, aryl, alkyl, alkenyl, haloalkyl, haloalkoxy, and haloalkoxyalkyl;

$R_3$ is selected from the group consisting of hydrogen, aryl, alkyl, alkenyl, haloalkyl, and haloalkoxyalkyl;

Y is oxy or methylene;

A is a C3–C10 cycloalkyl ring or a C5–C8 cycloalkenyl ring, wherein said cycloalkyl ring or said cycloalkenyl ring is optionally substituted with any one of $R_{10}$, $R_{11}$, $R_{12}$, $R_{31}$, and $R_{32}$ at each ring carbon other than the ring carbon attached to the backbone nitrogen atom of Formula G and other than the two ring carbons adjacent to said ring carbon attached to the backbone nitrogen;

$R_4$ is hydrogen or halo;

$R_5$ is hydrogen or $R_{10}$, unless $R_5$ is bonded together with $R_6$ to form a partially saturated heterocyclyl ring having 5 through 8 members;

$R_6$ is hydrogen or $R_{11}$, unless $R_6$ is bonded together with $R_5$ to form a partially saturated heterocyclyl ring having 5 through 8 members;

$R_7$ is hydrogen or $R_{12}$;

$R_8$ is hydrogen or halo;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heterocyclyl, alkylamino, and alkenyloxy;

with the proviso that at least one of $R_4$, $R_5$, $R_6$, $R_7$, or $R_8$ is not hydrogen.

3. A compound of claim 2 of Formula GN:

(GN)

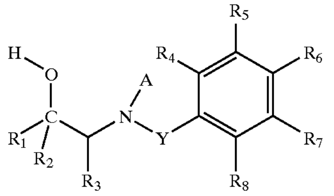

or a pharmaceutically acceptable salt thereof, wherein;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrogen, methyl, ethyl, propyl, butyl, vinyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrogen, phenyl, 4-trifluoromethylphenyl, methyl, ethyl, vinyl, trifluoromethyl, trifluoromethoxymethyl, difluoromethyl, chlorodifluoromethyl, and pentafluoroethyl;

Y is methylene or oxy;

A is selected from the group consisting of

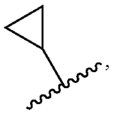 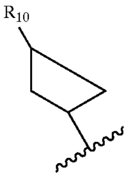 , 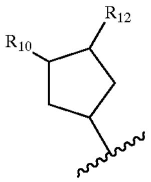 ,

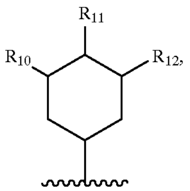 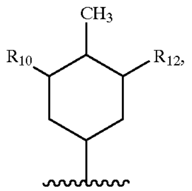

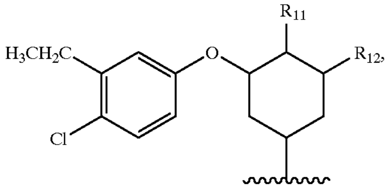

-continued

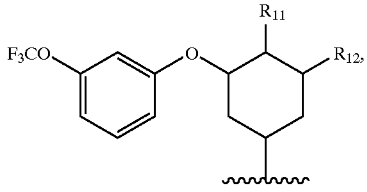

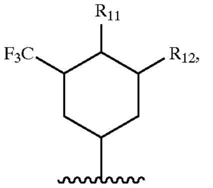 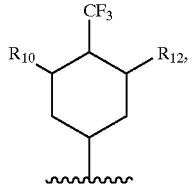

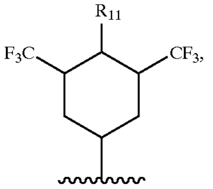 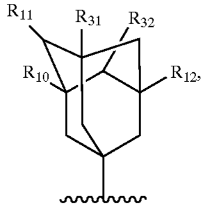

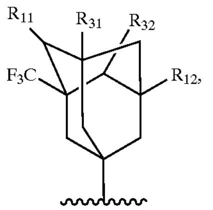 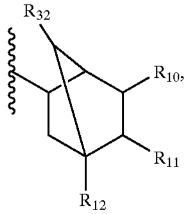

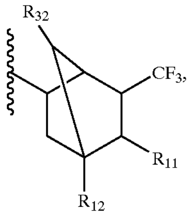 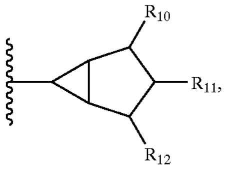

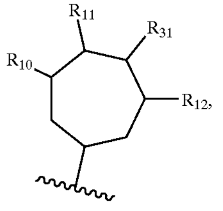 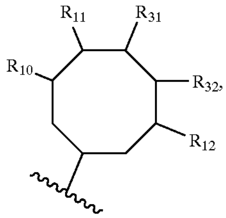

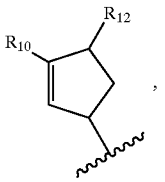 , 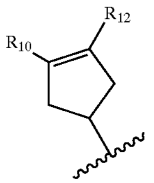 , 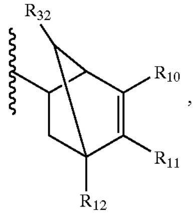 ,

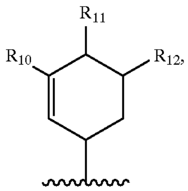 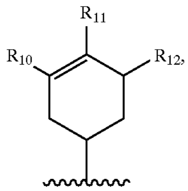

-continued

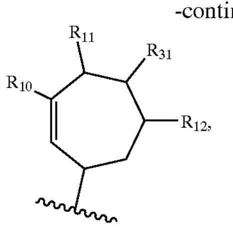
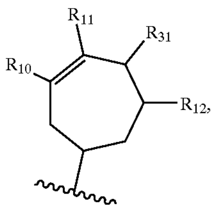
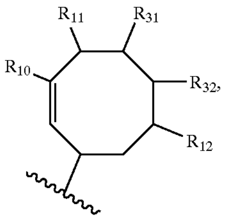
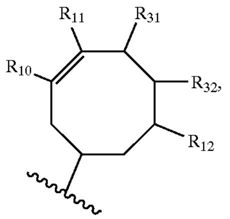
and
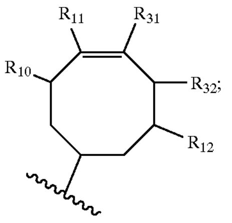

$R_4$ and $R_8$ are independently hydrogen or fluoro;

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethyl, and trifluoromethoxy, unless $R_6$ is bonded together with $R_5$ to form a partially saturated heterocyclyl ring having 5 through 8 members;

$R_7$ is selected from the group consisting of hydrogen, fluoro, and trifluoromethyl;

$R_{10}$ and $R_{12}$ are selected from the group consisting of hydrogen, 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenyloxy, 2,4-difluorobenyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isoamyl, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethoxy, pentafluoroethyl, 3-pentafluoroethylphenoxy, pentafluoroethylthio, 2,2,3,3,3-pentafluoropropyl, 1,1,3,3,3-pentafluoropropyl, 1,1,2,2,3-pentafluoropropyl, phenoxy, phenyl, phenylamino, 1-phenylethoxy, phenylsulfonyl, 4-propanoylphenoxy, propoxy, 4-propylphenoxy, 4-propoxyphenoxy, 2-pyridyl, thiophen-3-yl, sec-butyl, 4-sec-butylphenoxy, sec-butoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_{11}$, $R_{31}$, and $R_{32}$ are independently selected from the group consisting of hydrogen, chloro, fluoro, methyl, pentafluoroethyl, 1,1,2,2-tetrafluoroethoxy, trifluoromethyl, and trifluoromethoxy.

4. Compound of claim 3, or a pharmaceutically acceptable salt thereof, wherein;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrogen, methyl, ethyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrogen, phenyl, 4-trifluoromethylphenyl, methyl, trifluoromethyl, difluoromethyl, and chlorodifluoromethyl;

Y is methylene;

A is selected from the group consisting of

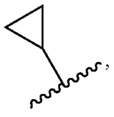
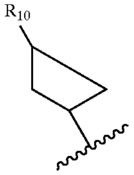
,
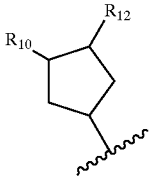
,
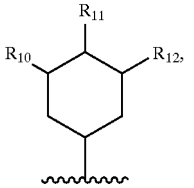
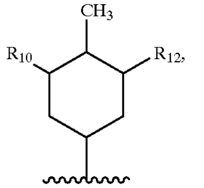
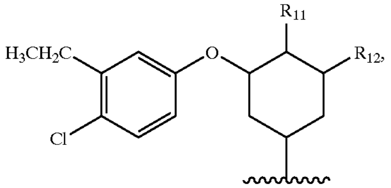
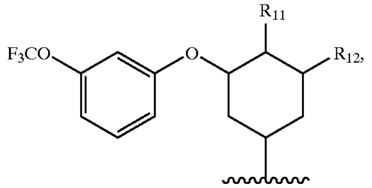
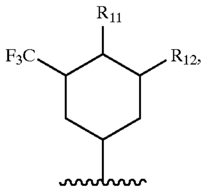
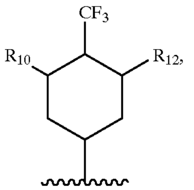
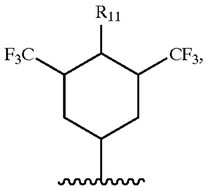
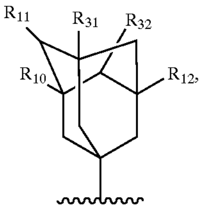

-continued

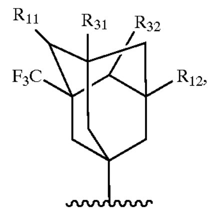
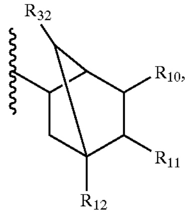
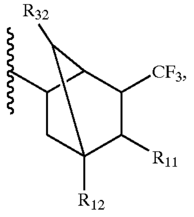
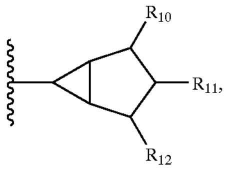
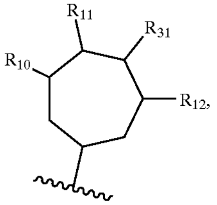
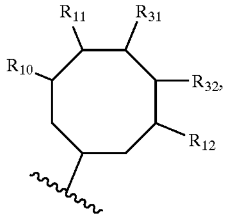
and
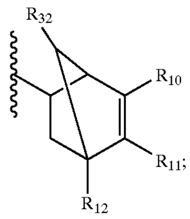

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethoxy, and trifluoromethyl, unless $R_6$ is bonded together with $R_5$ to form a partially saturated heterocyclyl ring having 5 through 8 members;

$R_7$ is selected from the group consisting of hydrogen, fluoro, and trifluoromethyl;

$R_{10}$ and $R_{12}$ are selected from the group consisting of hydrogen, benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, cyclopropyl,2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5- difluorophenoxy, 3,5-dimethoxyphenoxy,3-dimethylaminophenoxy 3,4-dimethylbenzyloxy, 3,5-dimethylbenzyloxy, 3,5-dimethylphenoxy, 3,4-dimethylphenoxy, 1,3-dioxolan-2-yl, ethoxy, 3-ethylbenzyloxy, 3-ethylphenoxy, 4-ethylamino-phenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethyl-benzyloxy, 2-fluorophenoxy, 4-fluorophenoxy, 2-fluoro-3-trifluoromethylphenoxy, 2-fluorobenzyloxy, 4-fluorophenylanilno, 2-fluoro-4-trifluoromethyl-phenoxy, 2-furyl, 3-furyl, heptafluoropropyl, 1,1,1,3,3,3-hexafluoro-2-propyl, 2-hydroxy-3,3,3-trifluoropropoxy isoamyl, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethoxy, pentafluoroethyl, pentafluoroethylthio, 3-pentafluoroethylphenoxy, 2,2,3,3,3-pentafluoro-propyl, 1,1,3,3,3-pentafluoropropyl,1,1,2,2,3-pentafluoropropyl, phenoxy, phenyl, phenylamino, 1-phenylethoxy, 4-propylphenoxy, propoxy, 4-propoxyphenoxy, 2-pyridyl, thiophen-3-yl, sec-butoxy, tert -butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyl-oxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxy-benzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoro-ethoxy)phenoxy, 3-trifluoromethylthiophenoxy, 3-trifluoromethylthiobenzyloxy, and trifluorometh-ylthio;

$R_{11}$, $R_{31}$, and $R_{32}$ are independently selected from the group consisting of hydrogen, chloro, fluoro, methyl, pentafluoroethyl, 1,1,2,2-tetrafluoroethoxy, and trifluoromethyl.

5. A compound of claim 4, or a pharmaceutically acceptable salt thereof, wherein;

$R_1$ is selected from the group consisting of trifluoromethyl, chlorodifluoromethyl, and pentafluoroethyl;

$R_2$ is hydrogen, pentafluoroethyl, and trifluoromethyl;

$R_3$ is selected from the group consisting of hydrogen, methyl, trifluoromethyl, and difluoromethyl;

A is selected from the group consisting of

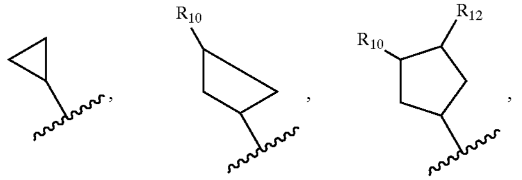

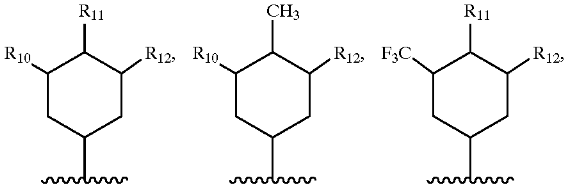

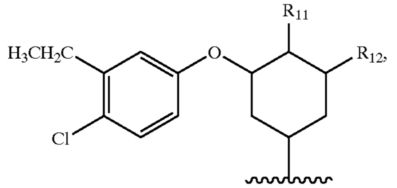

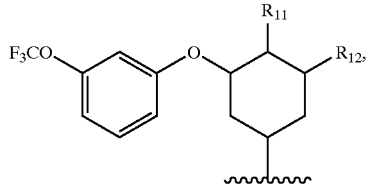

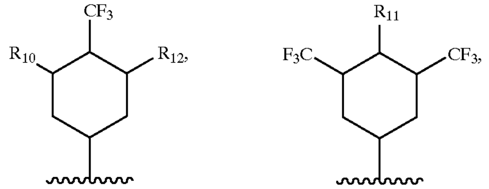

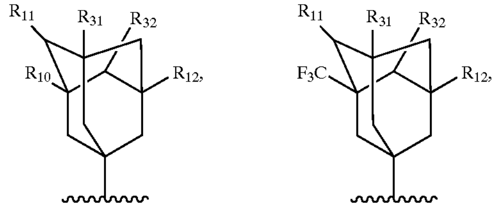

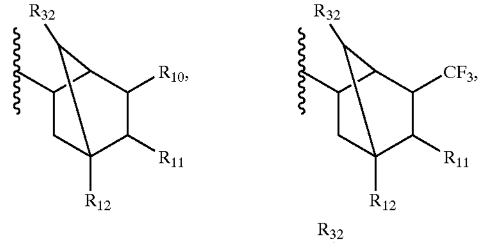

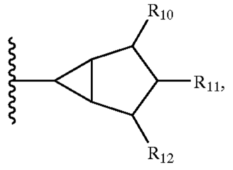

and

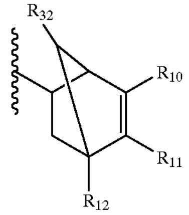

;

$R_4$ and $R_8$ are independently hydrogen or fluoro;

$R_5$ is $R_{10}$ is or bonded together with to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethoxy, and trifluoromethyl, unless $R_6$ is bonded together with $R_5$ to form a partially saturated heterocyclyl ring having 5 through 8 members;

$R_7$ is hydrogen or fluoro;

$R_{10}$ and $R_{12}$ are selected from the group consisting of hydrogen, 5-bromo-2-fluorophenoxy, 4-chloro-3-ethylphenoxy, cyclopentoxy, cyclopentyl, cyclopropyl, cyclopropylmethoxy, 2,3-dichlorophenoxy, 3,4-dichlorophenoxy, 3-difluoromethoxyphenoxy, 3,5-dimethylphenoxy, 3,4-dimethylphenoxy, ethoxy, 3-ethylphenoxy, 3-ethyl-5-methylphenoxy, 4-fluoro-3-methylphenoxy, 4-fluorophenoxy, 2-furyl, 3-furyl, heptafluoropropyl, 1,1,1,3,3,3-hexafluoro-2-propyl, isoamyl, isobutoxy, isobutyl, isopropoxy, 3-isopropylphenoxy, 3-methylphenoxy, pentafluoroethoxy, pentafluoroethyl, 3-pentafluoroethylphenoxy, 2,2,3,3,3-pentafluoropropyl, phenoxy, phenyl, propoxy, 2-pyridyl, sec-butoxy, tert-butoxy, 3-tert-butylphenoxy, 1,1,2,2-tetrafluoroethoxy, 3-(1,1,2,2-tetrafluoroethoxy)phenoxy, tetrahydro-2-furyl, 2-(5,6,7,8-tetrahydronaphthyloxy), 2-thienyl, 2,2,2-trifluoroethoxy, 2,2,2-trifluoroethyl, trifluoromethoxy, 3-trifluoromethoxybenzyloxy, 3-trifluoromethoxyphenoxy, trifluoromethyl, 3-trifluoromethylbenzyloxy, 3-trifluoromethylphenoxy, 3,3,3-trifluoro-2-hydroxypropoxy, 1,1-bis-trifluoromethyl-1-hydroxymethyl, trifluoromethylthio, and 3-trifluoromethylthiophenoxy;

$R_{11}$, $R_{31}$, and $R_{32}$ are independently selected from the group consisting of hydrogen, chloro, fluoro, methyl, pentafluoroethyl, 1,1,2,2-tetrafluoroethoxy, and trifluoromethyl.

6. Compound of claim 5, or a pharmaceutically acceptable salt thereof, wherein;

$R_2$ is hydrogen;

$R_3$ is hydrogen;

A is selected from the group consisting of

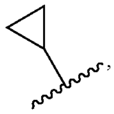,
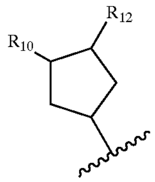,
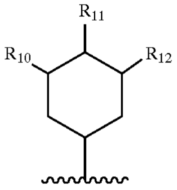,
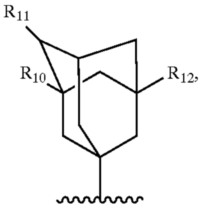 and
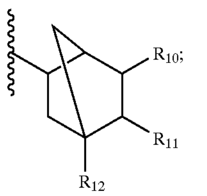

$R_5$ is selected from the group consisting of cyclopentoxy, cyclopentyl, cyclopropyl, cyclopropylmethoxy, ethoxy, 2-furyl, 3-furyl, heptafluoropropyl, 1,1,1,3,3,3-hexafluoro-2-propyl, isoamyl, isobutoxy, isobutyl, isopropoxy, pentafluoroethyl, pentafluoroethoxy, 2,2,3,3,3-pentafluoropropyl, phenoxy, phenyl, propoxy, 2-pyridyl, sec-butoxy, tert-butoxy, 1,1,2,2-tetrafluoroethoxy, tetrahydro-2-furyl, 2-thienyl, 2,2,2-trifluoroethoxy, 2,2,2-trifluoroethyl, trifluoromethoxy, trifluoromethyl, 3-trifluoromethylphenoxy, 1,1-bis-trifluoromethyl-1-hydroxymethyl, trifluoromethylthio, and 3,3,3-trifluoro-2-hydroxypropoxy, unless $R_5$ is bonded together with $R_6$ to form 1,1,2,2-tetrafluoroethylene-1,2-dioxy;

$R_6$ is selected from the group consisting of fluoro, hydrogen, trifluoromethoxy, and trifluoromethyl, unless $R_6$ is bonded together with $R_5$ to form 1,1,2,2-tetrafluoroethylene-1,2-dioxy;

$R_7$ is hydrogen;

$R_{10}$ and $R_{12}$ are independently selected from the group consisting of hydrogen, 4-chloro-3-ethylphenoxy, isopropoxy, phenoxy, 3-trifluoromethoxyphenoxy, trifluoromethyl, and 3-trifluoromethylbenzyloxy;

$R_{11}$ is selected from the group consisting of hydrogen, methyl, and trifluoromethyl.

7. Compound of claim 6, or a pharmaceutically acceptable salt thereof, wherein said compound is selected from the group consisting of:

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4methylcyclohexyl)amino]-1,1,1-trifluoro-2-propanol;

3-[[[(3-pentafluoroethyl)phenyl]methyl](4methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4methylcyclohexyl) amino]-1,1,1-trifluoro-2-propanol;

3-[[[(3-trifluoromethyl)phenyl]methyl](3-trifluoromethylcyclohexyl) amino]-1,1,1-trifluoro-2-propanol;

3-[[[(3-pentafluoroethyl)phenyl]methyl](3-trifluoromethylcyclohexyl) amino]-1,1,1-trifluoro-2-propanol;

3-[[[(3-trifluoromethoxy)phenyl]methyl](3-trifluoromethylcyclohexyl) amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4chloro-3-ethylphenoxy) cyclohexyl]amino]-1,1,1-trifluoro-2-propanol;

3-[[[(3-trifluoromethoxy)phenyl]methyl][3-(4-chloro-3-ethylphenoxy) cyclohexyl]amino]-1,1,1-trifluoro-2-propanol;

3-[[[3-(1,1,2,2-tetrafluoroethoxy)phenyl]methyl][3-(4-chloro-3-ethylphenoxy)cyclohexyl]amino]-1,1,1-trifluoro-2-propanol;

3-[[[(3-trifluoromethyl)phenyl]methyl](3phenoxycyclohexyl)amino]-1,1,1-trifluoro-2-propanol;

3-[[[(3-pentafluoroethyl)phenyl]methyl](3phenoxycyclohexyl)amino]-1,1,1-trifluoro-2-propanol;

3-[[[(3-trifluoromethoxy)phenyl]methyl](3phenoxy-cyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifluoromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)amino]-1,1,1-trifluoro-2-propanol;

3-[[[(3-trifluoromethyl)phenyl]methyl](3-cyclopentyloxycyclohexyl)amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol; and 3-[[[3-(1,1,2,2-tetrafluoroethoxy)phenyl]methyl](3-cyclopentyloxycyclohexyl)amino]-1,1,1-trifluoro-2-propanol.

8. Compound of claim 6, or a pharmaceutically acceptable salt thereof, wherein said compound is selected from the group consisting of:

3-[[[(3-trifluoromethyl)phenyl]methyl][(4methyl) cyclohexyl]amino]-1,1,1-trifluoro-2-propanol;

3-[[[(3-trifluoromethoxy)phenyl]methyl][cyclopropyl] amino]-1,1,1-trifluoro-2-propanol;

3-[[[(4-trifluoromethoxy)phenyl]methyl][cyclopropyl] amino]-1,1,1 -trifluoro-2-propanol; and 3-[[[(3-trifluoromethoxy)phenyl]methyl][cyclopentyl] amino]-1,1,1-trifluoro-2-propanol.

9. A pharmaceutical composition comprising a therapeutically effective amount of a compound or a pharmaceutically acceptable salt thereof, together with a pharmaceutically acceptable carrier, said compound being of Formula G:

(G)

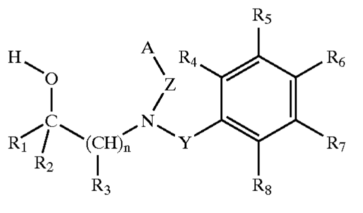

wherein;

n is 1 or 2;

$R_1$ is haloalkyl or haloalkoxymethyl, with the proviso that said haloalkyl has two or more halo substituents;

$R_2$ is selected from the group consisting of hydrogen, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrogen, aryl, alkyl, alkenyl, haloalkyl, and haloalkoxyalkyl;

Y is oxy or a C1–C2 alkylene;

A is a C3–C10 cycloalkyl ring or a C5–C10 cycloalkenyl ring, wherein said cycloalkyl ring or said cycloalkenyl ring is optionally substituted with any one of $R_{10}$, $R_{11}$, $R_{12}$, $R_{31}$, and $R_{32}$ at each ring carbon other than the ring carbon attached to the backbone nitrogen atom of Formula G and other than the two ring carbons adjacent to said ring carbon attached to the backbone nitrogen;

$R_4$ is hydrogen or halo, unless $R_4$ is bonded together with $R_5$;

$R_5$ is hydrogen or $R_{10}$, unless $R_5$ is bonded together with $R_4$ or $R_6$;

$R_6$ is hydrogen or $R_{11}$, unless $R_6$ is bonded together with $R_5$ or $R_7$;

$R_7$ is hydrogen or $R_{12}$; unless $R_7$ is bonded together with $R_6$ or $R_8$;

$R_8$ is hydrogen or halo, unless $R_8$ is bonded together with $R_7$;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, heterocyclyl, alkylamino, alkenyloxy, aralkylaryl, heteroaryloxyalkyl, heteroarylthio, and heteroarylsulfonyl;

$R_4$ and $R_5$ are optionally taken together or $R_5$ and $R_6$ are optionally taken together or $R_6$ and $R_7$ are optionally taken together or $R_7$ and $R_8$ are optionally taken together to form a ring selected from the group consisting of a cycloalkenyl ring having 5 through 8 members, a partially saturated heterocyclyl ring having 5 through 8 members, a heteroaryl ring having 5 or 6 members, and an aryl ring;

with the proviso that at least one of $R_4$, $R_5$, $R_6$, $R_7$, or $R_8$ is not hydrogen.

10. The pharmaceutical composition of claim 9, wherein said compound is of Formula G, wherein;

n is 1;

$R_1$ is haloalkyl or haloalkoxymethyl, with the proviso that said haloalkyl has two or more halo substituents;

$R_2$ is selected from the group consisting of hydrogen, aryl, alkyl, alkenyl, haloalkyl, haloalkoxy, and haloalkoxyalkyl;

$R_3$ is selected from the group consisting of hydrogen, aryl, alkyl, alkenyl, haloalkyl, and haloalkoxyalkyl;

Y is oxy or methylene;

A is a C3–C10 cycloalkyl ring or a C5–C8 cycloalkenyl ring, wherein said cycloalkyl ring or said cycloalkenyl ring is optionally substituted with any one of $R_{10}$, $R_{11}$, $R_{12}$, $R_{31}$, and $R_{32}$ at each ring carbon other than the ring carbon attached to the backbone nitrogen atom of Formula G and other than the two ring carbons adjacent to said ring carbon attached to the backbone nitrogen;

is $R_4$ hydrogen or halo;

$R_5$ is hydrogen or $R_{10}$, unless is $R_5$ bonded together with $R_6$ to form a partially saturated heterocyclyl ring having 5 through 8 members;

$R_6$ is hydrogen or $R_{11}$, unless $R_6$ is bonded together with $R_5$ to form a partially saturated heterocyclyl ring having 5 through 8 members;

$R_7$ is hydrogen or $R_{12}$;

$R_8$ is hydrogen or halo;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heterocyclyl, alkylamino, and alkenyloxy;

with the proviso that at least one of $R_4$, $R_5$, $R_6$, $R_7$, or $R_8$ is not hydrogen.

11. The pharmaceutical composition of claim 10, wherein said compound is of Formula GN:

(GN)

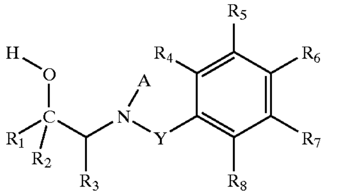

wherein;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrogen, methyl, ethyl, propyl, butyl, vinyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrogen, phenyl, 4-trifluoromethylphenyl, methyl, ethyl, vinyl, trifluoromethyl, trifluoromethoxymethyl, difluoromethyl, chlorodifluoromethyl, and pentafluoroethyl;

Y is methylene or oxy;

A is selected from the group consisting of

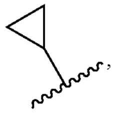
,
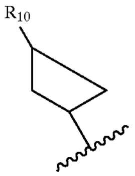
,
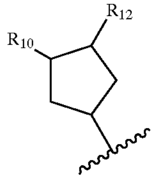
,

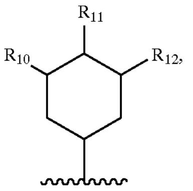

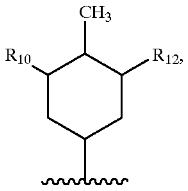

-continued

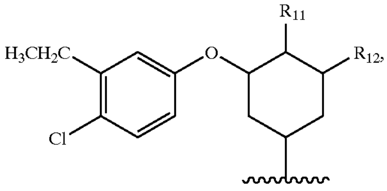

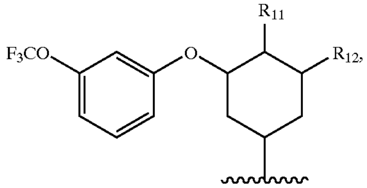

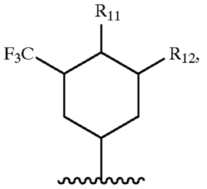

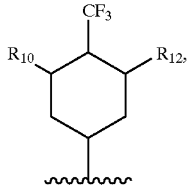

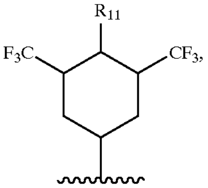

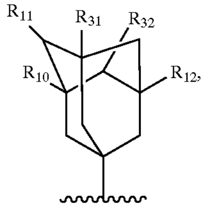

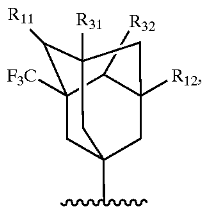

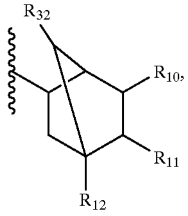

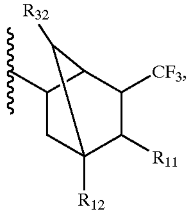

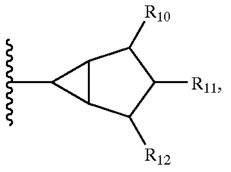

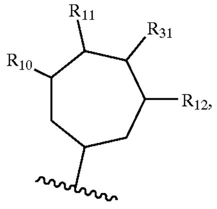

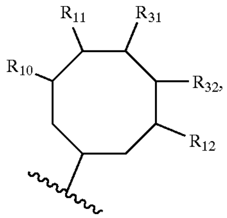

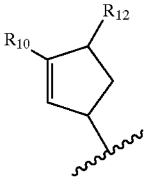
,
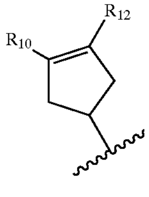
,
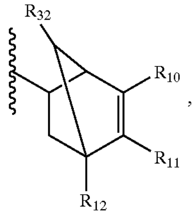
,

-continued

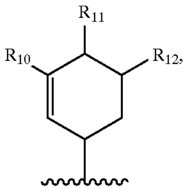
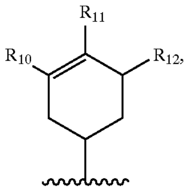
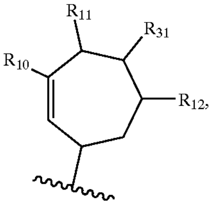
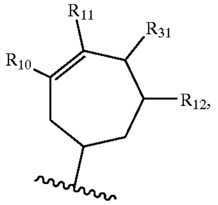
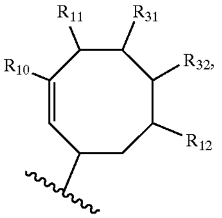
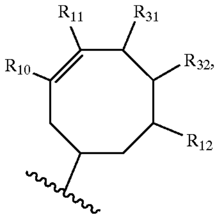
and
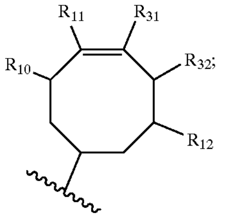

$R_4$ and $R_8$ are independently hydrogen or fluoro;

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethyl, and trifluoromethoxy, unless $R_6$ is bonded together with $R_5$ to form a partially saturated heterocyclyl ring having 5 through 8 members;

$R_7$ is selected from the group consisting of hydrogen, fluoro, and trifluoromethyl;

$R_{10}$ and $R_{12}$ are selected from the group consisting of hydrogen, 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isoamyl, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethoxy, pentafluoroethyl, 3-pentafluoroethylphenoxy, pentafluoroethylthio, 2,2,3,3,3-pentafluoropropyl, 1,1,3,3,3-pentafluoropropyl, 1,1,2,2,3-pentafluoropropyl, phenoxy, phenyl, phenylamino, 1-phenylethoxy, phenylsulfonyl, 4-propanoylphenoxy, propoxy, 4-propylphenoxy, 4-propoxyphenoxy, 2-pyridyl, thiophen-3-yl, sec-butyl, 4-sec-butylphenoxy, sec-butoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_{11}$, $R_{31}$, and $R_{32}$ are independently selected from the group consisting of hydrogen, chloro, fluoro, methyl, pentafluoroethyl, 1,1,2,2-tetrafluoroethoxy, trifluoromethyl, and trifluoromethoxy.

12. The pharmaceutical composition of claim 11, wherein said compound is of Formula GN, wherein;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrogen, methyl, ethyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrogen, phenyl, 4-trifluoromethylphenyl, methyl, trifluoromethyl, difluoromethyl, and chlorodifluoromethyl;

Y is methylene;

A is selected from the group consisting of

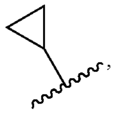,
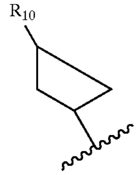,
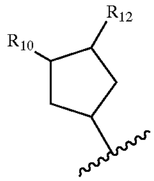,

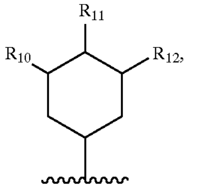
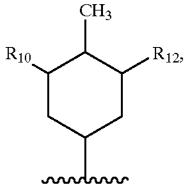

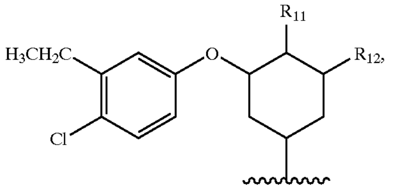

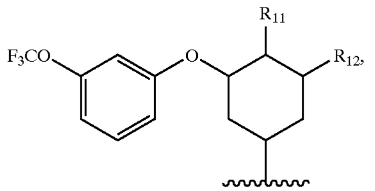

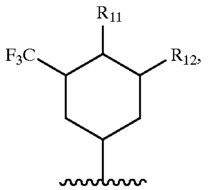
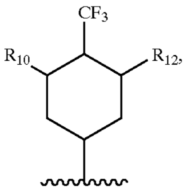

-continued

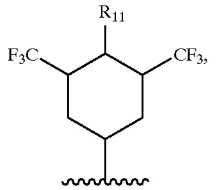
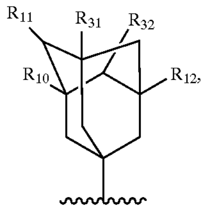

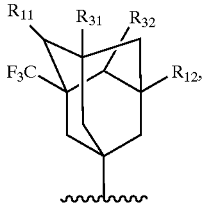
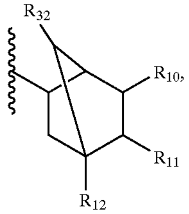

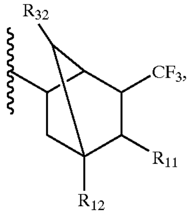
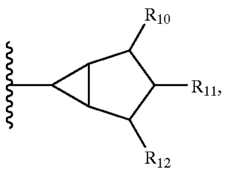

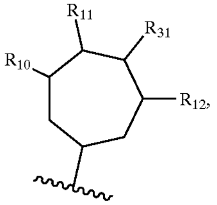
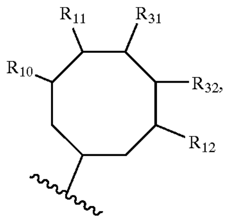 and

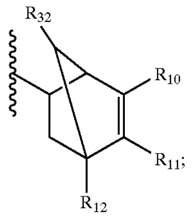

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethoxy, and trifluoromethyl, unless $R_6$ is bonded together with $R_5$ to form a partially saturated heterocyclyl ring having 5 through 8 members;

$R_7$ is selected from the group consisting of hydrogen, fluoro, and trifluoromethyl;

$R_{10}$ and $R_{12}$ are selected from the group consisting of hydrogen, benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, cyclopropyl,2,3- dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy,3-dimethylaminophenoxy 3,4-dimethylbenzyloxy, 3,5-dimethylbenzyloxy, 3,5-dimethylphenoxy, 3,4-dimethylphenoxy, 1,3-dioxolan-2-yl, ethoxy, 3-ethylbenzyloxy, 3-ethylphenoxy, 4-ethylamino-phenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoro-methylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethyl-phenoxy, 2-furyl, 3-furyl, heptafluoropropyl, 1,1,1,3,3,3-hexafluoro-2-propyl, 2-hydroxy-3,3,3-trifluoropropoxy, isoamyl, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenzyloxy, 3-methylphenoxy, 3-methyl-4-methylthiophenoxy, 4-methylphenoxy, 1 -methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethoxy, pentafluoroethyl, pentafluoroethylthio, 3-pentafluoroethylphenoxy, 2,2,3,3,3-pentafluoro-propyl, 1,1,3,3,3-pentafluoropropyl, 1,1,2,2,3-pentafluoropropyl, phenoxy, phenyl, phenylamino, 1-phenylethoxy, 4-propylphenoxy, propoxy, 4-propoxyphenoxy, 2-pyridyl, thiophen-3-yl, sec-butoxy, tert -butoxy, 3-tert-butylphenoxy, 4-tert -butylphenoxy, 1,1,2,2-tetrafluoroethoxy, tetrahydrofuran-2-yl, 2-(5,6,7,8-tetrahydronaphthyl-oxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxy-benzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoro-ethoxy)phenoxy, 3-trifluoromethylthiophenoxy, 3-trifluoromethylthiobenzyloxy, and trifluorometh-ylthio;

$R_{11}$, $R_{31}$, and $R_{32}$ are independently selected from the group consisting of hydrogen, chloro, fluoro, methyl, pentafluoroethyl, 1,1,2,2-tetrafluoroethoxy, and trifluoromethyl.

13. The pharmaceutical composition of claim 12, wherein said compound is of Formula GN, wherein;

$R_1$ is selected from the group consisting of trifluoromethyl, chlorodifluoromethyl, and pentafluoroethyl;

$R_2$ is hydrogen, pentafluoroethyl, and trifluoromethyl;

$R_3$ is selected from the group consisting of hydrogen, methyl, trifluoromethyl, and difluoromethyl;

A is selected from the group consisting of

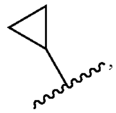,
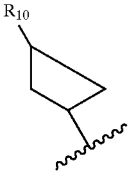,
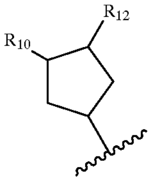,
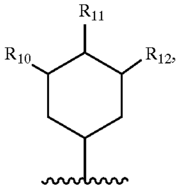
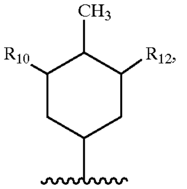
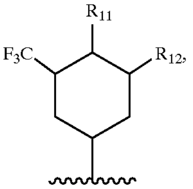
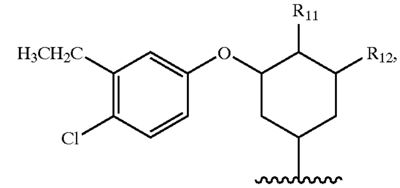
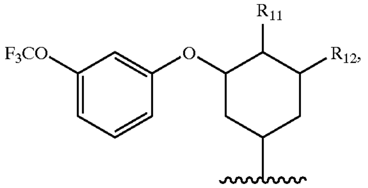
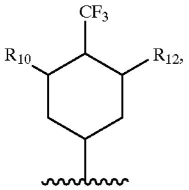
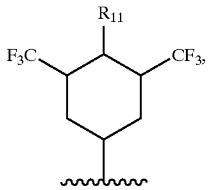
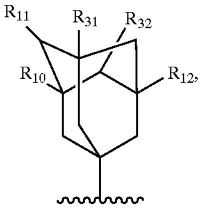
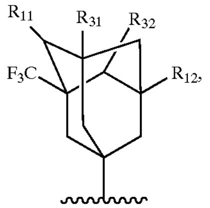
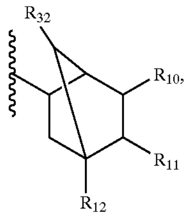
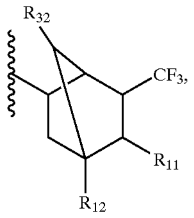
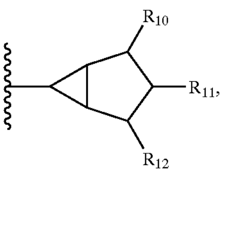
and
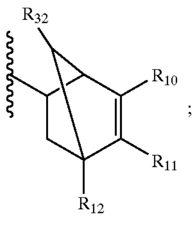
;

$R_4$ and $R_8$ are independently hydrogen or fluoro;

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethoxy, and trifluoromethyl, unless $R_6$ is bonded together with $R_5$ to form a partially saturated heterocyclyl ring having 5 through 8 members;

$R_7$ is hydrogen or fluoro;

$R_{10}$ and $R_{12}$ are selected from the group consisting of hydrogen, 5-bromo-2-fluorophenoxy, 4-chloro-3-ethylphenoxy, cyclopentoxy, cyclopentyl, cyclopropyl, cyclopropylmethoxy, 2,3-dichlorophenoxy, 3,4-dichlorophenoxy, 3-difluoromethoxyphenoxy, 3,5-dimethylphenoxy, 3,4-dimethylphenoxy, ethoxy, 3-ethylphenoxy, 3-ethyl-5-methylphenoxy, 4-fluoro-3-methylphenoxy, 4-fluorophenoxy, 2-furyl, 3-furyl, heptafluoropropyl, 1,1,1,3,3,3-hexafluoro-2-propyl, isoamyl, isobutoxy, isobutyl, isopropoxy, 3-isopropylphenoxy, 3-methylphenoxy, pentafluoroethoxy, pentafluoroethyl, 3-pentafluoroethylphenoxy, 2,2,3,3,3-pentafluoropropyl, phenoxy, phenyl, propoxy, 2-pyridyl, sec-butoxy, tert-butoxy, 3-tert-butylphenoxy, 1,1,2,2-tetrafluoroethoxy, 3-(1,1,2,2-tetrafluoroethoxy)phenoxy, tetrahydro-2-furyl, 2-(5,6,7,8-tetrahydronaphthyloxy), 2-thienyl, 2,2,2-trifluoroethoxy, 2,2,2-trifluoroethyl, trifluoromethoxy, 3-trifluoromethoxybenzyloxy, 3-trifluoromethoxyphenoxy, trifluoromethyl, 3-trifluoromethylbenzyloxy, 3-trifluoromethylphenoxy, 3,3,3-trifluoro-2-hydroxypropoxy, 1,1 -bis-trifluoromethyl-1-hydroxymethyl, trifluoromethylthio, and 3-trifluoromethylthiophenoxy;

$R_{11}$, $R_{31}$, and $R_{32}$ are independently selected from the group consisting of hydrogen, chloro, fluoro, methyl, pentafluoroethyl, 1,1,2,2-tetrafluoroethoxy, and trifluoromethyl.

14. The pharmaceutical composition of claim 13, wherein said compound is of Formula GN, wherein;

$R_2$ is hydrogen;

$R_3$ is hydrogen;

A is selected from the group consisting of

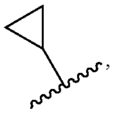 , 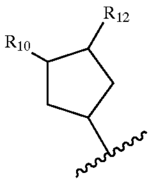 , 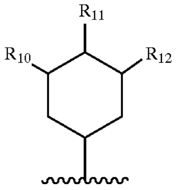 ,

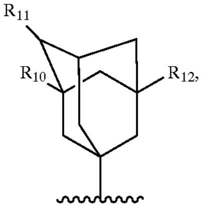 and 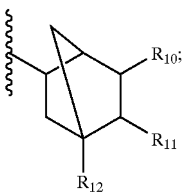

$R_5$ is selected from the group consisting of cyclopentoxy, cyclopentyl, cyclopropyl, cyclopropylmethoxy, ethoxy, 2-furyl, 3-furyl, heptafluoropropyl, 1,1,1,3,3,3-hexafluoro-2-propyl, isoamyl, isobutoxy, isobutyl, isopropoxy, pentafluoroethyl, pentafluoroethoxy, 2,2,3,3,3-pentafluoropropyl, phenoxy, phenyl, propoxy, 2-pyridyl, sec-butoxy, tert-butoxy, 1,1,2,2-tetrafluoroethoxy, tetrahydro-2-furyl,2-thienyl, 2,2,2-trifluoroethoxy, 2,2,2-trifluoroethyl, trifluoromethoxy, trifluoromethyl, 3-trifluoromethylphenoxy, 1,1-bis-trifluoromethyl-1-hydroxymethyl, trifluoromethylthio, and 3,3,3-trifluoro-2-hydroxypropoxy, unless $R_5$ is bonded together with $R_6$ to form 1,1,2,2-tetrafluoroethylene-1,2-dioxy;

$R_6$ is selected from the group consisting of fluoro, hydrogen, trifluoromethoxy, and trifluoromethyl, unless $R_6$ is bonded together with $R_5$ to form 1,1,2,2-tetrafluoroethylene-1,2-dioxy;

$R_7$ is hydrogen;

$R_{10}$ and $R_{12}$ are independently selected from the group consisting of hydrogen, 4-chloro-3-ethylphenoxy, isopropoxy, phenoxy, 3-trifluoromethoxyphenoxy, trifluoromethyl, and 3-trifluoromethylbenzyloxy;

$R_{11}$ is selected from the group consisting of hydrogen, methyl, and trifluoromethyl.

15. The pharmaceutical composition of claim 14, wherein said compound is selected from the group consisting of:

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1 -trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4-methylcyclohexyl)amino]-1,1,1-trifluoro-2-propanol;

3-[[[(3-trifluoromethyl)phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4-chloro-3-ethylphenoxy)cyclohexyl]amino]-1,1,1-trifluoro-2-propanol;

3-[[[(3-trifluoromethoxy)phenyl]methyl][-3-(4-chloro-3ethylphenoxy)cyclohexyl]amino]-1,1,1-trifluoro-2-propanol;

3-[[[3-(1,1,2,2-tetrafluoroethoxy)phenyl]methyl][3-(4-chloro-3-ethyl-phenoxy)cyclohexyl]amino]-1,1,1-trifluoro-2-propanol;

3-[[[(3-trifluoromethyl)phenyl]methyl](3phenoxycyclo-hexyl)amino]-1,1,1-trifluoro-2-propanol;

3-[[[(3-pentafluoroethyl)phenyl]methyl](3phenoxycyclohexyl)amino]-1,1,1-trifluoro-2-propanol;

3-[[[(3-trifluoromethoxy)phenyl]methyl](3phenoxycyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifluoromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)amino]-1,1,1-trifluoro-2-propanol;

3-[[[(3-trifluoromethyl)phenyl]methyl](3-cyclopentyloxycyclohexyl)amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol; and 3-[[[3-(1,1,2,2-tetrafluoroethoxy)phenyl]methyl](3cyclopentyloxycyclohexyl)amino]-1,1,1-trifluoro-2-propanol.

16. The pharmaceutical composition of claim 14, wherein said compound is selected from the group consisting of:

3-[[[(3-trifluoromethyl)phenyl]methyl][(4-methyl)cyclohexyl]amino]-1,1,1-trifluoro-2-propanol;

3-[[[(3-trifluoromethoxy)phenyl]methyl][cyclopropyl]amino]-1,1,1-trifluoro-2-propanol;

3-[[[(4-trifluoromethoxy)phenyl]methyl][cyclopropyl]amino]1,1,1-trifluoro-2-propanol; and 3-[[[(3-trifluoromethoxy)phenyl]methyl][cyclopentyl]amino]-1,1,1-trifluoro-2-propanol.

17. A method of treating or preventing a CETP-mediated disorder in a subject by administering a therapeutically effective amount of a compound or a pharmaceutically acceptable salt thereof, said compound being of Formula G:

(G)

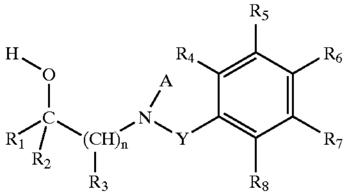

wherein;

n is 1 or 2;

$R_1$ is haloalkyl or haloalkoxymethyl, with the proviso that said haloalkyl has two or more halo substituents;

$R_2$ is selected from the group consisting of hydrogen, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrogen, aryl, alkyl, alkenyl, haloalkyl, and haloalkoxyalkyl;

Y is oxy or a C1–C2 alkylene;

A is a C3–C10 cycloalkyl ring or a C5–C10 cycloalkenyl ring, wherein said cycloalkyl ring or said cycloalkenyl ring is optionally substituted with any one of $R_{10}$, $R_{11}$, $R_{12}$, $R_{31}$, and $R_{32}$ at each ring carbon other than the ring carbon attached to the backbone nitrogen atom of Formula G and other than the two ring carbons adjacent to said ring carbon attached to the backbone nitrogen;

$R_4$ is hydrogen or halo, unless $R_4$ is bonded together with $R_5$;

$R_5$ is hydrogen or $R_{10}$, unless $R_5$ is bonded together with $R_4$ or $R_6$;

$R_6$ is hydrogen or $R_{11}$, unless $R_6$ is bonded together with $R_5$ or $R_7$;

$R_7$ is hydrogen or $R_{12}$, unless $R_7$ is bonded together with $R_6$ or $R_8$;

$R_8$ is hydrogen or halo, unless $R_8$ is bonded together with $R_7$;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, heterocyclyl, alkylamino, alkenyloxy, aralkylaryl, heteroaryloxyalkyl, heteroarylthio, and heteroarylsulfonyl;

$R_4$ and $R_5$ are optionally taken together or $R_5$ and $R_6$ are optionally taken together or $R_6$ and $R_7$ are optionally taken together or $R_7$ and $R_8$ are optionally taken together to form a ring selected from the group consisting of a cycloalkenyl ring having 5 through 8 members, a partially saturated heterocyclyl ring having 5 through 8 members, a heteroaryl ring having 5 or 6 members, and an aryl ring;

with the proviso that at least one of $R_4$, $R_5$, $R_6$, $R_7$, or $R_8$ is not hydrogen.

18. The method of claim 17, wherein said compound is of Formula G, wherein;

n is 1;

$R_1$ is haloalkyl or haloalkoxymethyl, with the proviso that said haloalkyl has two or more halo substituents;

$R_2$ is selected from the group consisting of hydrogen, aryl, alkyl, alkenyl, haloalkyl, haloalkoxy, and haloalkoxyalkyl;

$R_3$ is selected from the group consisting of hydrogen, aryl, alkyl, alkenyl, haloalkyl, and haloalkoxyalkyl;

Y is oxy or methylene;

A is a C3–C10 cycloalkyl ring or a C5–C8 cycloalkenyl ring, wherein said cycloalkyl ring or said cycloalkenyl ring is optionally substituted with any one of $R_{10}$, $R_{11}$, $R_{12}$, $R_{31}$, and $R_{32}$ at each ring carbon other than the ring carbon attached to the backbone nitrogen atom of Formula G and other than the two ring carbons adjacent to said ring carbon attached to the backbone nitrogen;

$R_4$ is hydrogen or halo;

$R_5$ is hydrogen or $R_{10}$, unless $R_5$ is bonded together with $R_6$ to form a partially saturated heterocyclyl ring having 5 through 8 members;

$R_6$ is hydrogen or $R_{11}$, unless $R_6$ is bonded together with $R_5$ to form a partially saturated heterocyclyl ring having 5 through 8 members;

$R_7$ is hydrogen or $R_{12}$;

$R_8$ is hydrogen or halo;

$R_{10}$, $R_{11}$, $R_{12}$, $R_{31}$, and $R_{32}$ are independently selected from the group group consisting of alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heterocyclyl, alkylamino, and alkenyloxy;

with the proviso that at least one of $R_4$, $R_5$, $R_6$, $R_7$, or $R_8$ is not hydrogen.

19. The method of claim 18, wherein said compound is of Formula GN:

(GN)

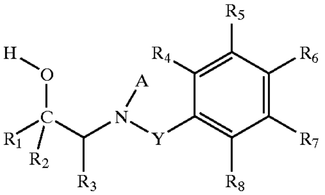

wherein;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrogen, methyl, ethyl, propyl, butyl, vinyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrogen, phenyl, 4-trifluoromethylphenyl, methyl, ethyl, vinyl, trifluoromethyl, trifluoromethoxymethyl, difluoromethyl, chlorodifluoromethyl, and pentafluoroethyl;

Y is methylene or oxy;

A is selected from the group consisting of

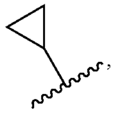 , 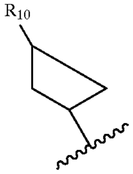 , 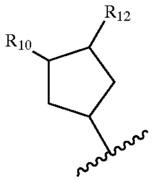 ,

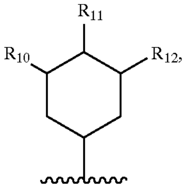 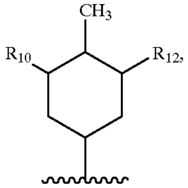

-continued

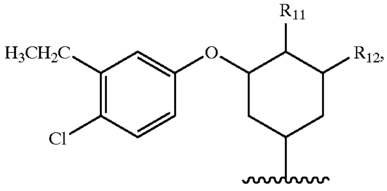

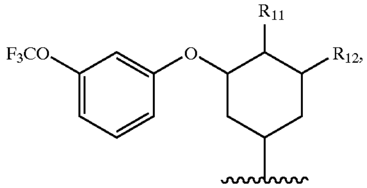

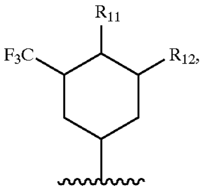 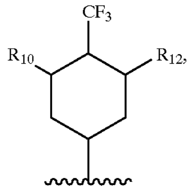

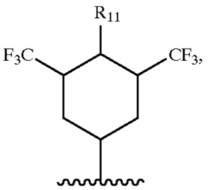 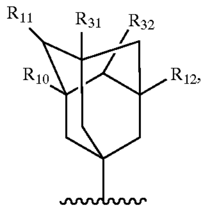

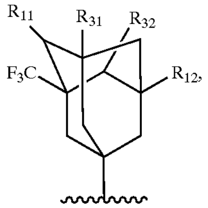 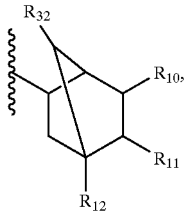

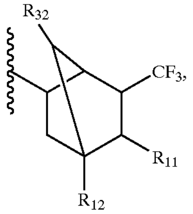 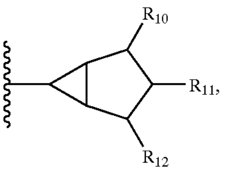

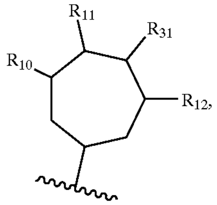 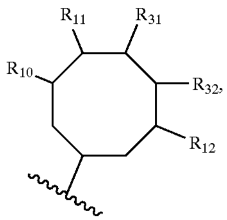

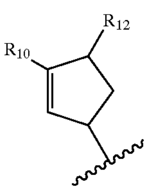 , 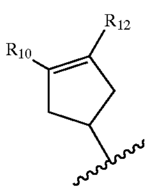 , 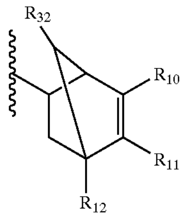 ,

-continued

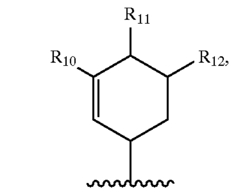
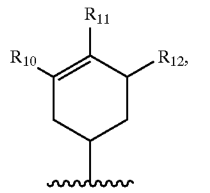
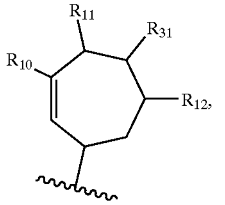
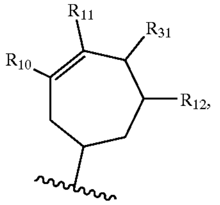
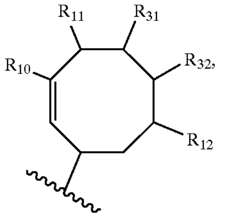
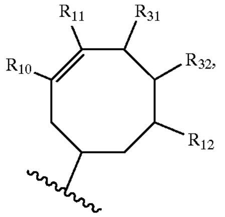
and
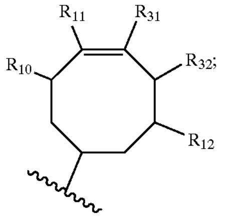

$R_4$ and $R_8$ are independently hydrogen or fluoro;

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethyl, and trifluoromethoxy, unless $R_6$ is bonded together with $R_5$ to form a partially saturated heterocyclyl ring having 5 through 8 members;

$R_7$ is selected from the group consisting of hydrogen, fluoro, and trifluoromethyl;

$R_{10}$ and $R_{12}$ are selected from the group consisting of hydrogen, 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isoamyl, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethoxy, pentafluoroethyl, 3-pentafluoroethylphenoxy, pentafluoroethylthio, 2,2,3,3,3-pentafluoropropyl, 1,1,3,3,3-pentafluoropropyl, 1,1,2,2,3-pentafluoropropyl, phenoxy, phenyl, phenylamino, 1-phenylethoxy, phenylsulfonyl, 4-propanoylphenoxy, propoxy, 4-propylphenoxy, 4-propoxyphenoxy, 2-pyridyl, thiophen-3-yl, sec-butyl, 4-sec-butylphenoxy, sec-butoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_{11}$, $R_{31}$, and $R_{32}$ are independently selected from the group consisting of hydrogen, chloro, fluoro, methyl, pentafluoroethyl, 1,1,2,2-tetrafluoroethoxy, trifluoromethyl, and trifluoromethoxy.

20. The method of claim 19, wherein said compound is of Formula GN, wherein;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrogen, methyl, ethyl, phenyl, 4-trifluoromethylphenyl, trifluoromethoxymethyl, 1,1,2,2-tetrafluoroethoxymethyl, difluoromethyl, pentafluoroethyl, trifluoromethyl, and 2,2,3,3,3-pentafluoropropyl;

$R_3$ is selected from the group consisting of hydrogen, phenyl, 4-trifluoromethylphenyl, methyl, trifluoromethyl, difluoromethyl, and chlorodifluoromethyl;

Y is methylene;

A is selected from the group consisting of

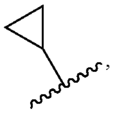,
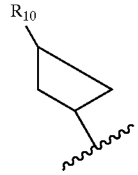,
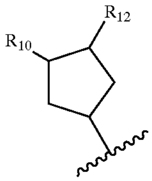,
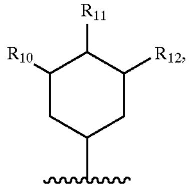
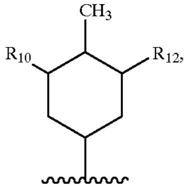
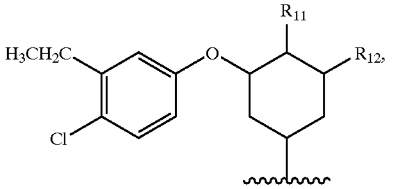
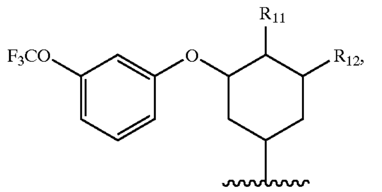
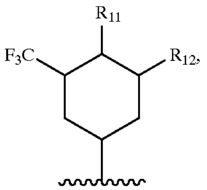
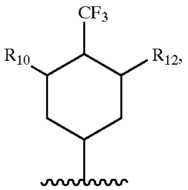

-continued

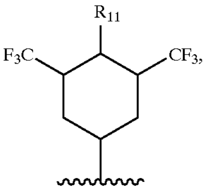
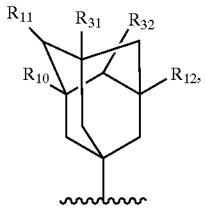
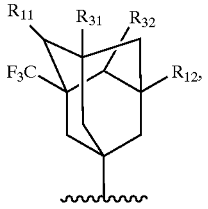
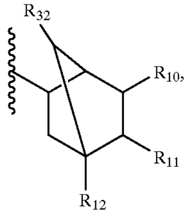
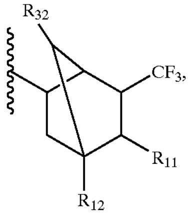
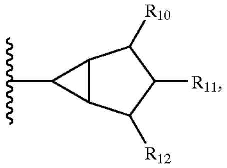
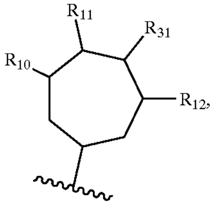
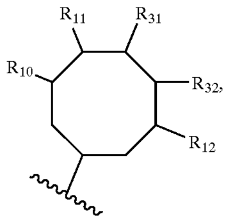 and
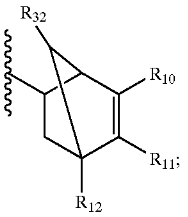

$R_5$ $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethoxy, and trifluoromethyl, unless $R_6$ is bonded together with $R_5$ to form a partially saturated heterocyclyl ring having 5 through 8 members;

$R_7$ is selected from the group consisting of hydrogen, fluoro, and trifluoromethyl;

$R_{10}$ and $R_{12}$ are selected from the group consisting of hydrogen, benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, cyclopropyl,2,3- dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy,3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, ethoxy, 3-ethylbenzyloxy, 3-ethylphenoxy, 4-ethylamino-phenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethyl-benzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethyl-phenoxy, 2-furyl, 3-furyl, heptafluoropropyl, 1,1,1,3,3,3-hexafluoro-2-propyl, 2-hydroxy-3,3,3-trifluoropropoxy, isoamyl, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethoxy, pentafluoroethyl, pentafluoroethylthio, 3-pentafluoroethylphenoxy, 2,2,3,3,3-pentafluoro-propyl, 1,1,3,3,3-pentafluoropropyl,1,1,2,2,3-pentafluoropropyl, phenoxy, phenyl, phenylamino, 1-phenylethoxy, 4-propylphenoxy, propoxy, 4-propoxyphenoxy, 2-pyridyl, thiophen-3-yl, sec-butoxy, tert -butoxy, 3-tert-butylphenoxy, 4-tert -butylphenoxy, 1,1,2,2-tetrafluoroethoxy, tetrahydrofuran-2-yl, 2-(5,6,7,8-tetrahydronaphthyl-oxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxy-benzyloxy, 4-trifluoromethoxyphenoxy, 3-trifluoromethoxyphenoxy, trifluoromethyl, 3-trifluoromethylbenzyloxy, 1,1-bis-trifluoromethyl-1 -hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoro-ethoxy)phenoxy, 3-trifluoromethylthiophenoxy, 3-trifluoromethylthiobenzyloxy, and trifluorometh-ylthio;

$R_{11}$, $R_{31}$, and $R_{32}$ are independently selected from the group consisting of hydrogen, chloro, fluoro, methyl, pentafluoroethyl, 1,1,2,2-tetrafluoroethoxy, and trifluoromethyl.

21. The method of claim 20, wherein said compound is of Formula GN, wherein;

$R_1$ is selected from the group consisting of trifluoromethyl, chlorodifluoromethyl, and pentafluoroethyl;

$R_2$ is hydrogen, pentafluoroethyl, and trifluoromethyl;

$R_3$ is selected from the group consisting of hydrogen, methyl, trifluoromethyl, and difluoromethyl;

A is selected from the group consisting of

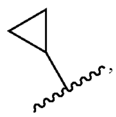, 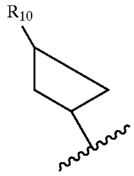, 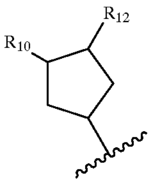,

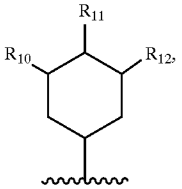

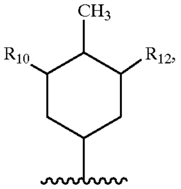

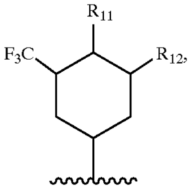

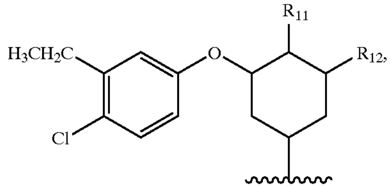

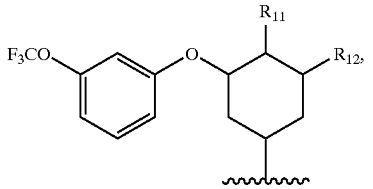

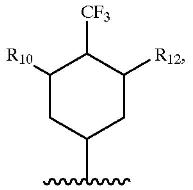

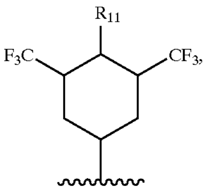

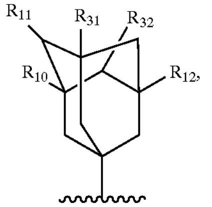

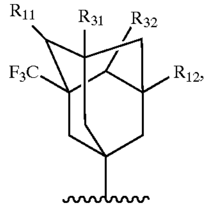

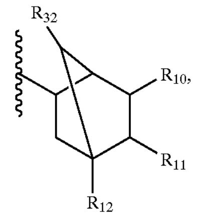

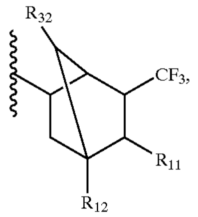

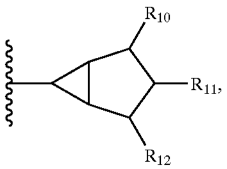 and 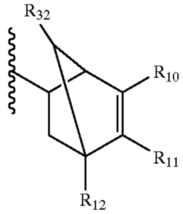 ;

$R_4$ and $R_8$ are independently hydrogen or fluoro;

$R_5$ is $R_{10}$ or bonded together with $R_6$ to form a partially saturated heterocyclyl ring having 5 through 8 members, with the proviso that $R_5$ is not hydrogen;

$R_6$ is selected from the group consisting of chloro, fluoro, hydrogen, pentafluoroethyl, 1,1,2,2-tetrafluoroethoxy, trifluoromethoxy, and trifluoromethyl, unless $R_6$ is bonded together with $R_5$ to form a partially saturated heterocyclyl ring having 5 through 8 members;

$R_7$ is hydrogen or fluoro;

$R_{10}$ and $R_{12}$ are selected from the group consisting of hydrogen, 5-bromo-2-fluorophenoxy, 4-chloro-3-ethylphenoxy, cyclopentoxy, cyclopentyl, cyclopropyl, cyclopropylmethoxy, 2,3-dichlorophenoxy, 3,4-dichlorophenoxy, 3-difluoromethoxyphenoxy, 3,5-dimethylphenoxy, 3,4-dimethylphenoxy, ethoxy, 3-ethylphenoxy, 3-ethyl-5-methylphenoxy, 4-fluoro-3-methylphenoxy, 4-fluorophenoxy, 2-furyl, 3-furyl, heptafluoropropyl, 1,1,1,3,3,3-hexafluoro-2-propyl, isoamyl, isobutoxy, isobutyl, isopropoxy, 3-isopropylphenoxy, 3-methylphenoxy, pentafluoroethoxy, pentafluoroethyl, 3-pentafluoroethylphenoxy, 2,2,3,3,3-pentafluoropropyl, phenoxy, phenyl, propoxy, 2-pyridyl, sec-butoxy, tert-butoxy, 3-tert-butylphenoxy, 1,1,2,2-tetrafluoroethoxy, 3-(1,1,2,2-tetrafluoroethoxy)phenoxy, tetrahydro-2-furyl, 2-(5,6,7,8-tetrahydronaphthyloxy), 2-thienyl, 2,2,2-trifluoroethoxy, 2,2,2-trifluoroethyl, trifluoromethoxy, 3-trifluoromethoxybenzyloxy, 3-trifluoromethoxyphenoxy, trifluoromethyl, 3-trifluoromethylbenzyloxy, 3-trifluoromethylphenoxy, 3,3,3-trifluoro-2-hydroxypropoxy, 1,1-bis-trifluoromethyl-1-hydroxymethyl, trifluoromethylthio, and 3-trifluoromethylthiophenoxy;

$R_{11}$, $R_{31}$, and $R_{32}$ are independently selected from the group consisting of hydrogen, chloro, fluoro, methyl, pentafluoroethyl, 1,1,2,2-tetrafluoroethoxy, and trifluoromethyl.

22. The method of claim 21, wherein said compound is of Formula GN, wherein;

$R_2$ is hydrogen;

$R_3$ is hydrogen;

A is selected from the group consisting of

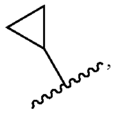,
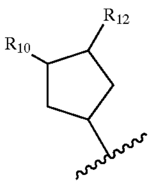,
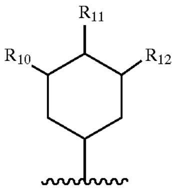,
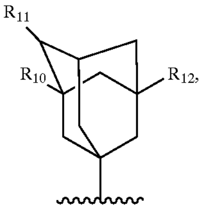
and
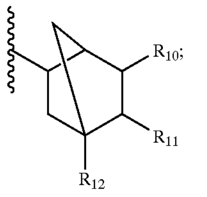

$R_5$ is selected from the group consisting of cyclopentoxy, cyclopentyl, cyclopropyl, cyclopropylmethoxy, ethoxy, 2-furyl, 3-furyl, heptafluoropropyl, 1,1,1,3,3,3-hexafluoro-2-propyl, isoamyl, isobutoxy, isobutyl, isopropoxy, pentafluoroethyl, pentafluoroethoxy, 2,2,3,3,3-pentafluoropropyl, phenoxy, phenyl, propoxy, 2-pyridyl, sec-butoxy, tert-butoxy, 1,1,2,2-tetrafluoroethoxy, tetrahydro-2-furyl,2-thienyl, 2,2,2-trifluoroethoxy, 2,2,2-trifluoroethyl, trifluoromethoxy, trifluoromethyl, 3-trifluoromethylphenoxy, 1,1-bis-trifluoromethyl-1-hydroxymethyl, trifluoromethylthio, and 3,3,3-trifluoro-2-hydroxypropoxy, unless $R_5$ is bonded together with $R_6$ to form 1,1,2,2-tetrafluoroethylene-1,2-dioxy;

$R_6$ is selected from the group consisting of fluoro, hydrogen, trifluoromethoxy, and trifluoromethyl, unless $R_6$ is bonded together with $R_5$ to form 1,1,2,2-tetrafluoroethylene-1,2-dioxy;

$R_7$ is hydrogen;

$R_{10}$ and $R_{12}$ are independently selected from the group consisting of hydrogen, 4-chloro-3-ethylphenoxy, isopropoxy, phenoxy, 3-trifluoromethoxyphenoxy, trifluoromethyl, and 3-trifluoromethylbenzyloxy;

$R_{11}$ is selected from the group consisting of hydrogen, methyl, and trifluoromethyl.

23. The method of claim 22, wherein said compound is selected from the group consisting of:

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1-trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-tetrafluoroethoxy)phenyl]methyl](4-methylcyclohexyl)amino]-1,1,1-trifluoro-2-propanol;

3-[[[(3-trifluoromethyl)phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4-chloro-3-ethylphenoxy)cyclohexyl]amino]-1,1,1-trifluoro-2-propanol;

3-[[[(3-trifluoromethoxy)phenyl]methyl][3-(4-chloro-3-ethylphenoxy)cyclohexyl]amino]-1,1,1-trifluoro-2-propanol;

3-[[[3-(1,1,2,2-tetrafluoroethoxy)phenyl]methyl][3-(4-chloro-3-ethyl-phenoxy)cyclohexyl]amino]-1,1,1-trifluoro-2-propanol;

3-[[[(3-trifluoromethyl)phenyl]methyl](3-phenoxycyclohexyl)amino]1,1,1-trifluoro-2-propanol;

3-[[[(3-pentafluoroethyl)phenyl]methyl](3-phenoxycyclohexyl)amino]1,1,1-trifluoro-2-propanol;

3-[[[(3-trifluoromethoxy)phenyl]methyl](3-phenoxycyclohexyl)amino]1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifluoromethyl)phenyl]methyl](3-isopropoxycyclohexyl)amino]1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)amino]-1,1,1-trifluoro-2-propanol;

3-[[[(3-trifluoromethyl)phenyl]methyl](3-cyclopentyloxycyclohexyl)amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol; and 3-[[[3-(1,2,2-tetrafluoroethoxy)phenyl]methyl](3-cyclopentyloxycyclohexyl)amino]-1,1,1-trifluoro-2-propanol.

24. The method of claim 22, wherein said compound is selected from the group consisting of:

3-[[[(3-trifluoromethyl)phenyl]methyl][(4-methyl)cyclohexyl]amino]-1,1,1-trifluoro-2-propanol;

3-[[[(3-trifluoromethoxy)phenyl]methyl][cyclopropyl]amino]-1,1,1-trifluoro-2-propanol;

3-[[[(4-trifluoromethoxy)phenyl]methyl][cyclopropyl]amino]-1,1,1-trifluoro-2-propanol; and 3-[[[(3-trifluoromethoxy)phenyl]methyl][cyclopentyl]amino]-1,1,1-trifluoro-2-propanol.

25. The method of claim 17 further characterized by treating coronary artery disease in a subject by administering a therapeutically effective amount of a compound of claim 17 or a pharmaceutically acceptable salt thereof.

26. The method of claim 17 further characterized by preventing coronary artery disease in a subject by administering a therapeutically effective amount of a compound of claim 17 or a pharmaceutically acceptable salt thereof.

27. The method of claim 17 further characterized by preventing cerebral vascular accident (CVA) in a subject by administering a therapeutically effective amount of a compound of claim 17 or a pharmaceutically acceptable salt thereof.

28. The method of claim 17 further characterized by treating or preventing dyslipidemia in a subject by administering a therapeutically effective amount of a compound of claim 17 or a pharmaceutically acceptable salt thereof.

* * * * *